US008389575B2

(12) United States Patent
DiCosimo et al.

(10) Patent No.: US 8,389,575 B2
(45) Date of Patent: *Mar. 5, 2013

(54) CONTROL OF ENZYMATIC PERACID GENERATION

(75) Inventors: Robert DiCosimo, Chadds Ford, PA (US); Mark Scott Payne, Wilmington, DE (US); Eugenia Costa Hann, Carneys Point, NJ (US)

(73) Assignee: E.I. du Pont de Nemours and Company, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 13/354,486

(22) Filed: Jan. 20, 2012

(65) Prior Publication Data
US 2012/0122979 A1 May 17, 2012

Related U.S. Application Data

(62) Division of application No. 12/359,025, filed on Aug. 11, 2009, now Pat. No. 8,129,153.

(60) Provisional application No. 61/088,673, filed on Aug. 13, 2008, provisional application No. 61/102,520, filed on Oct. 3, 2008.

(51) Int. Cl.
*A01N 37/00* (2006.01)
*C12P 7/40* (2006.01)
*C12N 9/14* (2006.01)

(52) U.S. Cl. .................. 514/557; 435/136; 435/197
(58) Field of Classification Search .................. None
See application file for complete search history.

(56) References Cited

U.S. PATENT DOCUMENTS

| | | |
|---|---|---|
| 3,974,082 A | 8/1976 | Weyn |
| 4,585,150 A | 4/1986 | Beacham et al. |
| 5,116,575 A | 5/1992 | Badertscher et al. |
| 5,281,525 A | 1/1994 | Mitsushima et al. |
| 5,296,161 A | 3/1994 | Wiersema et al. |
| 5,338,676 A | 8/1994 | Mitsushima et al. |
| 5,364,554 A | 11/1994 | Stanislowski et al. |
| 5,398,846 A | 3/1995 | Corba et al. |
| 5,528,152 A | 6/1996 | Hinoshita et al. |
| 5,624,634 A | 4/1997 | Brougham et al. |
| 5,683,724 A | 11/1997 | Hei et al. |
| 5,932,532 A | 8/1999 | Ghosh et al. |
| 6,183,807 B1 | 2/2001 | Gutzmann et al. |
| 6,210,639 B1 | 4/2001 | Vlass et al. |
| 6,319,888 B2 | 11/2001 | Wei et al. |
| 6,391,840 B1 | 5/2002 | Thompson et al. |
| 6,465,233 B1 | 10/2002 | Knauseder et al. |
| 6,518,307 B2 | 2/2003 | McKenzie et al. |
| 6,545,047 B2 | 4/2003 | Gutzmann et al. |
| 6,635,286 B2 | 10/2003 | Hei et al. |
| 6,645,233 B1 | 11/2003 | Ayers et al. |
| 6,995,125 B2 | 2/2006 | Dasque et al. |
| 7,448,556 B2 | 11/2008 | Muehlhausen et al. |
| 7,723,083 B2 | 5/2010 | DiCosimo et al. |
| 7,951,566 B2 | 5/2011 | Dicosimo et al. |
| 7,964,378 B2 | 6/2011 | Dicosimo et al. |
| 2005/0008526 A1 | 1/2005 | Bianchetti et al. |
| 2008/0176299 A1 | 7/2008 | Dicosimo et al. |

FOREIGN PATENT DOCUMENTS

| | | |
|---|---|---|
| EP | 0807156 B1 | 11/1997 |
| WO | WO99/03984 | 1/1999 |
| WO | WO00/61713 | 10/2000 |
| WO | WO2007106293 A | 9/2007 |

OTHER PUBLICATIONS

Abbott et al., Physical Properties and Kinetic Behavior of a Cephalosporin . . . , Appl. Microbial. 30(3):413-419 (1975).
Cardoza et al., A Cephalosporin C Acetylhydrolase is Present in the Cultures . . . , Appl. Microbiol. Biotechnol., 54(3):406-412 (2000).
Degrassi et al., The Acetyl Xylan Esterase of *Bacillus pumilus* Belongs . . . , Microbiology, 146:1585-1591 (2000).
Gilbert et al., Recent Advances in Carbohydrate Bioengineering, the Royal Society of Chemistry, Cambridge, pp. 3-12, (1999).
Kobayashi et al., Purification and Properties of an Alkaline Protease from Alkalophilic . . . , Appl. Microbiol. Biotechnol. 43:473-481 (1995).
Kunst et al., The Complete Genome Sequence of the Gram-Positive Bacterium *Bacillus subtilis*, Nature 390:249-56 (1997).
Lee et al., Genetic Organization, Sequence and Biochemical Characterization of Recombinant . . . , J.G., J Gen Microbiol., 139:1235-1243 (1993).
Lorenz, et al., Isolation, Analysis, and Expression of Two Genes From *Thermoanaerobacterium* . . . , J. Bacteriol 179:5436-5441 (1997).
Mitsushima et al., Gene Cloning, Nucleotide Sequence, and Expression . . . , Appl. Environ. Microbiol. 61(6): 2224-2229 (1995).
Nelson et al., Evidence for Lateral Gene Transfer Between Archaea and Bacteria From Genome Sequence of *Thermotoga maritime*, Nature 399 (6734):323-329 (1999).
Payne et al., Use of Alkaline Phosphatase Fusions to Study Protein Secretion in *Bacillus subtilis*, J. Bacteriol. 173:2278-2282 (1991).
Pinkernell et al., Simultaneous Hplc Determination of Peroxyacetic Acid and Hydrogen Peroxide, (Anal. Chem., 69(17):3623-3627 (1997).
Politino et al., Purification and Characterization of a Cephalosporin Esterase from *Rhodosporidium toruloides*, Appl. Environ. Microbiol., 63(12):4807-4811 (1997.

(Continued)

*Primary Examiner* — Tekchand Saidha
*Assistant Examiner* — Md. Younus Meah

(57) ABSTRACT

A process is provided for producing target concentrations of peroxycarboxylic acids from carboxylic acid esters. More specifically, carboxylic acid esters are reacted with an inorganic peroxide, such as hydrogen peroxide, in the presence of an enzyme catalyst having perhydrolysis activity under conditions where control of reaction pH by selection of buffer concentration and concentration of perhydrolase and reactants produces a targeted concentration of peroxycarboxylic acids. The present perhydrolase catalysts are classified as members of the carbohydrate esterase family 7 (CE-7) based on the conserved structural features. Further, disinfectant formulations comprising the peracids produced by the processes described herein are provided, as are corresponding methods of use.

18 Claims, No Drawings

OTHER PUBLICATIONS

Rey et al., Complete Genome Sequence of the Industrial Bacterium *Bacillus* . . ., Genome Biol., 5(10): article 77 (2004).

Sakai et al., Purification and Properties of Cephalosporin-C Deacetylase From the Yeast . . . , J. Ferment. Bioeng. 85:53-57 (1998).

Takami et al., Complete Genome Sequence of the Alkaliphilic . . . , Nar, 28(21):4317-4331 (2000).

Vincent et al., Multifunctional Xylooligosaccharide/Cephalosporin C Deacetylase Revealed by the Hexameric . . . , J. Mol. Biol., 330:593-606 (2003).

Corresponding International Search Report and Written Opinion (PCT/ US2009/053365) mailed Dec. 16, 2009.

U.S. Appl. No. 12/539,025, Restriction mailed Apr. 10, 2011.

U.S. Appl. No. 12/539,025, Notice of Allowance and Fees mailed Dec. 9, 2011.

SEQUENCE LISTING

```
<160> NUMBER OF SEQ ID NOS: 73

<210> SEQ ID NO 1
<211> LENGTH: 960
<212> TYPE: DNA
<213> ORGANISM: Bacillus subtilis
<220> FEATURE:
<221> NAME/KEY: CDS
<222> LOCATION: (1)..(960)

<400> SEQUENCE: 1 atg caa cta ttc gat ctg ccg ctc gac caa ttg caa aca tat aag cct       48
Met Gln Leu Phe Asp Leu Pro Leu Asp Gln Leu Gln Thr Tyr Lys Pro
1               5                   10                  15 gaa aaa aca gca ccg aaa gat ttt tct gag ttt tgg aaa ttg tct ttg       96
Glu Lys Thr Ala Pro Lys Asp Phe Ser Glu Phe Trp Lys Leu Ser Leu
            20                  25                  30 gag gaa ctt gca aaa gtc caa gca gaa cct gat tta cag ccg gtt gac      144
Glu Glu Leu Ala Lys Val Gln Ala Glu Pro Asp Leu Gln Pro Val Asp
        35                  40                  45 tat cct gct gac gga gta aaa gtg tac cgt ctc aca tat aaa agc ttc      192
Tyr Pro Ala Asp Gly Val Lys Val Tyr Arg Leu Thr Tyr Lys Ser Phe
    50                  55                  60 gga aac gcc cgc att acc gga tgg tac gcg gtg cct gac aag caa ggc      240
Gly Asn Ala Arg Ile Thr Gly Trp Tyr Ala Val Pro Asp Lys Gln Gly
65                  70                  75                  80 ccg cat ccg gcg atc gtg aaa tat cat ggc tac aat gca agc tat gat      288
Pro His Pro Ala Ile Val Lys Tyr His Gly Tyr Asn Ala Ser Tyr Asp
                85                  90                  95 ggt gag att cat gaa atg gta aac tgg gca ctc cat ggc tac gcc gca      336
Gly Glu Ile His Glu Met Val Asn Trp Ala Leu His Gly Tyr Ala Ala
            100                 105                 110 ttc ggc atg ctt gtc cgc ggc cag cag agc agc gag gat acg agt att      384
Phe Gly Met Leu Val Arg Gly Gln Gln Ser Ser Glu Asp Thr Ser Ile
        115                 120                 125 tca ctg cac ggt cac gct ttg ggc tgg atg acg aaa gga att ctt gat      432
Ser Leu His Gly His Ala Leu Gly Trp Met Thr Lys Gly Ile Leu Asp
    130                 135                 140 aaa gat aca tac tat tac cgc ggt gtt tat ttg gac gcc gtc cgc gcg      480
```

```
Lys Asp Thr Tyr Tyr Tyr Arg Gly Val Tyr Leu Asp Ala Val Arg Ala
145                 150                 155                 160 ctt gag gtc atc agc agc ttc gac gag gtt gac gaa aca agg atc ggt    528
Leu Glu Val Ile Ser Ser Phe Asp Glu Val Asp Glu Thr Arg Ile Gly
                165                 170                 175 gtg aca gga gga agc caa ggc gga ggt tta acc att gcc gca gca gcg    576
Val Thr Gly Gly Ser Gln Gly Gly Gly Leu Thr Ile Ala Ala Ala Ala
            180                 185                 190 ctg tca gac att cca aaa gcc gcg gtt gcc gat tat cct tat tta agc    624
Leu Ser Asp Ile Pro Lys Ala Ala Val Ala Asp Tyr Pro Tyr Leu Ser
        195                 200                 205 aac ttc gaa cgg gcc att gat gtg gcg ctt gaa cag ccg tac ctt gaa    672
Asn Phe Glu Arg Ala Ile Asp Val Ala Leu Glu Gln Pro Tyr Leu Glu
    210                 215                 220 atc aat tcc ttc ttc aga aga aat ggc agc ccg gaa aca gaa gtg cag    720
Ile Asn Ser Phe Phe Arg Arg Asn Gly Ser Pro Glu Thr Glu Val Gln
225                 230                 235                 240 gcg atg aag aca ctt tca tat ttc gat att atg aat ctc gct gac cga    768
Ala Met Lys Thr Leu Ser Tyr Phe Asp Ile Met Asn Leu Ala Asp Arg
                245                 250                 255 gtg aag gtg cct gtc ctg atg tca atc ggc ctg att gac aag gtc acg    816
Val Lys Val Pro Val Leu Met Ser Ile Gly Leu Ile Asp Lys Val Thr
            260                 265                 270 ccg ccg tcc acc gtg ttt gcc gcc tac aat cat ttg gaa aca gag aaa    864
Pro Pro Ser Thr Val Phe Ala Ala Tyr Asn His Leu Glu Thr Glu Lys
        275                 280                 285 gag ctg aag gtg tac cgc tac ttc gga cat gag tat atc cct gct ttt    912
Glu Leu Lys Val Tyr Arg Tyr Phe Gly His Glu Tyr Ile Pro Ala Phe
    290                 295                 300 caa acg gaa aaa ctt gct ttc ttt aag cag cat ctt aaa ggc tga taa    960
Gln Thr Glu Lys Leu Ala Phe Phe Lys Gln His Leu Lys Gly
305                 310                 315

<210> SEQ ID NO 2
<211> LENGTH: 318
<212> TYPE: PRT
<213> ORGANISM: Bacillus subtilis

<400> SEQUENCE: 2

Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
                20                  25                  30

Glu Glu Leu Ala Lys Val Gln Ala Glu Pro Asp Leu Gln Pro Val Asp
            35                  40                  45

Tyr Pro Ala Asp Gly Val Lys Val Tyr Arg Leu Thr Tyr Lys Ser Phe
        50                  55                  60

Gly Asn Ala Arg Ile Thr Gly Trp Tyr Ala Val Pro Asp Lys Gln Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Leu His Gly His Ala Leu Gly Trp Met Thr Lys Gly Ile Leu Asp
    130                 135                 140

Lys Asp Thr Tyr Tyr Tyr Arg Gly Val Tyr Leu Asp Ala Val Arg Ala
145                 150                 155                 160
```

```
Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
        275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315

<210> SEQ ID NO 3
<211> LENGTH: 957
<212> TYPE: DNA
<213> ORGANISM: Bacillus subtilis

<400> SEQUENCE: 3
atgcaactat tcgatctgcc gctcgaccaa ttgcaaacat ataagcctga aaaaacagca      60
ccgaaagatt tttctgagtt ttggaaattg tctttggagg aacttgcaaa agtccaagca     120
gaacctgatt tacagccggt tgactatcct gctgacggag taaaagtgta ccgtctcaca     180
tataaaagct tcggaaacgc ccgcattacc ggatggtacg cggtgcctga caaggaaggc     240
ccgcatccgg cgatcgtgaa atatcatggc tacaatgcaa gctatgatgg tgagattcat     300
gaaatggtaa actgggcact ccatggctac gccacattcg gcatgcttgt ccgcggccag     360
cagagcagcg aggatacgag tatttcaccg cacggtcacg cttttgggcct gatgacgaaa     420 ggaattcttg ataaagatac atactattac cgcggtgttt atttggacgc cgtccgcgcg     480
cttgaggtca tcagcagctt cgacgaggtt gacgaaacaa ggatcggtgt gacaggagga     540
agccaaggcg aggtttaac cattgccgca gcagcgctgt cagacattcc aaaagccgcg     600
gttgccgatt atccttattt aagcaacttc gaacgggcca ttgatgtggc gcttgaacag     660
ccgtaccttg aaatcaattc cttcttcaga gaaatggca gcccggaaac agaagtgcag     720
gcgatgaaga cactttcata tttcgatatt atgaatctcg ctgaccgagt gaaggtgcct     780
gtcctgatgt caatcggcct gattgacaag gtcacgccgc cgtccaccgt gtttgccgcc     840
tacaatcatt tggaaacaaa gaaagagctg aaggtgtacc gctacttcgg acatgagtat     900
atccctgctt tcaaaactga aaaacttgct ttctttaagc agcatcttaa aggctga     957

<210> SEQ ID NO 4
<211> LENGTH: 318
<212> TYPE: PRT
<213> ORGANISM: Bacillus subtilis

<400> SEQUENCE: 4

Met Gln Leu Phe Asp Leu Pro Leu Asp Gln Leu Gln Thr Tyr Lys Pro
```

```
                1               5                  10                 15
Glu Lys Thr Ala Pro Lys Asp Phe Ser Glu Phe Trp Lys Leu Ser Leu
                    20                 25                 30

Glu Glu Leu Ala Lys Val Gln Ala Glu Pro Asp Leu Gln Pro Val Asp
                    35                 40                 45

Tyr Pro Ala Asp Gly Val Lys Val Tyr Arg Leu Thr Tyr Lys Ser Phe
                    50                 55                 60

Gly Asn Ala Arg Ile Thr Gly Trp Tyr Ala Val Pro Lys Glu Gly
65                   70                 75                     80

Pro His Pro Ala Ile Val Lys Tyr His Gly Tyr Asn Ala Ser Tyr Asp
                        85                 90                 95

Gly Glu Ile His Glu Met Val Asn Trp Ala Leu His Gly Tyr Ala Thr
                        100                105                110

Phe Gly Met Leu Val Arg Gly Gln Gln Ser Ser Glu Asp Thr Ser Ile
                        115                120                125

Ser Pro His Gly His Ala Leu Gly Trp Met Thr Lys Gly Ile Leu Asp
                        130                135                140

Lys Asp Thr Tyr Tyr Tyr Arg Gly Val Tyr Leu Asp Ala Val Arg Ala
145                     150                155                160

Leu Glu Val Ile Ser Ser Phe Asp Glu Val Asp Thr Arg Ile Gly
                        165                170                    175

Val Thr Gly Gly Ser Gln Gly Gly Leu Thr Ile Ala Ala Ala Ala
                        180                185                190

Leu Ser Asp Ile Pro Lys Ala Ala Val Ala Asp Tyr Pro Tyr Leu Ser
                        195                200                205

Asn Phe Glu Arg Ala Ile Asp Val Ala Leu Glu Gln Pro Tyr Leu Glu
                        210                215                220

Ile Asn Ser Phe Phe Arg Arg Asn Gly Ser Pro Glu Thr Glu Val Gln
225                     230                235                240

Ala Met Lys Thr Leu Ser Tyr Phe Asp Ile Met Asn Leu Ala Asp Arg
                        245                250                255

Val Lys Val Pro Val Leu Met Ser Ile Gly Leu Ile Asp Lys Val Thr
                        260                265                270

Pro Pro Ser Thr Val Phe Ala Ala Tyr Asn His Leu Glu Thr Lys Lys
                        275                280                285

Glu Leu Lys Val Tyr Arg Tyr Phe Gly His Glu Tyr Ile Pro Ala Phe
                        290                295                300

Gln Thr Glu Lys Leu Ala Phe Phe Lys Gln His Leu Lys Gly
305                     310                315

<210> SEQ ID NO 5
<211> LENGTH: 957
<212> TYPE: DNA
<213> ORGANISM: Bacillus subtilis

<400> SEQUENCE: 5
atgcaactat tcgatctgcc gctcgaccaa ttgcaaacgt ataagcctga aaaaacaaca    60
ccgaacgatt tttctgagtt ttggaaatcg tctttggacg aacttgcgaa agtcaaagca   120
gcacctgatt tacagctggt tgattatcct gctgatggag tcaaggtgta ccgcctcaca   180
tataaaagct tcggaaacgc ccgcattacc ggatggtacg cagtgcctga caaggaagga   240
ccgcatccgg cgatcgtcaa atatcatggc tacaacgcta gctatgacgg tgagattcat   300
gaaatggtaa actgggcgct ccacggttac gccgcattcg gcatgctagt ccgcggccag   360
cagagcagcg aggatacgag tatttctcca catggccatg ctttgggctg atgacgaaa    420
```

```
ggaatccttg ataaagatac atactattac cggggcgttt atttggacgc tgtccgcgcg    480
cttgaggtca tcagcagctt tgacgaagtt gacgaaacaa gaatcggtgt gacaggcgga    540
agccaaggag gcggcttaac cattgccgca gccgctctgt cagacattcc aaaagccgcg    600
gttgccgatt atccttattt aagcaacttt gaacgggcca ttgatgtggc gcttgaacag    660
ccgtaccttg aaatcaattc cttctttaga gaaatggaa gcccggaaac ggaagagaag    720
gcgatgaaga cactttcata tttcgatatt atgaatctcg ctgaccgagt gaaggtccct    780
gtcctgatgt cgatcggtct gattgacaag gtcacgccgc cgtccaccgt gtttgccgca    840
tacaaccact tggagacaga gaaagagctc aaagtgtacc gctacttcgg gcatgagtat    900
atccctgcct ttcaaacaga aaaacttgct ttctttaagc agcatcttaa aggctga      957
```

<210> SEQ ID NO 6
<211> LENGTH: 318
<212> TYPE: PRT
<213> ORGANISM: Bacillus subtilis

<400> SEQUENCE: 6

```
Met Gln Leu Phe Asp Leu Pro Leu Asp Gln Leu Gln Thr Tyr Lys Pro
 1               5                  10                  15

Glu Lys Thr Thr Pro Asn Asp Phe Ser Glu Phe Trp Lys Ser Ser Leu
            20                  25                  30

Asp Glu Leu Ala Lys Val Lys Ala Ala Pro Asp Leu Gln Leu Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Glu Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
           100                 105                 110

Phe Gly Met Leu Val Arg Gly Gln Gln Ser Ser Glu Asp Thr Ser Ile
       115                 120                 125

Ser Pro His Gly His Ala Leu Gly Trp Met Thr Lys Gly Ile Leu Asp
   130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Glu Lys
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
        275                 280                 285
```

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315

<210> SEQ ID NO 7
<211> LENGTH: 957
<212> TYPE: DNA
<213> ORGANISM: Bacillus licheniformis

<400> SEQUENCE: 7

```
atgcagcagc cttatgatat gccgcttgaa cagctttatc agtataaacc tgaacggacg      60
gcaccggccg attttaaaga gttctggaag ggttcattgg aggaattggc aaatgaaaaa     120
gcgggaccgc agcttgaacc gcatgaatat ccggctgacg gggtaaaagt ctactggctt     180
acatacagaa gcatcggggg agcgcgaatt aaaggctggt acgcagtacc cgaccgccaa     240
gggcctcatc ctgcgatcgt caaataccac ggctataacg caagctatga cggagacatt     300
cacgatattg tcaattgggc tcttcacggc tatgcggcat tcggtatgct ggtccgcgga     360
cagaacagca gtgaagatac agatctctct catcacggca tgtacccgg ctggatgaca     420
aaaggaatcc tcgatccgaa aacatattac tacagagggg tctatttaga tgccgtacga     480
gcagtcgaag tggtcagcgg ttttgctgaa gtcgatgaaa gcggatcgg ggtgatcggg      540
gcaagccaag gaggcgggct ggccgtcgcg gtttcggcgc tgtccgatat ccaaaagca     600
gccgtgtcag ataccccta tttaagcaat tttcaacgag cgatcgatac agcgatcgac     660
cagccatatc tcgaaatcaa ctccttttt agaagaaaca ccagtccgga tattgagcag     720
gcggccatgc ataccctgtc ttatttcgat gtcatgaacc ttgcccaatt ggtcaaagcg     780
accgtactca tgtcgatcgg actggttgac accatcactc cgccatccac cgtctttgcg     840
gcttacaatc acttggaaac ggataaagaa ataaaagtgt accgttattt tggacacgaa     900
tacatcccgc cgttccaaac cgaaaagctg gcgtttctga aaagcatct gaaataa        957
```

<210> SEQ ID NO 8
<211> LENGTH: 318
<212> TYPE: PRT
<213> ORGANISM: Bacillus licheniformis

<400> SEQUENCE: 8

Met Gln Gln Pro Tyr Asp Met Pro Leu Glu Gln Leu Tyr Gln Tyr Lys
1               5                  10                  15

Pro Glu Arg Thr Ala Pro Ala Asp Phe Lys Glu Phe Trp Lys Gly Ser
            20                  25                  30

Leu Glu Leu Ala Asn Glu Lys Ala Gly Pro Gln Leu Glu Pro His
        35                  40                  45

Glu Tyr Pro Ala Asp Gly Val Lys Val Tyr Trp Leu Thr Tyr Arg Ser
    50                  55                  60

Ile Gly Gly Ala Arg Ile Lys Gly Trp Tyr Ala Val Pro Asp Arg Gln
65                  70                  75                  80

Gly Pro His Pro Ala Ile Val Lys Tyr His Gly Tyr Asn Ala Ser Tyr
                85                  90                  95

Asp Gly Asp Ile His Asp Ile Val Asn Trp Ala Leu His Gly Tyr Ala
            100                 105                 110

Ala Phe Gly Met Leu Val Arg Gly Gln Asn Ser Ser Glu Asp Thr Glu
        115                 120                 125

Ile Ser His His Gly His Val Pro Gly Trp Met Thr Lys Gly Ile Leu

```
                  130                 135                 140
Asp Pro Lys Thr Tyr Tyr Tyr Arg Gly Val Tyr Leu Asp Ala Val Arg
145                 150                 155                 160

Ala Val Glu Val Val Ser Gly Phe Ala Glu Val Asp Glu Lys Arg Ile
                165                 170                 175

Gly Val Ile Gly Ala Ser Gln Gly Gly Leu Ala Val Ala Val Ser
            180                 185                 190

Ala Leu Ser Asp Ile Pro Lys Ala Ala Val Ser Glu Tyr Pro Tyr Leu
            195                 200                 205

Ser Asn Phe Gln Arg Ala Ile Asp Thr Ala Ile Asp Gln Pro Tyr Leu
210                 215                 220

Glu Ile Asn Ser Phe Phe Arg Arg Asn Thr Ser Pro Asp Ile Glu Gln
225                 230                 235                 240

Ala Ala Met His Thr Leu Ser Tyr Phe Asp Val Met Asn Leu Ala Gln
                245                 250                 255

Leu Val Lys Ala Thr Val Leu Met Ser Ile Gly Leu Val Asp Thr Ile
            260                 265                 270

Thr Pro Pro Ser Thr Val Phe Ala Ala Tyr Asn His Leu Glu Thr Asp
            275                 280                 285

Lys Glu Ile Lys Val Tyr Arg Tyr Phe Gly His Glu Tyr Ile Pro Pro
290                 295                 300

Phe Gln Thr Glu Lys Leu Ala Phe Leu Arg Lys His Leu Lys
305                 310                 315

<210> SEQ ID NO 9
<211> LENGTH: 963
<212> TYPE: DNA
<213> ORGANISM: Bacillus pumilis

<400> SEQUENCE: 9
atgcaattgt cgatttatc actagaagag ctaaaaaaat ataaccaaa gaaaacagca      60
cgtcctgatt tctcagactt ttggaagaaa tcgctcgaag aactgcgcca agtggaggca     120
gagccaacac ttgaatctta tgactatcca gtgaaaggcg tcaaggtgta ccgcctgacg     180
tatcaaagct ttggacattc taaaattgaa ggcttttatg ctgtgcctga tcaaactggt     240
ccgcatccag cgctcgttcg ttttcatggc tataatgcca gctatgacgg cggcattcac     300
gacatcgtca actgggcgct gcacggctat gcaacatttg gtatgctcgt ccgcggtcaa     360
ggtggcagtg aagacacatc agtgacacca ggcgggcatg cattagggtg gatgacaaaa     420
ggcatttat cgaaagatac gtactattat cgaggcgttt atctagatgc tgttcgtgca     480
cttgaagtca ttcagtcttt ccccgaagta gatgaacacc gtatcggcgt gatcggtgga     540
agtcaggggg gtgcgttagc gattgcggcc gcagcccttt cagacattcc aaaagtcgtt     600
gtggcagact atccttactt atcaaatttt gagcgtgcag ttgatgttgc cttggagcag     660
ccttatttag aaatcaattc atactttcgc agaaacagtg atccgaaagt ggaggaaaag     720
gcatttgaga cattaagcta tttgattta atcaatttag ctggatgggt gaaacagcca     780
acattgatgg cgatcggtct gattgacaaa ataaccccac catctactgt gtttgcggca     840
tacaaccatt tagaaacaga taaagacctg aaagtatatc gctatttgg acacgagttt     900
atccctgctt tcaaacagag aagctgtcc tttttacaaa agcatttgct tctatcaaca     960
taa                                                                  963

<210> SEQ ID NO 10
<211> LENGTH: 320
```

<212> TYPE: PRT
<213> ORGANISM: Bacillus pumilis

<400> SEQUENCE: 10

```
Met Gln Leu Phe Asp Leu Ser Leu Glu Glu Leu Lys Lys Tyr Lys Pro
1               5                   10                  15
Lys Lys Thr Ala Arg Pro Asp Phe Ser Asp Phe Trp Lys Lys Ser Leu
            20                  25                  30
Glu Glu Leu Arg Gln Val Glu Ala Glu Pro Thr Leu Glu Ser Tyr Asp
        35                  40                  45
Tyr Pro Val Lys Gly Val Lys Val Tyr Arg Leu Thr Tyr Gln Ser Phe
    50                  55                  60
Gly His Ser Lys Ile Glu Gly Phe Tyr Ala Val Pro Asp Gln Thr Gly
65                  70                  75                  80
Pro His Pro Ala Leu Val Arg Phe His Gly Tyr Asn Ala Ser Tyr Asp
                85                  90                  95
Gly Gly Ile His Asp Ile Val Asn Trp Ala Leu His Gly Tyr Ala Thr
            100                 105                 110
Phe Gly Met Leu Val Arg Gly Gln Gly Gly Ser Glu Asp Thr Ser Val
        115                 120                 125
Thr Pro Gly Gly His Ala Leu Gly Trp Met Thr Lys Gly Ile Leu Ser
    130                 135                 140
Lys Asp Thr Tyr Tyr Tyr Arg Gly Val Tyr Leu Asp Ala Val Arg Ala
145                 150                 155                 160
Leu Glu Val Ile Gln Ser Phe Pro Glu Val Asp Glu His Arg Ile Gly
                165                 170                 175
Val Ile Gly Gly Ser Gln Gly Gly Ala Leu Ala Ile Ala Ala Ala Ala
            180                 185                 190
Leu Ser Asp Ile Pro Lys Val Val Ala Asp Tyr Pro Tyr Leu Ser
                195                 200                 205
Asn Phe Glu Arg Ala Val Asp Val Ala Leu Glu Gln Pro Tyr Leu Glu
        210                 215                 220
Ile Asn Ser Tyr Phe Arg Arg Asn Ser Asp Pro Lys Val Glu Glu Lys
225                 230                 235                 240
Ala Phe Glu Thr Leu Ser Tyr Phe Asp Leu Ile Asn Leu Ala Gly Trp
                245                 250                 255
Val Lys Gln Pro Thr Leu Met Ala Ile Gly Leu Ile Asp Lys Ile Thr
            260                 265                 270
Pro Pro Ser Thr Val Phe Ala Ala Tyr Asn His Leu Glu Thr Asp Lys
        275                 280                 285
Asp Leu Lys Val Tyr Arg Tyr Phe Gly His Glu Phe Ile Pro Ala Phe
    290                 295                 300
Gln Thr Glu Lys Leu Ser Phe Leu Gln Lys His Leu Leu Ser Thr
305                 310                 315                 320
```

<210> SEQ ID NO 11
<211> LENGTH: 963
<212> TYPE: DNA
<213> ORGANISM: Clostridium thermocellum

<400> SEQUENCE: 11
atggcacaat tatatgatat gcctttggag gaattaaaaa aatataagcc tgcgcttaca      60
aaacagaaag attttgatga gttttgggaa aaaagcctta agagctggc tgaaattcct      120 ttaaatatc aacttatacc ttatgatttt ccggcccgga gggtaaaagt ttcagagtt       180 gaatatcttg gttttaaagg tgcaaatatt gaagggtggc ttgccgttcc cgagggagaa      240

```
gggttgtatc ccgggcttgt acagtttcac ggatacaact gggcgatgga tggatgtgtt    300
cccgatgtgg taaattgggc tttgaatgga tatgccgcat ttcttatgct tgttcgggga    360
cagcagggaa gaagcgtgga caatattgtg cccggcagcg gtcatgcttt gggatggatg    420
tcgaaaggta ttttgtcacc ggaggaatat tattatagag gagtatatat ggatgcggtt    480
cgtgctgttg aaattttggc ttcgcttcct tgtgtggatg aatcgagaat aggagtgaca    540
gggggcagcc agggtggagg acttgcactg gcggtggctg ctctgtccgg cataccgaaa    600
gttgcagccg tgcattatcc gtttctggca catttttgagc gtgccattga cgttgcgccg    660 gacggcccctt atcttgaaat taacgaatat ttaagaagaa acagcggtga agaaatagaa    720
agacaggtaa agaaaacccct ttcctatttt gatatcatga atcttgctcc ccgtataaaa    780
tgccgtactt ggatttgcac tggtcttgtg gatgagatta ctcctccgtc aacggttttt    840
gcagtgtaca atcacctcaa atgcccaaag gaaatttcgg tattcagata ttttgggcat    900
gaacatatgc caggaagcgt tgaaatcaag ctgaggatac ttatggatga gctgaatccg    960
taa                                                                   963

<210> SEQ ID NO 12
<211> LENGTH: 320
<212> TYPE: PRT
<213> ORGANISM: Clostridium thermocellum

<400> SEQUENCE: 12

Met Ala Gln Leu Tyr Asp Met Pro Leu Glu Glu Leu Lys Lys Tyr Lys
1               5                   10                  15

Pro Ala Leu Thr Lys Gln Lys Asp Phe Asp Glu Phe Trp Glu Lys Ser
            20                  25                  30

Leu Lys Glu Leu Ala Glu Ile Pro Leu Lys Tyr Gln Leu Ile Pro Tyr
        35                  40                  45

Asp Phe Pro Ala Arg Arg Val Lys Val Phe Arg Val Glu Tyr Leu Gly
    50                  55                  60

Phe Lys Gly Ala Asn Ile Glu Gly Trp Leu Ala Val Pro Glu Gly Glu
65                  70                  75                  80

Gly Leu Tyr Pro Gly Leu Val Gln Phe His Gly Tyr Asn Trp Ala Met
                85                  90                  95

Asp Gly Cys Val Pro Asp Val Val Asn Trp Ala Leu Asn Gly Tyr Ala
            100                 105                 110

Ala Phe Leu Met Leu Val Arg Gly Gln Gln Gly Arg Ser Val Asp Asn
        115                 120                 125

Ile Val Pro Gly Ser Gly His Ala Leu Gly Trp Met Ser Lys Gly Ile
    130                 135                 140

Leu Ser Pro Glu Glu Tyr Tyr Tyr Arg Gly Val Tyr Met Asp Ala Val
145                 150                 155                 160

Arg Ala Val Glu Ile Leu Ala Ser Leu Pro Cys Val Asp Glu Ser Arg
                165                 170                 175

Ile Gly Val Thr Gly Gly Ser Gln Gly Gly Gly Leu Ala Leu Ala Val
            180                 185                 190

Ala Ala Leu Ser Gly Ile Pro Lys Val Ala Ala Val His Tyr Pro Phe
        195                 200                 205

Leu Ala His Phe Glu Arg Ala Ile Asp Val Ala Pro Asp Gly Pro Tyr
    210                 215                 220

Leu Glu Ile Asn Glu Tyr Leu Arg Arg Asn Ser Gly Glu Glu Ile Glu
225                 230                 235                 240
```

```
Arg Gln Val Lys Lys Thr Leu Ser Tyr Phe Asp Ile Met Asn Leu Ala
            245                 250                 255

Pro Arg Ile Lys Cys Arg Thr Trp Ile Cys Thr Gly Leu Val Asp Glu
        260                 265                 270

Ile Thr Pro Pro Ser Thr Val Phe Ala Val Tyr Asn His Leu Lys Cys
        275                 280                 285

Pro Lys Glu Ile Ser Val Phe Arg Tyr Phe Gly His Glu His Met Pro
        290                 295                 300

Gly Ser Val Glu Ile Lys Leu Arg Ile Leu Met Asp Glu Leu Asn Pro
305                 310                 315                 320
```

<210> SEQ ID NO 13
<211> LENGTH: 978
<212> TYPE: DNA
<213> ORGANISM: Thermotoga neapolitana

<400> SEQUENCE: 13

```
atggccttct tcgatatgcc ccttgaggaa ctgaaaaagt accggcctga aaggtacgag      60
gagaaagatt tcgatgagtt ctggagggaa acacttaaag aaagcgaagg attccctctg     120
gatcccgtct ttgaaaaggt ggactttcat ctcaaaacgg ttgaaacgta cgatgttact     180
ttctctggat acagggggca gagaataaag ggctggcttc ttgttccgaa gttggcggaa     240
gaaaagcttc catgcgtcgt gcagtacata ggttacaatg gtggaagggg ttttccacac     300
gactggctgt tctggccgtc aatgggttac atctgttttg tcatggacac caggggcag      360
ggaagcggct ggatgaaggg agacacaccg gattaccctg aggtccagt cgatccacag      420
taccccggat tcatgacgag gggcattctg gatccgggaa cctattacta caggcgagtc     480
ttcgtggatg cggtcagggc ggtggaagca gccatttcct tcccgagagt ggattccagg     540
aaggtggtgg tggccggagg cagtcagggt gggggaatcg cccttgcggt gagtgccctg     600
tcgaacaggt gaaggctct gctctgcgat gtgccgtttc tgtgccactt cagaagggcc      660
gtgcaacttg tcgacacaca cccatacgtg gagatcacca acttcctcaa acccacagg      720
gacaaagagg agattgttt cagaacactt tcctacttcg atggtgtgaa ctttgcagca     780
agggcaaagg tgcccgccct gttttccgtt gggctcatgg acaccatctg tcctccctcg     840
acggtcttcg ccgcttacaa ccactacgcc ggtccaaagg agatcagaat ctatccgtac     900
aacaaccacg aaggtggagg ttcttttccag gcaattgagc aggtgaaatt cttgaagaga     960
ctatttgagg aaggctag                                                   978
```

<210> SEQ ID NO 14
<211> LENGTH: 325
<212> TYPE: PRT
<213> ORGANISM: Thermotoga neapolitana

<400> SEQUENCE: 14

```
Met Ala Phe Phe Asp Met Pro Leu Glu Glu Leu Lys Lys Tyr Arg Pro
1               5                   10                  15

Glu Arg Tyr Glu Glu Lys Asp Phe Asp Glu Phe Trp Arg Glu Thr Leu
            20                  25                  30

Lys Glu Ser Glu Gly Phe Pro Leu Asp Pro Val Phe Glu Lys Val Asp
        35                  40                  45

Phe His Leu Lys Thr Val Glu Thr Tyr Asp Val Thr Phe Ser Gly Tyr
    50                  55                  60

Arg Gly Gln Arg Ile Lys Gly Trp Leu Leu Val Pro Lys Leu Ala Glu
65                  70                  75                  80
```

-continued

```
Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Gly Thr Tyr Tyr Arg Arg Val
145                 150                 155                 160

Phe Val Asp Ala Val Arg Ala Val Glu Ala Ala Ile Ser Phe Pro Arg
                165                 170                 175

Val Asp Ser Arg Lys Val Val Val Ala Gly Gly Ser Gln Gly Gly Gly
            180                 185                 190

Ile Ala Leu Ala Val Ser Ala Leu Ser Asn Arg Val Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Val Pro Ala Leu Phe Ser Val Gly Leu
            260                 265                 270

Met Asp Thr Ile Cys Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Glu Gly
            325
```

```
<210> SEQ ID NO 15
<211> LENGTH: 978
<212> TYPE: DNA
<213> ORGANISM: Thermotoga maritima

<400> SEQUENCE: 15
atggccttct tcgatttacc actcgaagaa ctgaagaaat atcgtccaga gcggtacgaa      60
gagaaagact tcgatgagtt ctgggaagag acactcgcag agagcgaaaa gttcccctta     120
gaccccgtct tcgagaggat ggagtctcac ctcaaaacag tcgaagcgta cgatgtcacc     180
ttctccggat acagggcaca gaggatcaaa gggtggctcc ttgttccaaa actggaagaa     240
gaaaaacttc cctgcgttgt gcagtacata ggatacaacg gtggaagagg attccctcac     300
gactggctgt tctggccttc tatgggttac atatgtttcg tcatggatac tcgaggtcag     360
ggaagcggct ggctgaaagg agacacaccg gattaccctg agggtcccgt tgaccctcag     420
tatccaggat tcatgacaag aggaatactg gatcccagaa cttactacta gagacgagtc     480 ttcacgacg ctgtcagagc cgttgaagct gctgcttctt ttcctcaggt agatcaagaa     540
agaatcgtga tagctggagg cagtcagggt ggcggaatag cccttgcggt gagcgctctc     600
tcaaagaaag caaaggctct tctgtgcgat gtgccgtttc tgtgtcactt cagaagagca     660
gtacagcttg tggatacgca tccatacgcg gagatcacga actttctaaa gacccacaga     720
```

```
gacaaggaag aaatcgtgtt caggactctt tcctatttcg atggagtgaa cttcgcagcc    780
agagcgaaga tccctgcgct gttttctgtg ggtctcatgg acaacatttg tcctccttca    840
acggttttcg ctgcctacaa ttactacgct ggaccgaagg aaatcagaat ctatccgtac    900
aacaaccacg agggaggagg ctctttccaa gcggttgaac aggtgaaatt cttgaaaaaa    960
ctatttgaga aaggctaa                                                  978
```

<210> SEQ ID NO 16
<211> LENGTH: 325
<212> TYPE: PRT
<213> ORGANISM: Thermotoga maritima

<400> SEQUENCE: 16

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Cys Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
            325
```

<210> SEQ ID NO 17
<211> LENGTH: 963
<212> TYPE: DNA
<213> ORGANISM: Thermoanaerobacterium sp.

<400> SEQUENCE: 17

```
atgggacttt tcgacatgcc attacaaaaa cttagagaat acactggtac aaatccatgc      60
cctgaagatt tcgatgagta ttggaatagg gctttagatg agatgaggtc agttgatcct     120
aaaattgaat tgaaagaaag tagctttcaa gtatcctttg cagaatgcta tgacttgtac     180
tttacaggtg ttcgtggtgc cagaattcat gcaaagtata taaaacctaa gacagaaggg     240
aaacatccag cgttgataag atttcatgga tattcgtcaa attcaggcga ctggaacgac     300
aaattaaatt acgtggcggc aggcttcacc gttgtggcta tggatgtaag aggtcaagga     360
gggcagtctc aagatgttgg cggtgtaact gggaatactt taaatgggca tattataaga     420
gggctagacg atgatgctga taatatgctt ttcaggcata ttttcttaga cactgcccaa     480
ttggctggaa tagttatgaa catgccagaa gttgatgaag atagagtggg agtcatggga     540
ccttctcaag gcggagggct gtcgttggcg tgtgctgcat ggagccaag ggtacgcaaa      600
gtagtatctg aatatccttt tttatctgac tacaagagag tttgggactt agaccttgca     660
aaaaacgcct atcaagagat tacgactat tcaggcttt tgacccaag gcatgaaagg        720
gagaatgagg tatttacaaa gcttggatat atagacgtta aaaaccttgc gaaaaggata     780
aaaggcgatg tcttaatgtg cgttgggctt atggaccaag tatgtccgcc atcaactgtt     840
tttgcagcct acaacaacat acagtcaaaa aagatataa aagtgtatcc tgattatgga      900
catgaaccta tgagaggatt tggagattta gcgatgcagt ttatgttgga actatattca     960
taa                                                                     963
```

<210> SEQ ID NO 18
<211> LENGTH: 320
<212> TYPE: PRT
<213> ORGANISM: Thermoanaerobacterium sp.

<400> SEQUENCE: 18

```
Met Gly Leu Phe Asp Met Pro Leu Gln Lys Leu Arg Glu Tyr Thr Gly
1               5                   10                  15

Thr Asn Pro Cys Pro Glu Asp Phe Asp Glu Tyr Trp Asn Arg Ala Leu
            20                  25                  30

Asp Glu Met Arg Ser Val Asp Pro Lys Ile Glu Leu Lys Glu Ser Ser
        35                  40                  45

Phe Gln Val Ser Phe Ala Glu Cys Tyr Asp Leu Tyr Phe Thr Gly Val
    50                  55                  60

Arg Gly Ala Arg Ile His Ala Lys Tyr Ile Lys Pro Lys Thr Glu Gly
65                  70                  75                  80

Lys His Pro Ala Leu Ile Arg Phe His Gly Tyr Ser Ser Asn Ser Gly
                85                  90                  95

Asp Trp Asn Asp Lys Leu Asn Tyr Val Ala Ala Gly Phe Thr Val Val
            100                 105                 110

Ala Met Asp Val Arg Gly Gln Gly Gly Gln Ser Gln Asp Val Gly Gly
        115                 120                 125

Val Thr Gly Asn Thr Leu Asn Gly His Ile Ile Arg Gly Leu Asp Asp
    130                 135                 140

Asp Ala Asp Asn Met Leu Phe Arg His Ile Phe Leu Asp Thr Ala Gln
145                 150                 155                 160
```

-continued

```
Leu Ala Gly Ile Val Met Asn Met Pro Glu Val Asp Glu Asp Arg Val
                165                 170                 175
Gly Val Met Gly Pro Ser Gln Gly Gly Leu Ser Leu Ala Cys Ala
        180                 185                 190
Ala Leu Glu Pro Arg Val Arg Lys Val Val Ser Glu Tyr Pro Phe Leu
            195                 200                 205
Ser Asp Tyr Lys Arg Val Trp Asp Leu Asp Leu Ala Lys Asn Ala Tyr
210                 215                 220
Gln Glu Ile Thr Asp Tyr Phe Arg Leu Phe Asp Pro Arg His Glu Arg
225                 230                 235                 240
Glu Asn Glu Val Phe Thr Lys Leu Gly Tyr Ile Asp Val Lys Asn Leu
                245                 250                 255
Ala Lys Arg Ile Lys Gly Asp Val Leu Met Cys Val Gly Leu Met Asp
            260                 265                 270
Gln Val Cys Pro Pro Ser Thr Val Phe Ala Ala Tyr Asn Asn Ile Gln
        275                 280                 285
Ser Lys Lys Asp Ile Lys Val Tyr Pro Asp Tyr Gly His Glu Pro Met
    290                 295                 300
Arg Gly Phe Gly Asp Leu Ala Met Gln Phe Met Leu Glu Leu Tyr Ser
305                 310                 315                 320
```

<210> SEQ ID NO 19
<211> LENGTH: 1023
<212> TYPE: DNA
<213> ORGANISM: Bacillus sp.

<400> SEQUENCE: 19

```
atgaggacgg ttcctgctcc tgttttttg gagaggagtg gggagatgaa ccttttgat      60
atgccccttg aggagctgca gcattacaag cctgcccaga ccaggcagga tgattttgag    120
tcattctgga aaaagcggat tgaggagaac agtcaatatc cgctgaatat agaagtaatg    180
gagcgggttt atccggttcc gggagtgaga gtatatgata tttattttga cgggttccgg    240
aattcccgca tccatggggt gtatgttact ccagaaactc cgggagcgga cactcctgcg    300
gcagtgattt tcacggcta taactggaac acgctgcagc cgcattacag cttcaagcac    360
gtgattcagg ggattcctgt actgatggtg gaggtgcggg acaaaatct cttgtctcca    420
gatagaaatc attatgggaa tggaggtccg ggaggctgga tgacactcgg cgtgatggat    480
cccgatcaat attattacag cctggtatat atggactgct ccgcagcat tgatgctgtc     540
agggaactgt cgaggaagag aagtgtgttt gtggaaggcg aaagccaggg aggtgcactg    600
gcgattgccg cagccgccct gcaggatgac atcctgcttg cactcgccga catccctttt    660
ctcacccatt tcaagcgttc cgtggagctt tcctcggatg accgtatca ggagatttcc     720
cactacttca agttcatga tcctcttcat caaacggaag agcaggtata tcagacgctc    780
agctatgtgg actgcatgaa catggccagc atggttgaat gtccagtcct tctttcagcc    840
ggtctggaag acatcgtttg tcccccgtcc agtgcatttg cactgttcaa ccatctcggc    900
gggccaaaag aaatacgggc ctatccggaa tacgcccatg aagtaccggc tgtccatgaa    960
gaggaaaagc tgaagtttat atcttcaagg ctaaaaaata gagaaaagag gtgccggcca   1020
tga                                                                 1023
```

<210> SEQ ID NO 20
<211> LENGTH: 340
<212> TYPE: PRT
<213> ORGANISM: Bacillus sp.

<400> SEQUENCE: 20

```
Met Arg Thr Val Pro Ala Pro Val Phe Leu Glu Arg Ser Gly Glu Met
1               5                   10                  15

Asn Leu Phe Asp Met Pro Leu Glu Glu Leu Gln His Tyr Lys Pro Ala
            20                  25                  30

Gln Thr Arg Gln Asp Asp Phe Glu Ser Phe Trp Lys Lys Arg Ile Glu
        35                  40                  45

Glu Asn Ser Gln Tyr Pro Leu Asn Ile Glu Val Met Glu Arg Val Tyr
    50                  55                  60

Pro Val Pro Gly Val Arg Val Tyr Asp Ile Tyr Phe Asp Gly Phe Arg
65                  70                  75                  80

Asn Ser Arg Ile His Gly Val Tyr Val Thr Pro Glu Thr Pro Gly Ala
                85                  90                  95

Asp Thr Pro Ala Ala Val Ile Phe His Gly Tyr Asn Trp Asn Thr Leu
            100                 105                 110

Gln Pro His Tyr Ser Phe Lys His Val Ile Gln Gly Ile Pro Val Leu
        115                 120                 125

Met Val Glu Val Arg Gly Gln Asn Leu Leu Ser Pro Asp Arg Asn His
130                 135                 140

Tyr Gly Asn Gly Gly Pro Gly Gly Trp Met Thr Leu Gly Val Met Asp
145                 150                 155                 160

Pro Asp Gln Tyr Tyr Tyr Ser Leu Val Tyr Met Asp Cys Phe Arg Ser
                165                 170                 175

Ile Asp Ala Val Arg Glu Leu Ser Arg Lys Arg Ser Val Phe Val Glu
            180                 185                 190

Gly Gly Ser Gln Gly Gly Ala Leu Ala Ile Ala Ala Ala Leu Gln
        195                 200                 205

Asp Asp Ile Leu Leu Ala Leu Ala Asp Ile Pro Phe Leu Thr His Phe
    210                 215                 220

Lys Arg Ser Val Glu Leu Ser Ser Asp Gly Pro Tyr Gln Glu Ile Ser
225                 230                 235                 240

His Tyr Phe Lys Val His Asp Pro Leu His Gln Thr Glu Glu Gln Val
                245                 250                 255

Tyr Gln Thr Leu Ser Tyr Val Asp Cys Met Asn Met Ala Ser Met Val
            260                 265                 270

Glu Cys Pro Val Leu Leu Ser Ala Gly Leu Glu Asp Ile Val Cys Pro
        275                 280                 285

Pro Ser Ser Ala Phe Ala Leu Phe Asn His Leu Gly Gly Pro Lys Glu
    290                 295                 300

Ile Arg Ala Tyr Pro Glu Tyr Ala His Glu Val Pro Ala Val His Glu
305                 310                 315                 320

Glu Glu Lys Leu Lys Phe Ile Ser Ser Arg Leu Lys Asn Arg Glu Lys
                325                 330                 335

Arg Cys Arg Pro
            340
```

<210> SEQ ID NO 21
<211> LENGTH: 960
<212> TYPE: DNA
<213> ORGANISM: Bacillus halodurans

<400> SEQUENCE: 21

```
ttagagatca gataaaaatt gaaaaatccg atcacgatgg cctggcaaat cttcgtgagc      60
aaagtctgga tataactcga tacttttgt  cgtcgtgagt ttgttataca tggcaaattg     120
```

```
tgtagacggc gggcaaaccg tatccattaa cccaacagca agtaagactt ctcccttttac    180 gagtggagca agatgctgaa tatcaatata gcctagcttc gtaaagattt cagcctcacg    240
tcggtgctgt ggatcaaagc gacgaaaata cgtttgcaat tcgtcataag ctttctcggc    300
taaatccatc tcccatacgc gttggtaatc gctaaggaaa ggataaacag gagctacctt    360 tttaatttc ggttccaaag ccgcacaagc aatcgctaag gcccctcctt gtgaccaacc     420
tgtcactgcc acgcgctctt catcgacttc aggaaggttc atcacaatgt tggcaagctg    480
agccgtatca agaaacacat gacggaacaa taattgatca gcattatcat cgagtccgcg    540
tattatatga ccggaatgag tattcccctt cacgcctcct gtgtcttcag acaagcctcc    600
ttgcccgcga acgtccattg caagaacaga atatccgagg gctgcgtaat gaagtaaacc    660
cgtccattcc cccgcattca tcgtatatcc gtgaaaatga ataaccgccg ggtgtgtccc    720
gctcgtgtgt cttgggcgca cgtatttgc gtgaattcta gcaccccaa cccctgtaaa    780 atataggtgg aagcattctg catacgtggt ttgaaaatca ctcggtatga gctctacgtt    840
tggatttacc tttctcatct cttgtaaagc acgatcccaa tactcagtaa agtcatctgg    900
ctttggatta cgtcccatgt actcttttaa ttcggttaac ggcatgtcta ttagtggcat    960
```

<210> SEQ ID NO 22
<211> LENGTH: 319
<212> TYPE: PRT
<213> ORGANISM: Bacillus halodurans

<400> SEQUENCE: 22

```
Met Pro Leu Ile Asp Met Pro Leu Thr Glu Leu Lys Glu Tyr Met Gly
1               5                   10                  15

Arg Asn Pro Lys Pro Asp Asp Phe Thr Glu Tyr Trp Asp Arg Ala Leu
            20                  25                  30

Gln Glu Met Arg Lys Val Asn Pro Asn Val Glu Leu Ile Pro Ser Asp
        35                  40                  45

Phe Gln Thr Thr Tyr Ala Glu Cys Phe His Leu Tyr Phe Thr Gly Val
    50                  55                  60

Arg Gly Ala Arg Ile His Ala Lys Tyr Val Arg Pro Arg His Thr Ser
65                  70                  75                  80

Gly Thr His Pro Ala Val Ile Phe His Gly Tyr Thr Met Asn Ala
                85                  90                  95

Gly Glu Trp Thr Gly Leu Leu His Tyr Ala Ala Leu Gly Tyr Ser Val
                100                 105                 110

Leu Ala Met Asp Val Arg Gly Gln Gly Gly Leu Ser Glu Asp Thr Gly
        115                 120                 125

Gly Val Lys Gly Asn Thr His Ser Gly His Ile Ile Arg Gly Leu Asp
    130                 135                 140

Asp Asn Ala Asp Gln Leu Leu Phe Arg His Val Phe Leu Asp Thr Ala
145                 150                 155                 160

Gln Leu Ala Asn Ile Val Met Asn Leu Pro Glu Val Asp Glu Glu Arg
                165                 170                 175

Val Ala Val Thr Gly Trp Ser Gln Gly Gly Ala Leu Ala Ile Ala Cys
            180                 185                 190

Ala Ala Leu Glu Pro Lys Ile Lys Lys Val Ala Pro Val Tyr Pro Phe
        195                 200                 205

Leu Ser Asp Tyr Gln Arg Val Trp Glu Met Asp Leu Ala Glu Lys Ala
    210                 215                 220

Tyr Asp Glu Leu Gln Thr Tyr Phe Arg Arg Phe Asp Pro Gln His Arg
```

```
                    225                 230                 235                 240
Arg Glu Ala Glu Ile Phe Thr Lys Leu Gly Tyr Ile Asp Ile Gln His
                245                 250                 255
Leu Ala Pro Leu Val Lys Gly Glu Val Leu Ala Val Gly Leu Met
            260                 265                 270
Asp Thr Val Cys Pro Pro Ser Thr Gln Phe Ala Met Tyr Asn Lys Leu
        275                 280                 285
Thr Thr Thr Lys Ser Ile Glu Leu Tyr Pro Asp Phe Ala His Glu Asp
    290                 295                 300
Leu Pro Gly His Arg Asp Arg Ile Phe Gln Phe Leu Ser Asp Leu
305                 310                 315

<210> SEQ ID NO 23
<211> LENGTH: 954
<212> TYPE: DNA
<213> ORGANISM: Bacillus clausii

<400> SEQUENCE: 23
atgccattag tcgatatgcc gttgcgcgag ttgttagctt atgaaggaat aaaccctaaa      60
ccagcagatt ttgaccaata ctggaaccgg gccaaaacgg aaattgaagc gattgatccc     120
gaagtcactc tagtcgaatc ttcttttccag tgttcgtttg caaactgtta ccatttctat     180
tatcgaagcg ctgaaaatgc aaaaatccat gcgaaatacg tacagccaaa agcaggggag     240
aagacgccag cagtttttat gttccatggg tatgggggc gttcagccga atggagcagc     300
ttgttaaatt atgtagcggc gggttttct gttttctata tggacgtgcg tggacaaggt     360
ggaacttcag aggatcctgg gggcgtaagg gggaatacat ataggggcca cattattcgc     420
ggcctcgatg ccgggccaga cgcactttt taccgcagcg ttttcttgga caccgtccaa     480
ttggttcgtg ctgctaaaac attgcctcac atcgataaaa cacggcttat ggccacaggg     540
tggtcgcaag ggggcgcctt aacgcttgcc tgtgctgccc ttgttcctga atcaagcgt      600 cttgctccag tatacccgtt tttaagcgat tacaagcgag tgtggcaaat ggatttagcg     660
gttcgttcgt ataaagaatt ggctgattat ttccgttcat acgatccgca acataaacgc     720
catggcgaaa tttttgaacg ccttggctac atcgatgtcc agcatcttgc tgaccggatt     780
caaggagatg tcctaatggg agttggttta tggatacag aatgcccgcc gtctacccaa     840
tttgctgctt ataataaaat aaaggctaaa aaatcgtatg agctctatcc tgattttggc     900
catgagcacc ttccaggaat gaacgatcat atttttcgct ttttcactag ttga           954

<210> SEQ ID NO 24
<211> LENGTH: 317
<212> TYPE: PRT
<213> ORGANISM: Bacillus clausii

<400> SEQUENCE: 24

Met Pro Leu Val Asp Met Pro Leu Arg Glu Leu Ala Tyr Glu Gly
1               5                   10                  15

Ile Asn Pro Lys Pro Ala Asp Phe Asp Gln Tyr Trp Asn Arg Ala Lys
            20                  25                  30

Thr Glu Ile Glu Ala Ile Asp Pro Glu Val Thr Leu Val Glu Ser Ser
        35                  40                  45

Phe Gln Cys Ser Phe Ala Asn Cys Tyr His Phe Tyr Arg Ser Ala
    50                  55                  60

Gly Asn Ala Lys Ile His Ala Lys Tyr Val Gln Pro Lys Ala Gly Glu
65                  70                  75                  80
```

```
Lys Thr Pro Ala Val Phe Met Phe His Gly Tyr Gly Arg Ser Ala
                85                  90                  95

Glu Trp Ser Ser Leu Leu Asn Tyr Val Ala Ala Gly Phe Ser Val Phe
            100                 105                 110

Tyr Met Asp Val Arg Gly Gln Gly Thr Ser Glu Asp Pro Gly Gly
        115                 120                 125

Val Arg Gly Asn Thr Tyr Arg Gly His Ile Ile Arg Gly Leu Asp Ala
    130                 135                 140

Gly Pro Asp Ala Leu Phe Tyr Arg Ser Val Phe Leu Asp Thr Val Gln
145                 150                 155                 160

Leu Val Arg Ala Ala Lys Thr Leu Pro His Ile Asp Lys Thr Arg Leu
                165                 170                 175

Met Ala Thr Gly Trp Ser Gln Gly Gly Ala Leu Thr Leu Ala Cys Ala
            180                 185                 190

Ala Leu Val Pro Glu Ile Lys Arg Leu Ala Pro Val Tyr Pro Phe Leu
        195                 200                 205

Ser Asp Tyr Lys Arg Val Trp Gln Met Asp Leu Ala Val Arg Ser Tyr
    210                 215                 220

Lys Glu Leu Ala Asp Tyr Phe Arg Ser Tyr Asp Pro Gln His Lys Arg
225                 230                 235                 240

His Gly Glu Ile Phe Glu Arg Leu Gly Tyr Ile Asp Val Gln His Leu
                245                 250                 255

Ala Asp Arg Ile Gln Gly Asp Val Leu Met Gly Val Gly Leu Met Asp
            260                 265                 270

Thr Glu Cys Pro Pro Ser Thr Gln Phe Ala Ala Tyr Asn Lys Ile Lys
        275                 280                 285

Ala Lys Lys Ser Tyr Glu Leu Tyr Pro Asp Phe Gly His Glu His Leu
    290                 295                 300

Pro Gly Met Asn Asp His Ile Phe Arg Phe Phe Thr Ser
305                 310                 315

<210> SEQ ID NO 25
<211> LENGTH: 49
<212> TYPE: DNA
<213> ORGANISM: Artificial Sequence
<220> FEATURE:
<223> OTHER INFORMATION: Primer

<400> SEQUENCE: 25
taactgcagt aaggaggaat aggacatgca actattcgat ctgccgctc              49

<210> SEQ ID NO 26
<211> LENGTH: 35
<212> TYPE: DNA
<213> ORGANISM: Artificial Sequence
<220> FEATURE:
<223> OTHER INFORMATION: Primer

<400> SEQUENCE: 26
tgatctagat tatcagcctt taagatgctg cttaa                             35

<210> SEQ ID NO 27
<211> LENGTH: 994
<212> TYPE: DNA
<213> ORGANISM: Artificial Sequence
<220> FEATURE:
<223> OTHER INFORMATION: Synthetic construct

<400> SEQUENCE: 27
taactgcagt aaggaggaat aggacatgca actattcgat ctgccgctcg accaattgca   60
```

```
aacatatatag cctgaaaaaa cagcaccgaa agattttttct gagttttgga aattgtcttt      120
ggaggaactt gcaaaagtcc aagcagaacc tgatttacag ccggttgact atcctgctga      180
cggagtaaaa gtgtaccgtc tcacatataa aagcttcgga aacgcccgca ttaccggatg      240
gtacgcggtg cctgacaagc aaggcccgca tccggcgatc gtgaaatatc atggctacaa      300
tgcaagctat gatggtgaga ttcatgaaat ggtaaactgg gcactccatg gctacgccgc      360
attcggcatg cttgtccgcg ccagcagag cagcgaggat acgagtattt cactgcacgg       420
tcacgctttg ggctggatga cgaaaggaat tcttgataaa gatacatact attaccgcgg      480
tgtttatttg gacgccgtcc gcgcgcttga ggtcatcagc agcttcgacg aggttgacga      540
aacaaggatc ggtgtgacag gaggaagcca aggcggaggt ttaaccattg ccgcagcagc      600
gctgtcagac attccaaaag ccgcggttgc cgattatcct tatttaagca acttcgaacg      660
ggccattgat gtggcgcttg aacagccgta ccttgaaatc aattccttct tcagaagaaa      720
tggcagcccg gaaacagaag tgcaggcgat gaagacactt tcatatttcg atattatgaa      780
tctcgctgac cgagtgaagg tgcctgtcct gatgtcaatc ggcctgattg acaaggtcac      840
gccgccgtcc accgtgtttg ccgcctacaa tcatttggaa acagagaaag agctgaaggt      900
gtaccgctac ttcggacatg agtatatccc tgcttttcaa acggaaaaac ttgctttctt      960
taagcagcat cttaaaggct gataatctag atca                                  994

<210> SEQ ID NO 28
<211> LENGTH: 994
<212> TYPE: DNA
<213> ORGANISM: Artificial Sequence
<220> FEATURE:
<223> OTHER INFORMATION: Synthetic construct

<400> SEQUENCE: 28
taactgcagt aaggaggaat aggacatgca actattcgat ctgccgctcg accaattgca       60 aacatatatag cctgaaaaaa cagcaccgaa agattttttct gagttttgga aattgtcttt    120
ggaggaactt gcaaaagtcc aagcagaacc tgatttacag ccggttgact atcctgctga      180
cggagtaaaa gtgtaccgtc tcacatataa aagcttcgga aacgcccgca ttaccggatg      240
gtacgcggtg cctgacaagg aaggcccgca tccggcgatc gtgaaatatc atggctacaa      300
tgcaagctat gatggtgaga ttcatgaaat ggtaaactgg gcactccatg gctacgccac      360
attcggcatg cttgtccgcg ccagcagag cagcgaggat acgagtattt caccgcacgg       420
tcacgctttg ggctggatga cgaaaggaat tcttgataaa gatacatact attaccgcgg      480
tgtttatttg gacgccgtcc gcgcgcttga ggtcatcagc agcttcgacg aggttgacga      540
aacaaggatc ggtgtgacag gaggaagcca aggcggaggt ttaaccattg ccgcagcagc      600
gctgtcagac attccaaaag ccgcggttgc cgattatcct tatttaagca acttcgaacg      660
ggccattgat gtggcgcttg aacagccgta ccttgaaatc aattccttct tcagaagaaa      720
tggcagcccg gaaacagaag tgcaggcgat gaagacactt tcatatttcg atattatgaa      780
tctcgctgac cgagtgaagg tgcctgtcct gatgtcaatc ggcctgattg acaaggtcac      840
gccgccgtcc accgtgtttg ccgcctacaa tcatttggaa acaagaaaag agctgaaggt      900
gtaccgctac ttcggacatg agtatatccc tgcttttcaa actgaaaaac ttgctttctt      960
taagcagcat cttaaaggct gataatctag atca                                  994

<210> SEQ ID NO 29
<211> LENGTH: 960
```

```
<212> TYPE: DNA
<213> ORGANISM: Bacillus subtilis
<220> FEATURE:
<221> NAME/KEY: CDS
<222> LOCATION: (1)..(960)

<400> SEQUENCE: 29 atg caa cta ttc gat ctg ccg ctc gac caa ttg caa aca tat aag cct      48
Met Gln Leu Phe Asp Leu Pro Leu Asp Gln Leu Gln Thr Tyr Lys Pro
1               5                   10                  15 gaa aaa aca gca ccg aaa gat ttt tct gag ttt tgg aaa ttg tct ttg      96
Glu Lys Thr Ala Pro Lys Asp Phe Ser Glu Phe Trp Lys Leu Ser Leu
            20                  25                  30 gag gaa ctt gca aaa gtc caa gca gaa cct gat cta cag ccg gtt gac     144
Glu Glu Leu Ala Lys Val Gln Ala Glu Pro Asp Leu Gln Pro Val Asp
        35                  40                  45 tat cct gct gac gga gta aaa gtg tac cgt ctc aca tat aaa agc ttc     192
Tyr Pro Ala Asp Gly Val Lys Val Tyr Arg Leu Thr Tyr Lys Ser Phe
    50                  55                  60 gga aac gcc cgc att acc gga tgg tac gcg gtg cct gac aag caa ggc     240
Gly Asn Ala Arg Ile Thr Gly Trp Tyr Ala Val Pro Asp Lys Gln Gly
65                  70                  75                  80 ccg cat ccg gcg atc gtg aaa tat cat ggc tac aat gca agc tat gat     288
Pro His Pro Ala Ile Val Lys Tyr His Gly Tyr Asn Ala Ser Tyr Asp
                85                  90                  95 ggt gag att cat gaa atg gta aac tgg gca ctc cat ggc tac gcc gca     336
Gly Glu Ile His Glu Met Val Asn Trp Ala Leu His Gly Tyr Ala Ala
            100                 105                 110 ttc ggc atg ctt gtc cgc ggc cag cag agc agc gag gat acg agt att     384
Phe Gly Met Leu Val Arg Gly Gln Gln Ser Ser Glu Asp Thr Ser Ile
        115                 120                 125 tca ccg cac ggt cac gct ttg ggc tgg atg acg aaa gga att ctt gat     432
Ser Pro His Gly His Ala Leu Gly Trp Met Thr Lys Gly Ile Leu Asp
    130                 135                 140 aaa gat aca tac tat tac cgc ggt gtt tat ttg gac gcc gtc cgc gcg     480
Lys Asp Thr Tyr Tyr Tyr Arg Gly Val Tyr Leu Asp Ala Val Arg Ala
145                 150                 155                 160 ctt gag gtc atc agc agc ttc gac gag gtt gac gaa aca agg atc ggt     528
Leu Glu Val Ile Ser Ser Phe Asp Glu Val Asp Glu Thr Arg Ile Gly
                165                 170                 175 gtg aca gga gga agc caa ggc gga ggt tta acc att gcc gca gca gcg     576
Val Thr Gly Gly Ser Gln Gly Gly Gly Leu Thr Ile Ala Ala Ala Ala
            180                 185                 190 ctg tca gac att cca aaa gcc gcg gtt gcc gat tat cct tat tta agc     624
Leu Ser Asp Ile Pro Lys Ala Ala Val Ala Asp Tyr Pro Tyr Leu Ser
        195                 200                 205 aac ttc gaa cgg gcc att gat gtg gcg ctt gaa cag ccg tac ctt gaa     672
Asn Phe Glu Arg Ala Ile Asp Val Ala Leu Glu Gln Pro Tyr Leu Glu
    210                 215                 220 atc aat tcc ttc ttc aga aga aat ggc agc ccg gaa aca gaa gtg cag     720
Ile Asn Ser Phe Phe Arg Arg Asn Gly Ser Pro Glu Thr Glu Val Gln
225                 230                 235                 240 gcg atg aag aca ctt tca tat ttc gat att atg aat ctc gct gac cga     768
Ala Met Lys Thr Leu Ser Tyr Phe Asp Ile Met Asn Leu Ala Asp Arg
                245                 250                 255 gtg aag gtg cct gtc ctg atg tca atc ggc ctg att gac aag gtc acg     816
Val Lys Val Pro Val Leu Met Ser Ile Gly Leu Ile Asp Lys Val Thr
            260                 265                 270 ccg cca tcc acc gtg ttt gcc gcc tac aat cat ttg gaa aca gag aaa     864
Pro Pro Ser Thr Val Phe Ala Ala Tyr Asn His Leu Glu Thr Glu Lys
        275                 280                 285
```

```
gag ctg aag gtg tac cgc tac ttc gga cat gag tat atc cct gct ttt    912
Glu Leu Lys Val Tyr Arg Tyr Phe Gly His Glu Tyr Ile Pro Ala Phe
    290             295                 300 caa acg gaa aaa ctt gct ttc ttt aag cag cat ctt aaa ggc tga taa    960
Gln Thr Glu Lys Leu Ala Phe Phe Lys Gln His Leu Lys Gly
305                 310                 315
```

<210> SEQ ID NO 30
<211> LENGTH: 318
<212> TYPE: PRT
<213> ORGANISM: Bacillus subtilis

<400> SEQUENCE: 30

```
Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Gln Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Pro His Gly His Ala Leu Gly Trp Met Thr Lys Gly Ile Leu Asp
    130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
        275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315
```

<210> SEQ ID NO 31
<211> LENGTH: 24
<212> TYPE: DNA

<210> SEQ ID NO 31
<211> LENGTH: 24
<212> TYPE: DNA
<213> ORGANISM: Artificial Sequence
<220> FEATURE:
<223> OTHER INFORMATION: Primer

<400> SEQUENCE: 31
atgcagcagc cttatgatgt gccg					24

<210> SEQ ID NO 32
<211> LENGTH: 25
<212> TYPE: DNA
<213> ORGANISM: Artificial Sequence
<220> FEATURE:
<223> OTHER INFORMATION: Primer

<400> SEQUENCE: 32
ttatttcaga tgctttctca gaaac					25

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
atgcagctgt ttgacctgag cctg					24

<210> SEQ ID NO 34
<211> LENGTH: 27
<212> TYPE: DNA
<213> ORGANISM: Artificial Sequence
<220> FEATURE:
<223> OTHER INFORMATION: Primer

<400> SEQUENCE: 34
ttaggtggac agcagcaggt gcttttg					27

<210> SEQ ID NO 35
<211> LENGTH: 795
<212> TYPE: DNA
<213> ORGANISM: Artificial Sequence
<220> FEATURE:
<223> OTHER INFORMATION: Primer

<400> SEQUENCE: 35

| | | |
|---|---|---|
| atgattgaac aagatggatt gcacgcaggt tctccggccg cttgggtgga gaggctattc | 60 |
| ggctatgact gggcacaaca gacaatcggc tgctctgatg ccgccgtgtt ccggctgtca | 120 |
| gcgcaggggc gcccggttct ttttgtcaag accgacctgt ccggtgccct gaatgaactg | 180 |
| caggacgagg cagcgcggct atcgtggctg gccacgacgg gcgttccttg cgcagctgtg | 240 |
| ctcgacgttg tcactgaagc gggaagggac tggctgctat tgggcgaagt gccggggcag | 300 |
| gatctcctgt catctcacct tgctcctgcc gagaaagtat ccatcatggc tgatgcaatg | 360 |
| cggcggctgc atacgcttga tccggctacc tgcccattcg accaccaagc gaaacatcgc | 420 |
| atcgagcgag cacgtactcg gatggaagcc ggtcttgtcg atcaggatga tctggacgaa | 480 |
| gagcatcagg ggctcgcgcc agccgaactg ttcgccaggc tcaaggcgcg catgcccgac | 540 |
| ggcgaggatc tcgtcgtgac ccatggcgat gcctgcttgc cgaatatcat ggtggaaaat | 600 |
| ggccgctttt ctggattcat cgactgtggc cggctgggtg tggcggaccg ctatcaggac | 660 |
| atagcgttgg ctacccgtga tattgctgaa gagcttggcg gcgaatgggc tgaccgcttc | 720 |
| ctcgtgcttt acggtatcgc cgctcccgat tcgcagcgca tcgccttcta tcgccttctt | 780 |

-continued

| | |
|---|---|
| gacgagttct tctaa | 795 |

<210> SEQ ID NO 36
<211> LENGTH: 3434
<212> TYPE: DNA
<213> ORGANISM: Artificial Sequence
<220> FEATURE:
<223> OTHER INFORMATION: Plasmid pKD13

<400> SEQUENCE: 36

| | |
|---|---|
| agattgcagc attacacgtc ttgagcgatt gtgtaggctg gagctgcttc gaagttccta | 60 |
| tactttctag agaataggaa cttcggaata ggaacttcaa gatcccctta ttagaagaac | 120 |
| tcgtcaagaa ggcgatagaa ggcgatgcgc tgcgaatcgg gagcggcgat accgtaaagc | 180 |
| acgaggaagc ggtcagccca ttcgccgcca agctcttcag caatatcacg ggtagccaac | 240 |
| gctatgtcct gatagcggtc cgccacaccc agccggccac agtcgatgaa tccagaaaag | 300 |
| cggccatttt ccaccatgat attcggcaag caggcatcgc catgggtcac gacgagatcc | 360 |
| tcgccgtcgg gcatgcgcgc cttgagcctg gcgaacagtt cggctggcgc gagcccctga | 420 |
| tgctcttcgt ccagatcatc ctgatcgaca agaccggctt ccatccgagt acgtgctcgc | 480 |
| tcgatgcgat gtttcgcttg gtggtcgaat gggcaggtag ccggatcaag cgtatgcagc | 540 |
| cgccgcattg catcagccat gatggatact ttctcggcag gagcaaggtg agatgacagg | 600 |
| agatcctgcc ccggcacttc gcccaatagc agccagtccc ttcccgcttc agtgacaacg | 660 |
| tcgagcacag ctgcgcaagg aacgcccgtc gtggccagcc acgatagccg cgctgcctcg | 720 |
| tcctgcagtt cattcagggc accggacagg tcggtcttga caaaaagaac cgggcgcccc | 780 |
| tgcgctgaca gccggaacac ggcggcatca gagcagccga ttgtctgttg tgcccagtca | 840 |
| tagccgaata gcctctccac ccaagcggcc ggagaacctg cgtgcaatcc atcttgttca | 900 |
| atcatgcgaa acgatcctca tcctgtctct tgatcagatc ttgatcccct gcgccatcag | 960 |
| atccttggcg gcaagaaagc catccagttt actttgcagg gcttcccaac cttaccagag | 1020 |
| ggcgccccag ctggcaattc cggttcgctt gctgtccata aaaccgccca gtctagctat | 1080 |
| cgccatgtaa gcccactgca agctacctgc tttctctttg cgcttgcgtt ttcccttgtc | 1140 |
| cagatagccc agtagctgac attcatccgg ggtcagcacc gtttctgcgg actggctttc | 1200 |
| tacgtgttcc gcttccttta gcagcccttg cgccctgagt gcttgcggca gcgtgagctt | 1260 |
| caaaagcgct ctgaagttcc tatactttct agagaatagg aacttcgaac tgcaggtcga | 1320 |
| cggatccccg gaattaattc tcatgtttga cagcttatca ctgatcagtg aattaatggc | 1380 |
| gatgacgcat cctcacgata atatccgggt aggcgcaatc actttcgtct ctactccgtt | 1440 |
| acaaagcgag gctgggtatt tcccggcctt tctgttatcc gaaatccact gaaagcacag | 1500 |
| cggctggctg aggagataaa taataaacga ggggctgtat gcacaaagca tcttctgttg | 1560 |
| agttaagaac gagtatcgag atggcacata gccttgctca aattggaatc aggtttgtgc | 1620 |
| caataccagt agaaacagac gaagaagcta gctttgcact ggattgcgag ctttgccat | 1680 |
| ggctaattcc catgtcagcc gttaagtgtt cctgtgtcac tgaaaattgc tttgagaggc | 1740 |
| tctaagggct tctcagtgcg ttacatccct ggcttgttgt ccacaaccgt aaaccttaa | 1800 |
| aagctttaaa agcctatat attctttttt ttcttataaa acttaaaacc ttagaggcta | 1860 |
| tttaagttgc tgatttatat taatttatt gttcaaacat gagagcttag tacgtgaaac | 1920 |
| atgagagctt agtacgttag ccatgagagc ttagtacgtt agccatgagg gtttagttcg | 1980 |
| ttaaacatga gagcttagta cgttaaacat gagagcttag tacgtgaaac atgagagctt | 2040 |

```
agtacgtact atcaacaggt tgaactgcgg atcttgcggc cgcaaaaatt aaaaatgaag    2100
ttttaaatca atctaaagta tatatgagta aacttggtct gacagttacc aatgcttaat    2160
cagtgaggca cctatctcag cgatctgtct atttcgttca tccatagttg cctgactccc    2220
cgtcgtgtag ataactacga tacgggaggg cttaccatct ggccccagtg ctgcaatgat    2280
accgcgagac ccacgctcac cggctccaga tttatcagca ataaaccagc cagccggaag    2340
ggccgagcgc agaagtggtc ctgcaacttt atccgcctcc atccagtcta ttaattgttg    2400
ccgggaagct agagtaagta gttcgccagt taatagtttg cgcaacgttg ttgccattgc    2460
tacaggcatc gtggtgtcac gctcgtcgtt tggtatggct tcattcagct ccggttccca    2520
acgatcaagg cgagttacat gatccccat gttgtgcaaa aaagcggtta gctccttcgg    2580
tcctccgatc gttgtcagaa gtaagttggc cgcagtgtta tcactcatgg ttatggcagc    2640
actgcataat tctcttactg tcatgccatc cgtaagatgc ttttctgtga ctggtgagta    2700
ctcaaccaag tcattctgag aatagtgtat gcggcgaccg agttgctctt gcccggcgtc    2760
aatacgggat aataccgcgc cacatagcag aactttaaaa gtgctcatca ttggaaaacg    2820
ttcttcgggg cgaaaactct caaggatctt accgctgttg agatccagtt cgatgtaacc    2880
cactcgtgca cccaactgat cttcagcatc ttttactttc accagcgttt ctgggtgagc    2940
aaaaacagga aggcaaaatg ccgcaaaaaa gggaataagg gcgacacgga aatgttgaat    3000
actcatactc ttcctttttc aatattattg aagcatttat cagggttatt gtctcatgag    3060
cggatacata tttgaatgta tttagaaaaa taaacaaata ggggttccgc gcacatttcc    3120
ccgaaaagtg ccacctgcat cgatggcccc ccgatggtag tgtggggtct ccccatgcga    3180
gagtagggaa ctgccaggca tcaaataaaa cgaaaggctc agtcgaaaga ctgggccttt    3240
cgttttatct gttgtttgtc ggtgaacgct ctcctgagta ggacaaatcc gccgggagcg    3300
gatttgaacg ttgcgaagca acggcccgga gggtggcggg caggacgccc gccataaact    3360
gccaggcatc aaattaagca gaaggccatc ctgacggatg cctttttgc gtggccagtg    3420 ccaagcttgc atgc                                                     3434
```

<210> SEQ ID NO 37
<211> LENGTH: 80
<212> TYPE: DNA
<213> ORGANISM: Artificial Sequence
<220> FEATURE:
<223> OTHER INFORMATION: Primer

<400> SEQUENCE: 37

```
atgagcacgt cagacgatat ccataacacc acagccactg gcaaatgccc gttccatcag    60
gtgtaggctg gagctgcttc                                                80
```

<210> SEQ ID NO 38
<211> LENGTH: 82
<212> TYPE: DNA
<213> ORGANISM: Artificial Sequence
<220> FEATURE:
<223> OTHER INFORMATION: Primer

<400> SEQUENCE: 38

```
taacagcagg tcgaaacggt cgaggttcat cactttcacc catgccgcca cgaagtcttt    60
attccgggga tccgtcgacc tg                                             82
```

<210> SEQ ID NO 39
<211> LENGTH: 1424
<212> TYPE: DNA

```
<213> ORGANISM: Artificial Sequence
<220> FEATURE:
<223> OTHER INFORMATION: Synthetic construct

<400> SEQUENCE: 39
taacagcagg tcgaaacggt cgaggttcat cactttcacc catgccgcca cgaagtcttt      60
attccgggga tccgtcgacc tgcagttcga agttcctatt ctctagaaag tataggaact     120
tcagagcgct tttgaagctc acgctgccgc aagcactcag ggcgcaaggg ctgctaaagg     180
aagcggaaca cgtagaaagc cagtccgcag aaacggtgct gaccccggat gaatgtcagc     240
tactgggcta tctggacaag ggaaaacgca agcgcaaaga gaaagcaggt agcttgcagt     300
gggcttacat ggcgatagct agactgggcg gtttttatgga cagcaagcga accggaattg     360
ccagctgggg cgccctctgg taaggttggg aagccctgca agtaaactg gatggctttc      420
ttgccgccaa ggatctgatg cgcagggga tcaagatctg atcaagagac aggatgagga     480
tcgtttcgca tgattgaaca agatggattg cacgcaggtt ctccggccgc ttgggtggag     540
aggctattcg gctatgactg gcacaacag acaatcggct gctctgatgc cgccgtgttc      600
cggctgtcag cgcaggggcg cccggttctt tttgtcaaga ccgacctgtc cggtgccctg     660
aatgaactgc aggacgaggc agcgcggcta tcgtggctgg ccacgacggg cgttccttgc     720
gcagctgtgc tcgacgttgt cactgaagcg ggaagggact ggctgctatt gggcgaagtg     780
ccggggcagg atctcctgtc atctcacctt gctcctgccg agaaagtatc catcatggct     840
gatgcaatgc ggcggctgca tacgcttgat ccggctacct gcccattcga ccaccaagcg     900
aaacatcgca tcgagcgagc acgtactcgg atggaagccg gtcttgtcga tcaggatgat     960
ctggacgaag agcatcaggg gctcgcgcca gccgaactgt tcgccaggct caaggcgcgc    1020
atgcccgacg gcgaggatct cgtcgtgacc catggcgatg cctgcttgcc gaatatcatg    1080
gtggaaaatg gccgcttttc tggattcatc gactgtggcc ggctgggtgt ggcggaccgc    1140
tatcaggaca tagcgttggc tacccgtgat attgctgaag agcttggcgg cgaatgggct    1200
gaccgcttcc tcgtgcttta cggtatcgcc gctcccgatt cgcagcgcat cgccttctat    1260
cgccttcttg acgagttctt ctaataaggg gatcttgaag ttcctattcc gaagttccta    1320
ttctctagaa agtataggaa cttcgaagca gctccagcct acacctgatg gaacgggcat    1380
ttgccagtgg ctgtggtgtt atggatatcg tctgacgtgc tcat                     1424

<210> SEQ ID NO 40
<211> LENGTH: 2181
<212> TYPE: DNA
<213> ORGANISM: Escherichia coli
<220> FEATURE:
<221> NAME/KEY: CDS
<222> LOCATION: (1)..(2181)

<400> SEQUENCE: 40 atg agc acg tca gac gat atc cat aac acc aca gcc act ggc aaa tgc      48
Met Ser Thr Ser Asp Asp Ile His Asn Thr Thr Ala Thr Gly Lys Cys
1               5                   10                  15 ccg ttc cat cag ggc ggt cac gac cag agt gcg ggg gcg ggc aca acc      96
Pro Phe His Gln Gly Gly His Asp Gln Ser Ala Gly Ala Gly Thr Thr
            20                  25                  30 act cgc gac tgg tgg cca aat caa ctt cgt gtt gac ctg tta aac caa    144
Thr Arg Asp Trp Trp Pro Asn Gln Leu Arg Val Asp Leu Leu Asn Gln
        35                  40                  45 cat tct aat cgt tct aac cca ctg ggt gag gac ttt gac tac cgc aaa    192
His Ser Asn Arg Ser Asn Pro Leu Gly Glu Asp Phe Asp Tyr Arg Lys
    50                  55                  60
```

```
gaa ttc agc aaa tta gat tac tac ggc ctg aaa aaa gat ctg aaa gcc    240
Glu Phe Ser Lys Leu Asp Tyr Tyr Gly Leu Lys Lys Asp Leu Lys Ala
 65              70                  75                  80 ctg ttg aca gaa tct caa ccg tgg tgg cca gcc gac tgg ggc agt tac    288
Leu Leu Thr Glu Ser Gln Pro Trp Trp Pro Ala Asp Trp Gly Ser Tyr
             85                  90                  95 gcc ggt ctg ttt att cgt atg gcc tgg cac ggc gcg ggg act tac cgt    336
Ala Gly Leu Phe Ile Arg Met Ala Trp His Gly Ala Gly Thr Tyr Arg
        100                 105                 110 tca atc gat gga cgc ggt ggc gcg ggt cgt ggt cag caa cgt ttt gca    384
Ser Ile Asp Gly Arg Gly Gly Ala Gly Arg Gly Gln Gln Arg Phe Ala
                115                 120                 125 ccg ctg aac tcc tgg ccg gat aac gta agc ctc gat aaa gcg cgt cgc    432
Pro Leu Asn Ser Trp Pro Asp Asn Val Ser Leu Asp Lys Ala Arg Arg
130                 135                 140 ctg ttg tgg cca atc aaa cag aaa tat ggt cag aaa atc tcc tgg gcc    480
Leu Leu Trp Pro Ile Lys Gln Lys Tyr Gly Gln Lys Ile Ser Trp Ala
145                 150                 155                 160 gac ctg ttt atc ctc gcg ggt aac gtg gcg cta gaa aac tcc ggc ttc    528
Asp Leu Phe Ile Leu Ala Gly Asn Val Ala Leu Glu Asn Ser Gly Phe
                165                 170                 175 cgt acc ttc ggt ttt ggt gcc ggt cgt gaa gac gtc tgg gaa ccg gat    576
Arg Thr Phe Gly Phe Gly Ala Gly Arg Glu Asp Val Trp Glu Pro Asp
            180                 185                 190 ctg gat gtt aac tgg ggt gat gaa aaa gcc tgg ctg act cac cgt cat    624
Leu Asp Val Asn Trp Gly Asp Glu Lys Ala Trp Leu Thr His Arg His
        195                 200                 205 ccg gaa gcg ctg gcg aaa gca ccg ctg ggt gca acc gag atg ggt ctg    672
Pro Glu Ala Leu Ala Lys Ala Pro Leu Gly Ala Thr Glu Met Gly Leu
210                 215                 220 att tac gtt aac ccg gaa ggc ccg gat cac agc ggc gaa ccg ctt tct    720
Ile Tyr Val Asn Pro Glu Gly Pro Asp His Ser Gly Glu Pro Leu Ser
225                 230                 235                 240 gcg gca gca gct atc cgc gcg acc ttc ggc aac atg ggc atg aac gac    768
Ala Ala Ala Ala Ile Arg Ala Thr Phe Gly Asn Met Gly Met Asn Asp
                245                 250                 255 gaa gaa acc gtg gcg ctg att gcg ggt ggt cat acg ctg ggt aaa acc    816
Glu Glu Thr Val Ala Leu Ile Ala Gly Gly His Thr Leu Gly Lys Thr
            260                 265                 270 cac ggt gcc ggt ccg aca tca aat gta ggt cct gat cca gaa gct gca    864
His Gly Ala Gly Pro Thr Ser Asn Val Gly Pro Asp Pro Glu Ala Ala
        275                 280                 285 ccg att gaa gaa caa ggt tta ggt tgg gcg agc act tac ggc agc ggc    912
Pro Ile Glu Glu Gln Gly Leu Gly Trp Ala Ser Thr Tyr Gly Ser Gly
290                 295                 300 gtt ggc gca gat gcc att acc tct ggt ctg gaa gta gtc tgg acc cag    960
Val Gly Ala Asp Ala Ile Thr Ser Gly Leu Glu Val Val Trp Thr Gln
305                 310                 315                 320 acg ccg acc cag tgg agc aac tat ttc ttc gag aac ctg ttc aag tat   1008
Thr Pro Thr Gln Trp Ser Asn Tyr Phe Phe Glu Asn Leu Phe Lys Tyr
                325                 330                 335 gag tgg gta cag acc cgc agc ccg gct ggc gca atc cag ttc gaa gcg   1056
Glu Trp Val Gln Thr Arg Ser Pro Ala Gly Ala Ile Gln Phe Glu Ala
            340                 345                 350 gta gac gca ccg gaa att atc ccg gat ccg ttt gat ccg tcg aag aaa   1104
Val Asp Ala Pro Glu Ile Ile Pro Asp Pro Phe Asp Pro Ser Lys Lys
        355                 360                 365 cgt aaa ccg aca atg ctg gtg acc gac ctg acg ctg cgt ttt gat cct   1152
Arg Lys Pro Thr Met Leu Val Thr Asp Leu Thr Leu Arg Phe Asp Pro
370                 375                 380
```

| | | |
|---|---|---|
| gag ttc gag aag atc tct cgt cgt ttc ctc aac gat ccg cag gcg ttc<br>Glu Phe Glu Lys Ile Ser Arg Arg Phe Leu Asn Asp Pro Gln Ala Phe<br>385                         390                 395                     400 | | 1200 |
| aac gaa gcc ttt gcc cgt gcc tgg ttc aaa ctg acg cac agg gat atg<br>Asn Glu Ala Phe Ala Arg Ala Trp Phe Lys Leu Thr His Arg Asp Met<br>                   405                       410                       415 | | 1248 |
| ggg ccg aaa tct cgc tac atc ggg ccg gaa gtg ccg aaa gaa gat ctg<br>Gly Pro Lys Ser Arg Tyr Ile Gly Pro Glu Val Pro Lys Glu Asp Leu<br>               420                       425                   430 | | 1296 |
| atc tgg caa gat ccg ctg ccg cag ccg atc tac aac ccg acc gag cag<br>Ile Trp Gln Asp Pro Leu Pro Gln Pro Ile Tyr Asn Pro Thr Glu Gln<br>             435                       440                    445 | | 1344 |
| gac att atc gat ctg aaa ttc gcg att gcg gat tct ggt ctg tct gtt<br>Asp Ile Ile Asp Leu Lys Phe Ala Ile Ala Asp Ser Gly Leu Ser Val<br>450                         455                 460 | | 1392 |
| agt gag ctg gta tcg gtg gcc tgg gca tct gct tct acc ttc cgt ggt<br>Ser Glu Leu Val Ser Val Ala Trp Ala Ser Ala Ser Thr Phe Arg Gly<br>465                         470                 475                     480 | | 1440 |
| ggc gac aaa cgc ggt ggt gcc aac ggt gcg cgt ctg gca tta atg ccg<br>Gly Asp Lys Arg Gly Gly Ala Asn Gly Ala Arg Leu Ala Leu Met Pro<br>                   485                       490                   495 | | 1488 |
| cag cgc gac tgg gat gtg aac gcc gca gcc gtt cgt gct ctg cct gtt<br>Gln Arg Asp Trp Asp Val Asn Ala Ala Ala Val Arg Ala Leu Pro Val<br>             500                       505                    510 | | 1536 |
| ctg gag aaa atc cag aaa gag tct ggt aaa gcc tcg ctg gcg gat atc<br>Leu Glu Lys Ile Gln Lys Glu Ser Gly Lys Ala Ser Leu Ala Asp Ile<br>             515                       520                   525 | | 1584 |
| ata gtg ctg gct ggt gtg gtt ggt gtt gag aaa gcc gca agc gcc gca<br>Ile Val Leu Ala Gly Val Val Gly Val Glu Lys Ala Ala Ser Ala Ala<br>530                         535                 540 | | 1632 |
| ggt ttg agc att cat gta ccg ttt gcg ccg ggt cgc gtt gat gcg cgt<br>Gly Leu Ser Ile His Val Pro Phe Ala Pro Gly Arg Val Asp Ala Arg<br>545                         550                 555                     560 | | 1680 |
| cag gat cag act gac att gag atg ttt gag ctg ctg gag cca att gct<br>Gln Asp Gln Thr Asp Ile Glu Met Phe Glu Leu Leu Glu Pro Ile Ala<br>                   565                       570                    575 | | 1728 |
| gac ggt ttc cgt aac tat cgc gct cgt ctg gac gtt tcc acc acc gag<br>Asp Gly Phe Arg Asn Tyr Arg Ala Arg Leu Asp Val Ser Thr Thr Glu<br>             580                       585                    590 | | 1776 |
| tca ctg ctg atc gac aaa gca cag caa ctg acg ctg acc gcg ccg gaa<br>Ser Leu Leu Ile Asp Lys Ala Gln Gln Leu Thr Leu Thr Ala Pro Glu<br>             595                       600                   605 | | 1824 |
| atg act gcg ctg gtg ggc ggc atg cgt gta ctg ggt gcc aac ttc gat<br>Met Thr Ala Leu Val Gly Gly Met Arg Val Leu Gly Ala Asn Phe Asp<br>610                         615                 620 | | 1872 |
| ggc agc aaa aac ggc gtc ttc act gac cgc gtt ggc gta ttg agc aat<br>Gly Ser Lys Asn Gly Val Phe Thr Asp Arg Val Gly Val Leu Ser Asn<br>625                         630                 635                     640 | | 1920 |
| gac ttc ttc gtg aac ttg ctg gat atg cgt tac gag tgg aaa gcg acc<br>Asp Phe Phe Val Asn Leu Leu Asp Met Arg Tyr Glu Trp Lys Ala Thr<br>                   645                       650                    655 | | 1968 |
| gac gaa tcg aaa gag ctg ttc gaa ggc cgt gac cgt gaa acc ggc gaa<br>Asp Glu Ser Lys Glu Leu Phe Glu Gly Arg Asp Arg Glu Thr Gly Glu<br>             660                       665                   670 | | 2016 |
| gtg aaa ttt acg gcc agc cgt gcg gat ctg gtg ttt ggt tct aac tcc<br>Val Lys Phe Thr Ala Ser Arg Ala Asp Leu Val Phe Gly Ser Asn Ser<br>             675                       680                   685 | | 2064 |
| gtc ctg cgt gcg gtg gcg gaa gtt tac gcc agt agc gat gcc cac gag<br>Val Leu Arg Ala Val Ala Glu Val Tyr Ala Ser Ser Asp Ala His Glu<br>690                         695                 700 | | 2112 |

```
aag ttt gtt aaa gac ttc gtg gcg gca tgg gtg aaa gtg atg aac ctc      2160
Lys Phe Val Lys Asp Phe Val Ala Ala Trp Val Lys Val Met Asn Leu
705             710                 715                 720 gac cgt ttc gac ctg ctg taa                                          2181
Asp Arg Phe Asp Leu Leu
                725
```

<210> SEQ ID NO 41
<211> LENGTH: 726
<212> TYPE: PRT
<213> ORGANISM: Escherichia coli

<400> SEQUENCE: 41

```
Met Ser Thr Ser Asp Ile His Asn Thr Ala Thr Gly Lys Cys
1               5                   10                  15

Pro Phe His Gln Gly Gly His Asp Gln Ser Ala Gly Thr Thr
                20                  25                  30

Thr Arg Asp Trp Trp Pro Asn Gln Leu Arg Val Asp Leu Leu Asn Gln
            35                  40                  45

His Ser Asn Arg Ser Asn Pro Leu Gly Glu Asp Phe Asp Tyr Arg Lys
50                  55                  60

Glu Phe Ser Lys Leu Asp Tyr Tyr Gly Leu Lys Lys Asp Leu Lys Ala
65                  70                  75                  80

Leu Leu Thr Glu Ser Gln Pro Trp Trp Pro Ala Asp Trp Gly Ser Tyr
                85                  90                  95

Ala Gly Leu Phe Ile Arg Met Ala Trp His Gly Ala Gly Thr Tyr Arg
            100                 105                 110

Ser Ile Asp Gly Arg Gly Gly Ala Gly Arg Gly Gln Gln Arg Phe Ala
        115                 120                 125

Pro Leu Asn Ser Trp Pro Asp Asn Val Ser Leu Asp Lys Ala Arg Arg
130                 135                 140

Leu Leu Trp Pro Ile Lys Gln Lys Tyr Gly Gln Lys Ile Ser Trp Ala
145                 150                 155                 160

Asp Leu Phe Ile Leu Ala Gly Asn Val Ala Leu Glu Asn Ser Gly Phe
                165                 170                 175

Arg Thr Phe Gly Phe Gly Ala Gly Arg Glu Asp Val Trp Glu Pro Asp
            180                 185                 190

Leu Asp Val Asn Trp Gly Asp Glu Lys Ala Trp Leu Thr His Arg His
        195                 200                 205

Pro Glu Ala Leu Ala Lys Ala Pro Leu Gly Ala Thr Glu Met Gly Leu
    210                 215                 220

Ile Tyr Val Asn Pro Glu Gly Pro Asp His Ser Gly Glu Pro Leu Ser
225                 230                 235                 240

Ala Ala Ala Ala Ile Arg Ala Thr Phe Gly Asn Met Gly Met Asn Asp
                245                 250                 255

Glu Glu Thr Val Ala Leu Ile Ala Gly Gly His Thr Leu Gly Lys Thr
            260                 265                 270

His Gly Ala Gly Pro Thr Ser Asn Val Gly Pro Asp Pro Glu Ala Ala
        275                 280                 285

Pro Ile Glu Glu Gln Gly Leu Gly Trp Ala Ser Thr Tyr Gly Ser Gly
    290                 295                 300

Val Gly Ala Asp Ala Ile Thr Ser Gly Leu Glu Val Val Trp Thr Gln
305                 310                 315                 320

Thr Pro Thr Gln Trp Ser Asn Tyr Phe Phe Glu Asn Leu Phe Lys Tyr
                325                 330                 335
```

```
Glu Trp Val Gln Thr Arg Ser Pro Ala Gly Ala Ile Gln Phe Glu Ala
            340                 345                 350

Val Asp Ala Pro Glu Ile Ile Pro Asp Pro Phe Asp Pro Ser Lys Lys
            355                 360                 365

Arg Lys Pro Thr Met Leu Val Thr Asp Leu Thr Leu Arg Phe Asp Pro
370                 375                 380

Glu Phe Glu Lys Ile Ser Arg Arg Phe Leu Asn Asp Pro Gln Ala Phe
385                 390                 395                 400

Asn Glu Ala Phe Ala Arg Ala Trp Phe Lys Leu Thr His Arg Asp Met
                405                 410                 415

Gly Pro Lys Ser Arg Tyr Ile Gly Pro Glu Val Pro Lys Glu Asp Leu
            420                 425                 430

Ile Trp Gln Asp Pro Leu Pro Gln Pro Ile Tyr Asn Pro Thr Glu Gln
            435                 440                 445

Asp Ile Ile Asp Leu Lys Phe Ala Ile Ala Asp Ser Gly Leu Ser Val
            450                 455                 460

Ser Glu Leu Val Ser Val Ala Trp Ala Ser Ala Ser Thr Phe Arg Gly
465                 470                 475                 480

Gly Asp Lys Arg Gly Gly Ala Asn Gly Ala Arg Leu Ala Leu Met Pro
                485                 490                 495

Gln Arg Asp Trp Asp Val Asn Ala Ala Ala Val Arg Ala Leu Pro Val
            500                 505                 510

Leu Glu Lys Ile Gln Lys Glu Ser Gly Lys Ala Ser Leu Ala Asp Ile
            515                 520                 525

Ile Val Leu Ala Gly Val Val Gly Val Glu Lys Ala Ala Ser Ala Ala
            530                 535                 540

Gly Leu Ser Ile His Val Pro Phe Ala Pro Gly Arg Val Asp Ala Arg
545                 550                 555                 560

Gln Asp Gln Thr Asp Ile Glu Met Phe Glu Leu Leu Glu Pro Ile Ala
                565                 570                 575

Asp Gly Phe Arg Asn Tyr Arg Ala Arg Leu Asp Val Ser Thr Thr Glu
            580                 585                 590

Ser Leu Leu Ile Asp Lys Ala Gln Gln Leu Thr Leu Thr Ala Pro Glu
            595                 600                 605

Met Thr Ala Leu Val Gly Gly Met Arg Val Leu Gly Ala Asn Phe Asp
610                 615                 620

Gly Ser Lys Asn Gly Val Phe Thr Asp Arg Val Gly Val Leu Ser Asn
625                 630                 635                 640

Asp Phe Phe Val Asn Leu Leu Asp Met Arg Tyr Glu Trp Lys Ala Thr
                645                 650                 655

Asp Glu Ser Lys Glu Leu Phe Glu Gly Arg Asp Arg Glu Thr Gly Glu
            660                 665                 670

Val Lys Phe Thr Ala Ser Arg Ala Asp Leu Val Phe Gly Ser Asn Ser
            675                 680                 685

Val Leu Arg Ala Val Ala Glu Val Tyr Ala Ser Ser Asp Ala His Glu
690                 695                 700

Lys Phe Val Lys Asp Phe Val Ala Ala Trp Val Lys Val Met Asn Leu
705                 710                 715                 720

Asp Arg Phe Asp Leu Leu
                725

<210> SEQ ID NO 42
<211> LENGTH: 6329
<212> TYPE: DNA
<213> ORGANISM: Artificial Sequence
```

<220> FEATURE:
<223> OTHER INFORMATION: Plasmid pKD46

<400> SEQUENCE: 42

```
catcgattta ttatgacaac ttgacggcta catcattcac tttttcttca caaccggcac      60
ggaactcgct cgggctggcc ccggtgcatt ttttaaatac ccgcgagaaa tagagttgat     120
cgtcaaaacc aacattgcga ccgacggtgg cgataggcat ccgggtggtg ctcaaaagca     180
gcttcgcctg gctgatacgt tggtcctcgc gccagcttaa gacgctaatc cctaactgct     240
ggcggaaaag atgtgacaga cgcgacggcg acaagcaaac atgctgtgcg acgctggcga     300
tatcaaaatt gctgtctgcc aggtgatcgc tgatgtactg acaagcctcg cgtacccgat     360
tatccatcgg tggatggagc gactcgttaa tcgcttccat gcgccgcagt aacaattgct     420
caagcagatt tatcgccagc agctccgaat agcgcccttc cccttgcccg cgttaatga      480
tttgcccaaa caggtcgctg aaatgcggct ggtgcgcttc atccgggcga agaaccccg      540
tattggcaaa tattgacggc cagttaagcc attcatgcca gtaggcgcgc ggacgaaagt     600
aaacccactg gtgataccat tcgcgagcct ccggatgacg accgtagtga tgaatctctc     660
ctggcgggaa cagcaaaata tcacccggtc ggcaaacaaa ttctcgtccc tgattttca     720
ccacccctg accgcgaatg gtgagattga gaatataacc tttcattccc agcggtcggt     780
cgataaaaaa atcgagataa ccgttggcct caatcggcgt taaacccgcc accagatggg     840
cattaaacga gtatcccggc agcaggggat cattttgcgc ttcagccata cttttcatac     900
tcccgccatt cagagaagaa accaattgtc catattgcat cagacattgc cgtcactgcg     960
tcttttactg gctcttctcg ctaaccaaac cggtaacccc gcttattaaa agcattctgt    1020
aacaaagcgg gaccaaagcc atgacaaaaa cgcgtaacaa agtgtctat aatcacggca    1080
gaaaagtcca cattgattat ttgcacggcg tcacactttg ctatgccata gcatttttat    1140
ccataagatt agcggatcct acctgacgct ttttatcgca actctctact gtttctccat    1200
acccgttttt ttgggaattc gagctctaag gaggttataa aaaatggata ttaatactga    1260
aactgagatc aagcaaaagc attcactaac ccccttttcct gttttcctaa tcagcccggc    1320
atttcgcggg cgatattttc acagctatt caggagttca gccatgaacg cttattacat    1380
tcaggatcgt cttgaggctc agagctgggc gcgtcactac cagcagctcg cccgtgaaga    1440
gaaagaggca gaactggcag acgacatgga aaaaggcctg ccccagcacc tgtttgaatc    1500
gctatgcatc gatcatttgc aacgccacgg ggccagcaaa aaatccatta cccgtgcgtt    1560
tgatgacgat gttgagtttc aggagcgcat ggcagaacac atccggtaca tggttgaaac    1620
cattgctcac caccaggttg atattgattc agaggtataa aacgaatgag tactgcactc    1680
gcaacgctgg ctgggaagct ggctgaacgt gtcggcatgg attctgtcga cccacaggaa    1740
ctgatcacca ctcttcgcca gacggcattt aaaggtgatg ccagcgatgc gcagttcatc    1800
gcattactga tcgttgccaa ccagtacggc cttaatccgt ggacgaaaga atttacgcc    1860
tttcctgata gcagaatgg catcgttccg gtggtgggcg ttgatggctg gtcccgcatc    1920
atcaatgaaa accagcagtt tgatggcatg actttgagc aggacaatga atcctgtaca    1980
tgccggattt accgcaagga ccgtaatcat ccgatctgcg ttaccgaatg gatggatgaa    2040
tgccgccgcg aaccattcaa aactcgcgaa ggcagagaaa tcacgggcc gtggcagtcg    2100
catcccaaac ggatgttacg tcataaagcc atgattcagt gtgcccgtct ggccttcgga    2160
tttgctggta tctatgacaa ggatgaagcc gagcgcattg tcgaaaatac tgcatacact    2220
gcagaacgtc agccggaacg cgacatcact ccggttaacg atgaaaccat gcaggagatt    2280
```

```
aacactctgc tgatcgccct ggataaaaca tgggatgacg acttattgcc gctctgttcc    2340
cagatatttc gccgcgacat tcgtgcatcg tcagaactga cacaggccga agcagtaaaa    2400
gctcttggat tcctgaaaca gaaagccgca gagcagaagg tggcagcatg acaccggaca    2460
ttatcctgca gcgtaccggg atcgatgtga gagctgtcga acaggggat gatgcgtggc     2520 acaaattacg gctcggcgtc atcaccgctt cagaagttca caacgtgata gcaaaacccc    2580
gctccggaaa gaagtggcct gacatgaaaa tgtcctactt ccacaccctg cttgctgagg    2640
tttgcaccgg tgtggctccg gaagttaacg ctaaagcact ggcctgggga aaacagtacg    2700
agaacgacgc cagaaccctg tttgaattca cttccggcgt gaatgttact gaatccccga    2760
tcatctatcg cgacgaaagt atgcgtaccg cctgctctcc cgatggttta tgcagtgacg    2820
gcaacggcct tgaactgaaa tgcccgttta cctcccggga tttcatgaag ttccggctcg    2880
gtggtttcga ggccataaag tcagcttaca tggcccaggt gcagtacagc atgtgggtga    2940
cgcgaaaaaa tgcctggtac tttgccaact atgacccgcg tatgaagcgt gaaggcctgc    3000
attatgtcgt gattgagcgg gatgaaaagt acatggcgag ttttgacgag atcgtgccgg    3060
agttcatcga aaaatggac gaggcactgg ctgaaattgg ttttgtattt ggggagcaat     3120
ggcgatgacg catcctcacg ataatatccg ggtaggcgca atcactttcg tctactccgt    3180
tacaaagcga ggctgggtat ttcccggcct ttctgttatc cgaaatccac tgaaagcaca    3240
gcggctggct gaggagataa ataataaacg aggggctgta tgcacaaagc atcttctgtt    3300
gagttaagaa cgagtatcga gatggcacat agccttgctc aaattggaat caggtttgtg    3360
ccaataccag tagaaacaga cgaagaatcc atgggtatgg acagttttcc ctttgatatg    3420
taacggtgaa cagttgttct acttttgttt gttagtcttg atgcttcact gatagataca    3480
agagccataa gaacctcaga tccttccgta tttagccagt atgttctcta gtgtggttcg    3540
ttgtttttgc gtgagccatg agaacgaacc attgagatca tacttacttt gcatgtcact    3600
caaaaatttt gcctcaaaac tggtgagctg aatttttgca gttaaagcat cgtgtagtgt    3660
ttttcttagt ccgttacgta ggtaggaatc tgatgtaatg gttgttggta ttttgtcacc    3720
attcattttt atctggttgt tctcaagttc ggttacgaga tccatttgtc tatctagttc    3780
aacttggaaa atcaacgtat cagtcgggcg gcctcgctta tcaaccacca atttcatatt    3840
gctgtaagtg tttaaatctt tacttattgg tttcaaaacc cattggttaa gccttttaaa    3900
ctcatggtag ttattttcaa gcattaacat gaacttaaat tcatcaaggc taatctctat    3960
atttgccttg tgagttttct tttgtgttag ttctttaat aaccactcat aaatcctcat      4020
agagtatttg ttttcaaaag acttaacatg ttccagatta tattttatga atttttttaa    4080
ctggaaaaga taaggcaata tctcttcact aaaaactaat tctaattttt cgcttgagaa    4140
cttggcatag tttgtccact ggaaaatctc aaagccttta accaaggat tcctgatttc     4200 cacagttctc gtcatcagct ctctggttgc tttagctaat acaccataag catttccct     4260 actgatgttc atcatctgag cgtattggtt ataagtgaac gataccgtcc gttctttcct    4320
tgtagggttt tcaatcgtgg ggttgagtag tgccacacag cataaaatta gcttggtttc    4380
atgctccgtt aagtcatagc gactaatcgc tagttcattt gctttgaaaa caactaattc    4440
agacatacat ctcaattggt ctaggtgatt ttaatcacta taccaattga gatgggctag    4500
tcaatgataa ttactagtcc ttttcctttg agttgtgggt atctgtaaat tctgctagac    4560
ctttgctgga aaacttgtaa attctgctag accctctgta aattccgcta gacctttgtg    4620 tgttttttttt gtttatattc aagtggttat aatttataga ataaagaaag aataaaaaaa    4680
```

```
gataaaaaga atagatccca gccctgtgta taactcacta ctttagtcag ttccgcagta     4740
ttacaaaagg atgtcgcaaa cgctgtttgc tcctctacaa aacagacctt aaaaccctaa     4800
aggcttaagt agcaccctcg caagctcggt tgcggccgca atcgggcaaa tcgctgaata     4860
ttccttttgt ctccgaccat caggcacctg agtcgctgtc tttttcgtga cattcagttc     4920
gctgcgctca cggctctggc agtgaatggg ggtaaatggc actacaggcg ccttttatgg     4980
attcatgcaa ggaaactacc cataatacaa gaaaagcccg tcacgggctt ctcagggcgt     5040
tttatggcgg gtctgctatg tggtgctatc tgacttttg ctgttcagca gttcctgccc     5100
tctgattttc cagtctgacc acttcggatt atcccgtgac aggtcattca gactggctaa     5160
tgcacccagt aaggcagcgg tatcatcaac ggggtctgac gctcagtgga acgaaaactc     5220
acgttaaggg attttggtca tgagattatc aaaaaggatc ttcacctaga tccttttaaa     5280
ttaaaaatga agttttaaat caatctaaag tatatatgag taaacttggt ctgacagtta     5340
ccaatgctta atcagtgagg cacctatctc agcgatctgt ctatttcgtt catccatagt     5400
tgcctgactc cccgtcgtgt agataactac gatacgggag ggcttaccat ctggccccag     5460
tgctgcaatg ataccgcgag acccacgctc accggctcca gatttatcag caataaacca     5520
gccagccgga agggccgagc gcagaagtgg tcctgcaact ttatccgcct ccatccagtc     5580
tattaattgt tgccgggaag ctagagtaag tagttcgcca gttaatagtt tgcgcaacgt     5640
tgttgccatt gctacaggca tcgtggtgtc acgctcgtcg tttggtatgg cttcattcag     5700
ctccggttcc caacgatcaa ggcgagttac atgatccccc atgttgtgca aaaaagcggt     5760
tagctccttc ggtcctccga tcgttgtcag aagtaagttg gccgcagtgt tatcactcat     5820
ggttatggca gcactgcata attctcttac tgtcatgcca tccgtaagat gcttttctgt     5880
gactggtgag tactcaacca agtcattctg agaatagtgt atgcggcgac cgagttgctc     5940
ttgcccggcg tcaatacggg ataataccgc gccacatagc agaactttaa aagtgctcat     6000
cattggaaaa cgttcttcgg ggcgaaaact ctcaaggatc ttaccgctgt tgagatccag     6060
ttcgatgtaa cccactcgtg cacccaactg atcttcagca tcttttactt tcaccagcgt     6120
ttctgggtga gcaaaaacag gaaggcaaaa tgccgcaaaa aagggaataa gggcgacacg     6180
gaaatgttga atactcatac tcttcctttt tcaatattat tgaagcattt atcagggtta     6240
ttgtctcatg agcggataca tatttgaatg tatttagaaa aataaacaaa tagggggttcc     6300 gcgcacattt ccccgaaaag tgccacctg                                       6329
```

<210> SEQ ID NO 43
<211> LENGTH: 25
<212> TYPE: DNA
<213> ORGANISM: Artificial Sequence
<220> FEATURE:
<223> OTHER INFORMATION: Primer

<400> SEQUENCE: 43
aacaatatgt aagatctcaa ctatc                                             25

<210> SEQ ID NO 44
<211> LENGTH: 25
<212> TYPE: DNA
<213> ORGANISM: Artificial Sequence
<220> FEATURE:
<223> OTHER INFORMATION: Primer

<400> SEQUENCE: 44
cagacatgag agatccagtg tgtag                                             25

<210> SEQ ID NO 45
<211> LENGTH: 9332
<212> TYPE: DNA
<213> ORGANISM: Artificial Sequence
<220> FEATURE:
<223> OTHER INFORMATION: Plasmid pCP20

<400> SEQUENCE: 45

| | | | | | |
|---|---|---|---|---|---|
| gagacacaac | gtggctttgt | tgaataaatc | gaacttttgc | tgagttgaag | gatcagatca | 60 |
| cgcatcttcc | cgacaacgca | gaccgttccg | tggcaaagca | aaagttcaaa | atcaccaact | 120 |
| ggtccaccta | caacaaagct | ctcatcaacc | gtggctccct | cactttctgg | ctggatgatg | 180 |
| gggcgattca | ggcctggtat | gagtcagcaa | caccttcttc | acgaggcaga | cctcagcgcc | 240 |
| acaggtgcgg | ttgctggcgc | taaccgtttt | tatcaggctc | tgggaggcag | aataaatgat | 300 |
| catatcgtca | attattacct | ccacggggag | agcctgagca | aactggcctc | aggcatttga | 360 |
| gaagcacacg | gtcacactgc | ttccggtagt | caataaaccg | gtaaaccagc | aatagacata | 420 |
| agcggctatt | taacgaccct | gccctgaacc | gacgaccggg | tcgaatttgc | tttcgaattt | 480 |
| ctgccattca | tccgcttatt | atcacttatt | caggcgtagc | aaccaggcgt | ttaagggcac | 540 |
| caataactgc | cttaaaaaaa | ttacgccccg | ccctgccact | catcgcagta | ctgttgtaat | 600 |
| tcattaagca | ttctgccgac | atggaagcca | tcacaaacgg | catgatgaac | ctgaatcgcc | 660 |
| agcggcatca | gcaccttgtc | gccttgcgta | taatatttgc | ccatggtgaa | acgggggcg | 720 |
| aagaagttgt | ccatattggc | cacgtttaaa | tcaaaactgg | tgaaactcac | ccagggattg | 780 |
| gctgagacga | aaaacatatt | ctcaataaac | cctttaggga | aataggccag | gttttcaccg | 840 |
| taacacgcca | catcttgcga | atatatgtgt | agaaactgcc | ggaaatcgtc | gtggtattca | 900 |
| ctccagagcg | atgaaaacgt | ttcagtttgc | tcatggaaaa | cggtgtaaca | agggtgaaca | 960 |
| ctatcccata | tcaccagctc | accgtctttc | attgccatac | ggaattccgg | atgagcattc | 1020 |
| atcaggcggg | caagaatgtg | aataaaggcc | ggataaaact | tgtgcttatt | tttctttacg | 1080 |
| gtctttaaaa | aggccgtaat | atccagctga | acggtctggt | tataggtaca | ttgagcaact | 1140 |
| gactgaaatg | cctcaaaatg | ttctttacga | tgccattggg | atatatcaac | ggtggtatat | 1200 |
| ccagtgattt | ttttctccat | tttagcttcc | ttagctcctg | aaaatctcga | taactcaaaa | 1260 |
| aatacgcccg | gtagtgatct | tatttcatta | tggtgaaagt | tggaacctct | tacgtgccga | 1320 |
| tcaacgtctc | attttcgcca | aaagttggcc | cagggcttcc | cggtatcaac | agggacacca | 1380 |
| ggatttattt | attctgcgaa | gtgatcttcc | gtcacaggta | tttattcggc | gcaaagtgcg | 1440 |
| tcgggtgatg | ctgccaactt | actgatttag | tgtatgatgg | tgtttttgag | gtgctccagt | 1500 |
| ggcttctgtt | tctatcagct | gtccctcctg | ttcagctact | gacggggtgg | tgcgtaacgg | 1560 |
| caaaagcacc | gccggacatc | agcgcttgtt | tcggcgtggg | tatggtggca | ggccccgtgg | 1620 |
| ccgggggact | gttgggcgcc | tgtagtgcca | tttacccca | ttcactgcca | gagccgtgag | 1680 |
| cgcagcgaac | tgaatgtcac | gaaaaagaca | gcgactcagg | tgcctgatgg | tcggagacaa | 1740 |
| aaggaatatt | cagcgatttg | cccgagcttg | cgagggtgct | acttaagcct | ttagggtttt | 1800 |
| aaggtctgtt | ttgtagagga | gcaaacagcg | tttgcgacat | ccttttgtaa | tactgcggaa | 1860 |
| ctgactaaag | tagtgagtta | tacacagggc | tgggatctat | tcttttttatc | ttttttttatt | 1920 |
| ctttctttat | tctataaatt | ataaccactt | gaatataaac | aaaaaaaaca | cacaaggtc | 1980 |
| tagcggaatt | tacagagggt | ctagcagaat | ttacaagttt | tccagcaaag | gtctagcaga | 2040 |
| atttacagat | acccacaact | caaaggaaaa | ggactagtaa | ttatcattga | ctagcccatc | 2100 |

```
tcaattggta tagtgattaa aatcacctag accaattgag atgtatgtct gaattagttg    2160 tttttcaaagc aaatgaacta gcgattagtc gctatgactt aacggagcat gaaaccaagc   2220
taattttatg ctgtgtggca ctactcaacc ccacgattga aaaccctaca aggaaagaac    2280
ggacggtatc gttcacttat aaccaatacg ttcagatgat gaacatcagt agggaaaatg    2340
cttatggtgt attagctaaa gcaaccagag agctgatgac gagaactgtg gaaatcagga    2400
atcctttggt taaaggcttt gagatttttcc agtggacaaa ctatgccaag ttctcaagcg   2460
aaaaattaga attagttttt agtgaagaga tattgcctta tcttttccag ttaaaaaaat    2520
tcataaaata taatctggaa catgttaagt cttttgaaaa caaatactct atgaggattt    2580
atgagtggtt attaaaagaa ctaacacaaa agaaaactca caaggcaaat atagagatta    2640
gccttgatga atttaagttc atgttaatgc ttgaaaataa ctaccatgag tttaaaaggc    2700
ttaaccaatg ggttttgaaa ccaataagta aagatttaaa cacttacagc aatatgaaat    2760
tggtggttga taagcgaggc cgcccgactg atacgttgat tttccaagtt gaactagata    2820
gacaaatgga tctcgtaacc gaacttgaga acaaccagat aaaaatgaat ggtgacaaaa    2880
taccaacaac cattacatca gattcctacc tacataacgg actaagaaaa acactacacg    2940
atgctttaac tgcaaaaatt cagctcacca gttttgaggc aaaattttg agtgacatgc    3000 aaagtaagta tgatctcaat ggttcgttct catggctcac gcaaaaacaa cgaaccacac    3060
tagagaacat actggctaaa tacggaagga tctgaggttc ttatggctct tgtatctatc    3120
agtgaagcat caagactaac aaacaaaagt agaacaactg ttcaccgtta catatcaaag   3180
ggaaaactgt ccatatgcac agatgaaaac ggtgtaaaaa agatagatac atcagagctt    3240
ttacgagttt ttggtgcatt taagctgtt caccatgaac agatcgacaa tgtaacagat    3300
gaacagcatg taacacctaa tagaacaggt gaaaccagta aaacaaagca actagaacat    3360
gaaattgaac acctgagaca acttgttaca gctcaacagt cacacataga cagcctgaaa    3420
caggcgatgc tgcttatcga atcaaagctg ccgacaacac gggagccagt gacgcctccc    3480
gtggggaaaa aatcatggca attctggaag aaatagcgcc tgtttcgttt caggcaggtt    3540
atcagggagt gtcagcgtcc tgcggttctc cggggcgttc gggtcatgca gcccgtaatg    3600
gtgatttacc agcgtctgcc aggcatcaat tctaggcctg tctgcgcggt cgtagtacgg    3660
ctggaggcgt tttccggtct gtagctccat gttcggaatg acaaaattca gctcaagccg    3720
tcccttgtcc tggtgctcca cccacaggat gctgtactga ttttttttcga gaccgggcat   3780 cagtacacgc tcaaagctcg ccatcacttt ttcacgtcct cccggcggca gctccttctc    3840
cgcgaacgac agaacaccgg acgtgtattt cttcgcaaat ggcgtggcat cgatgagttc    3900
ccggacttct tccggattac cctgaagcac cgttgcgcct tcgcggttac gctccctccc    3960
cagcaggtaa tcaaccggac cactgccacc accttttccc ctggcatgaa atttaactat    4020
catcccgcgc ccctgttcc ctgacagcca gacgcagccg gcgcagctca tccccgatgg    4080
ccatcagtgc ggccaccacc tgaacccggt caccggaaga ccactgcccg ctgttcacct    4140
tacgggctgt ctgattcagg ttatttccga tggcggccag ctgacgcagt aacggcggtg    4200
ccagtgtcgg cagttttccg gaacgggcaa ccggctcccc caggcagacc cgccgcatcc    4260
ataccgccag ttgtttaccc tcacagcgtt caagtaaccg ggcatgttca tcatcagtaa    4320
cccgtattgt gagcatcctc tcgcgtttca tcggtatcat taccccatga acagaaatcc    4380
cccttacacg gaggcatcag tgactaaacg gggtctgacg ctcagtggaa cgaaaactca    4440
cgttaaggga ttttggtcat gagattatca aaaaggatct tcacctagat ccttttaaat    4500
```

```
taaaaatgaa gttttaaatc aatctaaagt atatatgagt aaacttggtc tgacagttac    4560
caatgcttaa tcagtgaggc acctatctca gcgatctgtc tatttcgttc atccatagtt    4620
gcctgactcc ccgtcgtgta gataactacg atacgggagg gcttaccatc tggcccagt     4680 gctgcaatga taccgcgaga cccacgctca ccggctccag atttatcagc aataaaccag    4740
ccagccggaa gggccgagcg cagaagtggt cctgcaactt tatccgcctc catccagtct    4800
attaattgtt gccgggaagc tagagtaagt agttcgccag ttaatagttt gcgcaacgtt    4860
gttgccattg ctgcaggcat cgtggtgtca cgctcgtcgt ttggtatggc ttcattcagc    4920
tccggttccc aacgatcaag gcgagttaca tgatccccca tgttgtgcaa aaaagcggtt    4980
agctccttcg gtcctccgat cgttgtcaga agtaagttgg ccgcagtgtt atcactcatg    5040
gttatggcag cactgcataa ttctcttact gtcatgccat ccgtaagatg cttttctgtg    5100
actggtgagt actcaaccaa gtcattctga aatagtgta tgcggcgacc gagttgctct     5160
tgcccggcgt caacacggga taataccgcg ccacatagca gaactttaaa agtgctcatc    5220
attggaaaac gttcttcggg gcgaaaactc tcaaggatct taccgctgtt gagatccagt    5280
tcgatgtaac ccactcgtgc acccaactga tcttcagcat cttttacttt caccagcgtt    5340
tctgggtgag caaaaacagg aaggcaaaat gccgcaaaaa agggaataag gcgacacgg     5400 aaatgttgaa tactcatact cttccttttt caatattatt gaagcattta tcagggttat    5460
tgtctcatga gcggatacat atttgaatgt atttagaaaa ataaacaaat aggggttccg    5520
cgcacatttc cccgaaaagt gccacctgac gtctaagaaa ccattattat catgacatta    5580
acctataaaa ataggcgtat cacgaggccc tttcgtcttc aagaatttta taaaccgtgg    5640
agcgggcaat actgagctga tgagcaattt ccgttgcacc agtgcccttc tgatgaagcg    5700
tcagcacgac gttcctgtcc acggtacgcc tgcggccaaa tttgattcct ttcagctttg    5760
cttcctgtcg gccctcattc gtgcgctcta ggatcctcta cgccgacgc atcgtggccg     5820 gcatcaccgg cgctgaggtc tgcctcgtga agaaggtgtt gctgactcat accaggcctg    5880
aatcgcccca tcatccagcc agaaagtgag ggagccacgg ttgatgagag ctttgttgta    5940
ggtggaccag ttggtgattt tgaacttttg ctttgccacg gaacggtctg cgttgtcggg    6000
aagatgcgtg atctgatcct tcaactcagc aaaagttcga tttattcaac aaagccgccg    6060
tcccgtcaag tcagcgtaat gctctgccag tgttacaacc aattaaccaa ttctgattag    6120
aaaaactcat cgagcatcaa atgaaactgc aatttattca tatcaggatt atcaatacca    6180
tatttttgaa aaagccgttt ctgtaatgaa ggagaaaact caccgaggca gttccatagg    6240
atggcaagat cctggtatcg gtctgcgatt ccgactcgtc caacatcaat acaacctatt    6300
aatttcccct cgtcaaaaat aaggttatca agtgagaaat caccatgagt gacgactgaa    6360
tccggtgaga atggcagaat aggaacttcg aataggaac ttcaaagcgt ttccgaaaac      6420
gagcgcttcc gaaaatgcaa cgcgagctgc gcacatacag ctcactgttc acgtcgcacc    6480
tatatctgcg tgttgcctgt atatatatat acatgagaag aacggcatag tgcgtgttta    6540
tgcttaaatg cgtacttata tgcgtctatt tatgtaggat gaaaggtagt ctagtaccct    6600
ctgtgatatt atcccattcc atgcggggta tcgtatgctt ccttcagcac taccctttag    6660
ctgttctata tgctgccact cctcaattgg attagtctca tccttcaatg ctatcatttc    6720
ctttgatatt ggatcatatg catagtaccg agaaactagt gcgaagtagt gatcaggtat    6780
tgctgttatc tgatgagtat acgttgtcct ggccacggca aagcacgct tatcgctcca     6840 atttcccaca acattagtca actccgttag gcccttcatt gaaagaaatg aggtcatcaa    6900
```

```
atgtcttcca atgtgagatt ttgggccatt ttttatagca aagattgaat aaggcgcatt    6960
tttcttcaaa gctttattgt acgatctgac taagttatct tttaataatt ggtattcctg    7020
tttattgctt gaagaattgc cggtcctatt tactcgtttt aggactggtt cagaattcct    7080
caaaaattca tccaaatata caagtggatc gatcctaccc cttgcgctaa agaagtatat    7140
gtgcctacta acgcttgtct ttgtctctgt cactaaacac tggattatta ctcccagata    7200
cttattttgg actaatttaa atgatttcgg atcaacgttc ttaatatcgc tgaatcttcc    7260
acaattgatg aaagtagcta ggaagaggaa ttggtataaa gttttgtttt ttgtaaatct    7320
cgaagtatac tcaaacgaat ttagtatttt ctcagtgatc tcccagatgc tttcaccctc    7380
acttagaagt gctttaagca ttttttttact gtggctattt cccttatctg cttcttccga    7440
tgattcgaac tgtaattgca aactacttac aatatcagtg atatcagatt gatgtttttg    7500
tccatagtaa ggataattg taaattccca agcaggaatc aatttcttta atgaggcttc    7560
cagaattgtt gcttttttgcg tcttgtattt aaactggagt gatttattga caatatcgaa    7620
actcagcgaa ttgcttatga tagtattata gctcatgaat gtggctctct tgattgctgt    7680
tccgttatgt gtaatcatcc aacataaata ggttagttca gcagcacata atgctatttt    7740
ctcacctgaa ggtctttcaa acctttccac aaactgacga acaagcacct taggtggtgt    7800
tttacataat atatcaaatt gtggcataca acctccttag tacatgcaac cattatcacc    7860
gccagaggta aaatagtcaa cacgcacggt gttagatatt tatcccttgc ggtgatagat    7920
ttaacgtatg agcacaaaaa agaaaccatt aacacaagag cagcttgagg acgcacgtcg    7980
ccttaaagca atttatgaaa aaaagaaaaa tgaacttggc ttatcccagg aatctgtcgc    8040
agacaagatg gggatggggc agtcaggcgt tggtgcttta tttaatggca tcaatgcatt    8100
aaatgcttat aacgccgcat tgcttacaaa aattctcaaa gttagcgttg aagaatttag    8160
cccttcaatc gccagagaaa tctacgagat gtatgaagcg gttagtatgc agccgtcact    8220
tagaagtgag tatgagtacc ctgttttttc tcatgttcag gcagggatgt tctcacctaa    8280
gcttagaacc tttaccaaag gtgatgcgga gagatgggta agcacaacca aaaaagccag    8340
tgattctgca ttctggcttg aggttgaagg taattccatg accgcaccaa caggctccaa    8400
gccaagcttt cctgacggaa tgttaattct cgttgaccct gagcaggctg ttgagccagg    8460
tgatttctgc atagccagac ttgggggtga tgagtttacc ttcaagaaac tgatcaggga    8520
tagcggtcag gtgttttttac aaccactaaa cccacagtac ccaatgatcc catgcaatga    8580
gagttgttcc gttgtgggga aagttatcgc tagtcagtgg cctgaagaga cgtttggctg    8640
atcggcaagg tgttctggtc ggcgcatagc tgataacaat tgagcaagaa tctgcatttc    8700
tttccagact tgttcaacag gccagccatt acgctcgtca tcaaaatcac tcgcatcaac    8760
caaaccgtta ttcattcgtg attgcgcctg agcgagacga aatacgcgat cgctgttaaa    8820
aggacaatta caaacaggaa tcgaatgcaa ccggcgcagg aacactgcca gcgcatcaac    8880
aatattttca cctgaatcag gatattcttc taatacctgg aatgctgttt tcccggggat    8940
cgcagtggtg agtaaccatg catcatcagg agtacggata aaatgcttga tggtcggaag    9000
aggcataaat tccgtcagcc agtttagtct gaccatctca tctgtaacat cattggcaac    9060
gctacctttg ccatgtttca gaaacaactc tggcgcatcg gcttccat acaatcgata    9120 gattgtcgca cctgattgcc cgacattatc gcgagcccat ttatacccat ataaatcagc    9180
atccatgttg gaatttaatc gcggcctcga gcaagacgtt tccgttgaa tatggctcat    9240 aacaccccct gtattactgt ttatgtaagc agacagtttt attgttcatg atgatatatt    9300
```

```
tttatcttgt gcaatgtaac atcagagatt tt                              9332

<210> SEQ ID NO 46
<211> LENGTH: 80
<212> TYPE: DNA
<213> ORGANISM: Artificial Sequence
<220> FEATURE:
<223> OTHER INFORMATION: Primer

<400> SEQUENCE: 46
atgtcgcaac ataacgaaaa gaacccacat cagcaccagt caccactaca cgattccagc    60
gtgtaggctg gagctgcttc                                                80

<210> SEQ ID NO 47
<211> LENGTH: 82
<212> TYPE: DNA
<213> ORGANISM: Artificial Sequence
<220> FEATURE:
<223> OTHER INFORMATION: Primer

<400> SEQUENCE: 47
ttacgccggg attttgtcaa tcttaggaat gcgtgaccac acgcggtgtg ctgtcatcag    60
attccgggga tccgtcgacc tg                                             82

<210> SEQ ID NO 48
<211> LENGTH: 1424
<212> TYPE: DNA
<213> ORGANISM: Artificial Sequence
<220> FEATURE:
<223> OTHER INFORMATION: Synthetic construct

<400> SEQUENCE: 48
ttacgccggg attttgtcaa tcttaggaat gcgtgaccac acgcggtgtg ctgtcatcag    60
attccgggga tccgtcgacc tgcagttcga agttcctatt ctctagaaag tataggaact   120
tcagagcgct tttgaagctc acgctgccgc aagcactcag ggcgcaaggg ctgctaaagg   180
aagcggaaca cgtagaaagc cagtccgcag aaacggtgct gaccccggat gaatgtcagc   240
tactgggcta tctggacaag ggaaaacgca agcgcaaaga gaaagcaggt agcttgcagt   300
gggcttacat ggcgatagct agactgggcg gttttatgga cagcaagcga accggaattg   360
ccagctgggg cgccctctgg taaggttggg aagccctgca aagtaaactg gatggctttc   420
ttgccgccaa ggatctgatg gcgcagggga tcaagatctg atcaagagac aggatgagga   480
tcgtttcgca tgattgaaca agatggattg cacgcaggtt ctccggccgc ttgggtggag   540
aggctattcg gctatgactg gcacaacaga caatcggct gctctgatgc cgccgtgttc    600
cggctgtcag cgcaggggcg cccggttctt tttgtcaaga ccgacctgtc cggtgccctg   660
aatgaactgc aggacgaggc agcgcggcta tcgtggctgg ccacgacggg cgttccttgc   720
gcagctgtgc tcgacgttgt cactgaagcg ggaagggact ggctgctatt gggcgaagtg   780
ccggggcagg atctcctgtc atctcacctt gctcctgccg agaaagtatc catcatggct   840
gatgcaatgc ggcggctgca tacgcttgat ccggctacct gcccattcga ccaccaagcg   900
aaacatcgca tcgagcgagc acgtactcgg atggaagccg gtcttgtcga tcaggatgat   960
ctggacgaag agcatcaggg gctcgcgcca gccgaactgt tcgccaggct caaggcgcgc  1020
atgcccgacg gcgaggatct cgtcgtgacc catggcgatg cctgcttgcc gaatatcatg  1080
gtggaaaatg gccgcttttc tggattcatc gactgtggcc ggctgggtgt ggcggaccgc  1140
tatcaggaca tagcgttggc tacccgtgat attgctgaag agcttggcgg cgaatgggct  1200
```

```
gaccgcttcc tcgtgcttta cggtatcgcc gctcccgatt cgcagcgcat cgccttctat    1260
cgccttcttg acgagttctt ctaataaggg gatcttgaag ttcctattcc gaagttccta    1320
ttctctagaa agtataggaa cttcgaagca gctccagcct acacgctgga atcgtgtagt    1380
ggtgactggt gctgatgtgg gttcttttcg ttatgttgcg acat                     1424
```

<210> SEQ ID NO 49
<211> LENGTH: 2262
<212> TYPE: DNA
<213> ORGANISM: Escherichia coli
<220> FEATURE:
<221> NAME/KEY: CDS
<222> LOCATION: (1)..(2262)

<400> SEQUENCE: 49

```
atg tcg caa cat aac gaa aag aac cca cat cag cac cag tca cca cta     48
Met Ser Gln His Asn Glu Lys Asn Pro His Gln His Gln Ser Pro Leu
1               5                   10                  15 cac gat tcc agc gaa gcg aaa ccg ggg atg gac tca ctg gca cct gag     96
His Asp Ser Ser Glu Ala Lys Pro Gly Met Asp Ser Leu Ala Pro Glu
                20                  25                  30 gac ggc tct cat cgt cca gcg gct gaa cca aca ccg cca ggt gca caa    144
Asp Gly Ser His Arg Pro Ala Ala Glu Pro Thr Pro Pro Gly Ala Gln
            35                  40                  45 cct acc gcc cca ggg agc ctg aaa gcc cct gat acg cgt aac gaa aaa    192
Pro Thr Ala Pro Gly Ser Leu Lys Ala Pro Asp Thr Arg Asn Glu Lys
        50                  55                  60 ctt aat tct ctg gaa gac gta cgc aaa ggc agt gaa aat tat gcg ctg    240
Leu Asn Ser Leu Glu Asp Val Arg Lys Gly Ser Glu Asn Tyr Ala Leu
65                  70                  75                  80 acc act aat cag ggc gtg cgc atc gcc gac gat caa aac tca ctg cgt    288
Thr Thr Asn Gln Gly Val Arg Ile Ala Asp Asp Gln Asn Ser Leu Arg
                85                  90                  95 gcc ggt agc cgt ggt cca acg ctg ctg gaa gat ttt att ctg cgc gag    336
Ala Gly Ser Arg Gly Pro Thr Leu Leu Glu Asp Phe Ile Leu Arg Glu
                100                 105                 110 aaa atc acc cac ttt gac cat gag cgc att ccg gaa cgt att gtt cat    384
Lys Ile Thr His Phe Asp His Glu Arg Ile Pro Glu Arg Ile Val His
            115                 120                 125 gca cgc gga tca gcc gct cac ggt tat ttc cag cca tat aaa agc tta    432
Ala Arg Gly Ser Ala Ala His Gly Tyr Phe Gln Pro Tyr Lys Ser Leu
        130                 135                 140 agc gat att acc aaa gcg gat ttc ctc tca gat ccg aac aaa atc acc    480
Ser Asp Ile Thr Lys Ala Asp Phe Leu Ser Asp Pro Asn Lys Ile Thr
145                 150                 155                 160 cca gta ttt gta cgt ttc tct acc gtt cag ggt ggt gct ggc tct gct    528
Pro Val Phe Val Arg Phe Ser Thr Val Gln Gly Gly Ala Gly Ser Ala
                165                 170                 175 gat acc gtg cgt gat atc cgt ggc ttt gcc acc aag ttc tat acc gaa    576
Asp Thr Val Arg Asp Ile Arg Gly Phe Ala Thr Lys Phe Tyr Thr Glu
                180                 185                 190 gag ggt att ttt gac ctc gtt ggc aat aac acg cca atc ttc ttt atc    624
Glu Gly Ile Phe Asp Leu Val Gly Asn Asn Thr Pro Ile Phe Phe Ile
            195                 200                 205 cag gat gcg cat aaa ttc ccc gat ttt gtt cat gcg gta aaa cca gaa    672
Gln Asp Ala His Lys Phe Pro Asp Phe Val His Ala Val Lys Pro Glu
        210                 215                 220 ccg cac tgg gca att cca caa ggg caa agt gcc cac gat act ttc tgg    720
Pro His Trp Ala Ile Pro Gln Gly Gln Ser Ala His Asp Thr Phe Trp
225                 230                 235                 240
```

```
gat tat gtt tct ctg caa cct gaa act ctg cac aac gtg atg tgg gcg      768
Asp Tyr Val Ser Leu Gln Pro Glu Thr Leu His Asn Val Met Trp Ala
            245                 250                 255 atg tcg gat cgc ggc atc ccc cgc agt tac cgc acc atg gaa ggc ttc      816
Met Ser Asp Arg Gly Ile Pro Arg Ser Tyr Arg Thr Met Glu Gly Phe
        260                 265                 270 ggt att cac acc ttc cgc ctg att aat gcc gaa ggg aag gca acg ttt      864
Gly Ile His Thr Phe Arg Leu Ile Asn Ala Glu Gly Lys Ala Thr Phe
            275                 280                 285 gta cgt ttc cac tgg aaa cca ctg gca ggt aaa gcc tca ctc gtt tgg      912
Val Arg Phe His Trp Lys Pro Leu Ala Gly Lys Ala Ser Leu Val Trp
        290                 295                 300 gat gaa gca caa aaa ctc acc gga cgt gac ccg gac ttc cac cgc cgc      960
Asp Glu Ala Gln Lys Leu Thr Gly Arg Asp Pro Asp Phe His Arg Arg
305                 310                 315                 320 gag ttg tgg gaa gcc att gaa gca ggc gat ttt ccg gaa tac gaa ctg     1008
Glu Leu Trp Glu Ala Ile Glu Ala Gly Asp Phe Pro Glu Tyr Glu Leu
                325                 330                 335 ggc ttc cag ttg att cct gaa gaa gat gaa ttc aag ttc gac ttc gat     1056
Gly Phe Gln Leu Ile Pro Glu Glu Asp Glu Phe Lys Phe Asp Phe Asp
            340                 345                 350 ctt ctc gat cca acc aaa ctt atc ccg gaa gaa ctg gtg ccc gtt cag     1104
Leu Leu Asp Pro Thr Lys Leu Ile Pro Glu Glu Leu Val Pro Val Gln
        355                 360                 365 cgt gtc ggc aaa atg gtg ctc aat cgc aac ccg gat aac ttc ttt gct     1152
Arg Val Gly Lys Met Val Leu Asn Arg Asn Pro Asp Asn Phe Phe Ala
    370                 375                 380 gaa aac gaa cag gcg gct ttc cat cct ggg cat atc gtg ccg gga ctg     1200
Glu Asn Glu Gln Ala Ala Phe His Pro Gly His Ile Val Pro Gly Leu
385                 390                 395                 400 gac ttc acc aac gat ccg ctg ttg cag gga cgt ttg ttc tcc tat acc     1248
Asp Phe Thr Asn Asp Pro Leu Leu Gln Gly Arg Leu Phe Ser Tyr Thr
                405                 410                 415 gat aca caa atc agt cgt ctt ggt ggg ccg aat ttc cat gag att ccg     1296
Asp Thr Gln Ile Ser Arg Leu Gly Gly Pro Asn Phe His Glu Ile Pro
            420                 425                 430 att aac cgt ccg acc tgc cct tac cat aat ttc cag cgt gac ggc atg     1344
Ile Asn Arg Pro Thr Cys Pro Tyr His Asn Phe Gln Arg Asp Gly Met
        435                 440                 445 cat cgc atg ggg atc gac act aac ccg gcg aat tac gaa ccg aac tcg     1392
His Arg Met Gly Ile Asp Thr Asn Pro Ala Asn Tyr Glu Pro Asn Ser
    450                 455                 460 att aac gat aac tgg ccg cgc gaa aca ccg ccg ggg ccg aaa cgc ggc     1440
Ile Asn Asp Asn Trp Pro Arg Glu Thr Pro Pro Gly Pro Lys Arg Gly
465                 470                 475                 480 ggt ttt gaa tca tac cag gag cgc gtg gaa ggc aat aaa gtt cgc gag     1488
Gly Phe Glu Ser Tyr Gln Glu Arg Val Glu Gly Asn Lys Val Arg Glu
                485                 490                 495 cgc agc cca tcg ttt ggc gaa tat tat tcc cat ccg cgt ctg ttc tgg     1536
Arg Ser Pro Ser Phe Gly Glu Tyr Tyr Ser His Pro Arg Leu Phe Trp
            500                 505                 510 cta agt cag acg cca ttt gag cag cgc cat att gtc gat ggt ttc agt     1584
Leu Ser Gln Thr Pro Phe Glu Gln Arg His Ile Val Asp Gly Phe Ser
        515                 520                 525 ttt gag tta agc aaa gtc gtt cgt ccg tat att cgt gag cgc gtt gtt     1632
Phe Glu Leu Ser Lys Val Val Arg Pro Tyr Ile Arg Glu Arg Val Val
    530                 535                 540 gac cag ctg gcg cat att gat ctc act ctg gcc cag gcg gtg gcg aaa     1680
Asp Gln Leu Ala His Ile Asp Leu Thr Leu Ala Gln Ala Val Ala Lys
545                 550                 555                 560
```

```
aat ctc ggt atc gaa ctg act gac gac cag ctg aat atc acc cca cct   1728
Asn Leu Gly Ile Glu Leu Thr Asp Asp Gln Leu Asn Ile Thr Pro Pro
            565                 570                 575 ccg gac gtc aac ggt ctg aaa aag gat cca tcc tta agt ttg tac gcc   1776
Pro Asp Val Asn Gly Leu Lys Lys Asp Pro Ser Leu Ser Leu Tyr Ala
        580                 585                 590 att cct gac ggt gat gtg aaa ggt cgc gtg gta gcg att tta ctt aat   1824
Ile Pro Asp Gly Asp Val Lys Gly Arg Val Val Ala Ile Leu Leu Asn
    595                 600                 605 gat gaa gtg aga tcg gca gac ctt ctg gcc att ctc aag gcg ctg aag   1872
Asp Glu Val Arg Ser Ala Asp Leu Leu Ala Ile Leu Lys Ala Leu Lys
610                 615                 620 gcc aaa ggc gtt cat gcc aaa ctg ctc tac tcc cga atg ggt gaa gtg   1920
Ala Lys Gly Val His Ala Lys Leu Leu Tyr Ser Arg Met Gly Glu Val
625                 630                 635                 640 act gcg gat gac ggt acg gtg ttg cct ata gcc gct acc ttt gcc ggt   1968
Thr Ala Asp Asp Gly Thr Val Leu Pro Ile Ala Ala Thr Phe Ala Gly
            645                 650                 655 gca cct tcg ctg acg gtc gat gcg gtc att gtc cct tgc ggc aat atc   2016
Ala Pro Ser Leu Thr Val Asp Ala Val Ile Val Pro Cys Gly Asn Ile
        660                 665                 670 gcg gat atc gct gac aac ggc gat gcc aac tac tac ctg atg gaa gcc   2064
Ala Asp Ile Ala Asp Asn Gly Asp Ala Asn Tyr Tyr Leu Met Glu Ala
    675                 680                 685 tac aaa cac ctt aaa ccg att gcg ctg gcg ggt gac gcg cgc aag ttt   2112
Tyr Lys His Leu Lys Pro Ile Ala Leu Ala Gly Asp Ala Arg Lys Phe
690                 695                 700 aaa gca aca atc aag atc gct gac cag ggt gaa gaa ggg att gtg gaa   2160
Lys Ala Thr Ile Lys Ile Ala Asp Gln Gly Glu Glu Gly Ile Val Glu
705                 710                 715                 720 gct gac agc gct gac ggt agt ttt atg gat gaa ctg cta acg ctg atg   2208
Ala Asp Ser Ala Asp Gly Ser Phe Met Asp Glu Leu Leu Thr Leu Met
            725                 730                 735 gca gca cac cgc gtg tgg tca cgc att cct aag att gac aaa att cct   2256
Ala Ala His Arg Val Trp Ser Arg Ile Pro Lys Ile Asp Lys Ile Pro
        740                 745                 750 gcc tga                                                           2262
Ala

<210> SEQ ID NO 50
<211> LENGTH: 753
<212> TYPE: PRT
<213> ORGANISM: Escherichia coli

<400> SEQUENCE: 50

Met Ser Gln His Asn Glu Lys Asn Pro His Gln His Gln Ser Pro Leu
1               5                   10                  15

His Asp Ser Ser Glu Ala Lys Pro Gly Met Asp Ser Leu Ala Pro Glu
            20                  25                  30

Asp Gly Ser His Arg Pro Ala Ala Glu Pro Thr Pro Pro Gly Ala Gln
        35                  40                  45

Pro Thr Ala Pro Gly Ser Leu Lys Ala Pro Asp Thr Arg Asn Glu Lys
    50                  55                  60

Leu Asn Ser Leu Glu Asp Val Arg Lys Gly Ser Glu Asn Tyr Ala Leu
65                  70                  75                  80

Thr Thr Asn Gln Gly Val Arg Ile Ala Asp Asp Gln Asn Ser Leu Arg
                85                  90                  95

Ala Gly Ser Arg Gly Pro Thr Leu Leu Glu Asp Phe Ile Leu Arg Glu
            100                 105                 110
```

-continued

```
Lys Ile Thr His Phe Asp His Glu Arg Ile Pro Glu Arg Ile Val His
        115                 120                 125

Ala Arg Gly Ser Ala Ala His Gly Tyr Phe Gln Pro Tyr Lys Ser Leu
    130                 135                 140

Ser Asp Ile Thr Lys Ala Asp Phe Leu Ser Asp Pro Asn Lys Ile Thr
145                 150                 155                 160

Pro Val Phe Val Arg Phe Ser Thr Val Gln Gly Gly Ala Gly Ser Ala
                165                 170                 175

Asp Thr Val Arg Asp Ile Arg Gly Phe Ala Thr Lys Phe Tyr Thr Glu
                180                 185                 190

Glu Gly Ile Phe Asp Leu Val Gly Asn Asn Thr Pro Ile Phe Phe Ile
            195                 200                 205

Gln Asp Ala His Lys Phe Pro Asp Phe Val His Ala Val Lys Pro Glu
        210                 215                 220

Pro His Trp Ala Ile Pro Gln Gly Gln Ser Ala His Asp Thr Phe Trp
225                 230                 235                 240

Asp Tyr Val Ser Leu Gln Pro Glu Thr Leu His Asn Val Met Trp Ala
                245                 250                 255

Met Ser Asp Arg Gly Ile Pro Arg Ser Tyr Arg Thr Met Glu Gly Phe
            260                 265                 270

Gly Ile His Thr Phe Arg Leu Ile Asn Ala Glu Gly Lys Ala Thr Phe
        275                 280                 285

Val Arg Phe His Trp Lys Pro Leu Ala Gly Lys Ala Ser Leu Val Trp
    290                 295                 300

Asp Glu Ala Gln Lys Leu Thr Gly Arg Asp Pro Asp Phe His Arg Arg
305                 310                 315                 320

Glu Leu Trp Glu Ala Ile Glu Ala Gly Asp Phe Pro Glu Tyr Glu Leu
                325                 330                 335

Gly Phe Gln Leu Ile Pro Glu Glu Asp Glu Phe Lys Phe Asp Phe Asp
            340                 345                 350

Leu Leu Asp Pro Thr Lys Leu Ile Pro Glu Glu Leu Val Pro Val Gln
        355                 360                 365

Arg Val Gly Lys Met Val Leu Asn Arg Asn Pro Asp Asn Phe Phe Ala
    370                 375                 380

Glu Asn Glu Gln Ala Ala Phe His Pro Gly His Ile Val Pro Gly Leu
385                 390                 395                 400

Asp Phe Thr Asn Asp Pro Leu Leu Gln Gly Arg Leu Phe Ser Tyr Thr
                405                 410                 415

Asp Thr Gln Ile Ser Arg Leu Gly Gly Pro Asn Phe His Glu Ile Pro
            420                 425                 430

Ile Asn Arg Pro Thr Cys Pro Tyr His Asn Phe Gln Arg Asp Gly Met
        435                 440                 445

His Arg Met Gly Ile Asp Thr Asn Pro Ala Asn Tyr Glu Pro Asn Ser
    450                 455                 460

Ile Asn Asp Asn Trp Pro Arg Glu Thr Pro Pro Gly Pro Lys Arg Gly
465                 470                 475                 480

Gly Phe Glu Ser Tyr Gln Glu Arg Val Glu Gly Asn Lys Val Arg Glu
                485                 490                 495

Arg Ser Pro Ser Phe Gly Glu Tyr Tyr Ser His Pro Arg Leu Phe Trp
            500                 505                 510

Leu Ser Gln Thr Pro Phe Glu Gln Arg His Ile Val Asp Gly Phe Ser
        515                 520                 525

Phe Glu Leu Ser Lys Val Val Arg Pro Tyr Ile Arg Glu Arg Val Val
    530                 535                 540
```

-continued

```
Asp Gln Leu Ala His Ile Asp Leu Thr Leu Ala Gln Ala Val Ala Lys
545                 550                 555                 560

Asn Leu Gly Ile Glu Leu Thr Asp Asp Gln Leu Asn Ile Thr Pro Pro
            565                 570                 575

Pro Asp Val Asn Gly Leu Lys Lys Asp Pro Ser Leu Ser Leu Tyr Ala
        580                 585                 590

Ile Pro Asp Gly Asp Val Lys Gly Arg Val Val Ala Ile Leu Leu Asn
    595                 600                 605

Asp Glu Val Arg Ser Ala Asp Leu Leu Ala Ile Leu Lys Ala Leu Lys
610                 615                 620

Ala Lys Gly Val His Ala Lys Leu Leu Tyr Ser Arg Met Gly Glu Val
625                 630                 635                 640

Thr Ala Asp Asp Gly Thr Val Leu Pro Ile Ala Ala Thr Phe Ala Gly
                645                 650                 655

Ala Pro Ser Leu Thr Val Asp Ala Val Ile Val Pro Cys Gly Asn Ile
            660                 665                 670

Ala Asp Ile Ala Asp Asn Gly Asp Ala Asn Tyr Tyr Leu Met Glu Ala
        675                 680                 685

Tyr Lys His Leu Lys Pro Ile Ala Leu Ala Gly Asp Ala Arg Lys Phe
    690                 695                 700

Lys Ala Thr Ile Lys Ile Ala Asp Gln Gly Glu Gly Ile Val Glu
705                 710                 715                 720

Ala Asp Ser Ala Asp Gly Ser Phe Met Asp Glu Leu Leu Thr Leu Met
                725                 730                 735

Ala Ala His Arg Val Trp Ser Arg Ile Pro Lys Ile Asp Lys Ile Pro
            740                 745                 750

Ala

<210> SEQ ID NO 51
<211> LENGTH: 25
<212> TYPE: DNA
<213> ORGANISM: Artificial Sequence
<220> FEATURE:
<223> OTHER INFORMATION: Primer

<400> SEQUENCE: 51
gatctgactg gtggtctata gttag                                        25

<210> SEQ ID NO 52
<211> LENGTH: 25
<212> TYPE: DNA
<213> ORGANISM: Artificial Sequence
<220> FEATURE:
<223> OTHER INFORMATION: Primer

<400> SEQUENCE: 52
gtagttatca tgatgtgtaa gtaag                                        25

<210> SEQ ID NO 53
<211> LENGTH: 182
<212> TYPE: PRT
<213> ORGANISM: Bacillus subtilis

<400> SEQUENCE: 53

Arg Gly Gln Gln Ser Ser Glu Asp Thr Ser Ile Ser Leu His Gly His
1               5                   10                  15

Ala Leu Gly Trp Met Thr Lys Gly Ile Leu Asp Lys Asp Thr Tyr Tyr
            20                  25                  30
```

```
Tyr Arg Gly Val Tyr Leu Asp Ala Val Arg Ala Leu Glu Val Ile Ser
        35                  40                  45

Ser Phe Asp Glu Val Asp Thr Arg Ile Gly Val Thr Gly Gly Ser
    50                  55                  60

Gln Gly Gly Gly Leu Thr Ile Ala Ala Ala Leu Ser Asp Ile Pro
 65                  70                  75                  80

Lys Ala Ala Val Ala Asp Tyr Pro Tyr Leu Ser Asn Phe Glu Arg Ala
                85                  90                  95

Ile Asp Val Ala Leu Glu Gln Pro Tyr Leu Glu Ile Asn Ser Phe Phe
                100                 105                 110

Arg Arg Asn Gly Ser Pro Glu Thr Glu Val Gln Ala Met Lys Thr Leu
                115                 120                 125

Ser Tyr Phe Asp Ile Met Asn Leu Ala Asp Arg Val Lys Val Pro Val
    130                 135                 140

Leu Met Ser Ile Gly Leu Ile Asp Lys Val Thr Pro Pro Ser Thr Val
145                 150                 155                 160

Phe Ala Ala Tyr Asn His Leu Glu Thr Glu Lys Glu Leu Lys Val Tyr
                165                 170                 175

Arg Tyr Phe Gly His Glu
                180

<210> SEQ ID NO 54
<211> LENGTH: 320
<212> TYPE: PRT
<213> ORGANISM: Thermoanaerobacterium saccharolyticum

<400> SEQUENCE: 54

Met Gly Leu Phe Asp Met Pro Leu Gln Lys Leu Arg Glu Tyr Thr Gly
 1               5                  10                  15

Thr Asn Pro Cys Pro Glu Asp Phe Asp Glu Tyr Trp Asp Arg Ala Leu
                20                  25                  30

Asp Glu Met Arg Ser Val Asp Pro Lys Ile Lys Met Lys Lys Ser Ser
                35                  40                  45

Phe Gln Val Pro Phe Ala Glu Cys Tyr Asp Leu Tyr Phe Thr Gly Val
    50                  55                  60

Arg Gly Ala Arg Ile His Ala Lys Tyr Ile Arg Pro Lys Thr Glu Gly
 65                  70                  75                  80

Lys His Pro Ala Leu Ile Arg Phe His Gly Tyr Ser Ser Asn Ser Gly
                85                  90                  95

Asp Trp Asn Asp Lys Leu Asn Tyr Val Ala Ala Gly Phe Thr Val Val
                100                 105                 110

Ala Met Asp Ala Arg Gly Gln Gly Gly Gln Ser Gln Asp Val Gly Gly
                115                 120                 125

Val Asn Gly Asn Thr Leu Asn Gly His Ile Ile Arg Gly Leu Asp Asp
    130                 135                 140

Asp Ala Asp Asn Met Leu Phe Arg His Ile Phe Leu Asp Thr Ala Gln
145                 150                 155                 160

Leu Ala Gly Ile Val Met Asn Met Pro Glu Ile Asp Glu Asp Arg Val
                165                 170                 175

Ala Val Met Gly Pro Ser Gln Gly Gly Gly Leu Ser Leu Ala Cys Ala
                180                 185                 190

Ala Leu Glu Pro Lys Ile Arg Lys Val Val Ser Glu Tyr Pro Phe Leu
    195                 200                 205

Ser Asp Tyr Lys Arg Val Trp Asp Leu Asp Leu Ala Lys Asn Ala Tyr
    210                 215                 220
```

Gln Glu Ile Thr Asp Tyr Phe Arg Leu Phe Asp Pro Arg His Glu Arg
225                 230                 235                 240

Glu Asn Glu Val Phe Thr Lys Leu Gly Tyr Ile Asp Val Lys Asn Leu
            245                 250                 255

Ala Lys Arg Ile Lys Gly Asp Val Leu Met Cys Val Gly Leu Met Asp
        260                 265                 270

Gln Val Cys Pro Pro Ser Thr Val Phe Ala Ala Tyr Asn Asn Ile Gln
    275                 280                 285

Ser Lys Lys Asp Ile Lys Val Tyr Pro Asp Tyr Gly His Glu Pro Met
290                 295                 300

Arg Gly Phe Gly Asp Leu Ala Met Gln Phe Met Leu Glu Leu Tyr Ser
305                 310                 315                 320

<210> SEQ ID NO 55
<211> LENGTH: 981
<212> TYPE: DNA
<213> ORGANISM: Thermotoga lettingae

<400> SEQUENCE: 55

```
atggtctatt ttgatatgcc attggaagat tgagaaaaat atctgccaca gaggtacgaa     60
gaaaaggatt tcgatgattt ctggaaacaa acaatccatg aaacaagggg atattttcaa    120
gaaccaattc tcaaaaaagt ggatttttat ttgcagaatg ttgagacttt tgatgtgact    180
ttctctggtt acagaggtca gaagataaaa ggatggttga ttttgccaaa attcagaaat    240
gggaaattac cctgcgtagt tgaatttgtt ggttatggag gaggaagagg atttccatat    300
gactggctgc tttggagtgc ggcaggatac gcacatttca taatggacac gagaggacaa    360
ggtagcaact ggatgaaggg tgatacacca gattatgaag ataatccttc agatccacaa    420
tatccaggct ttctgacaaa aggagtactg aacccggaaa cttattatta caggagagtt    480
tttatggatg catttatggc tgttgaaact atcagccaac ttgaacaaat agattcacaa    540
accataatat tatcaggtgc aagccagggt ggtggaatag ctttggctgt gagtgcattg    600
tcttcaaagg tcatggctct actttgtgat gttcccttc tgtgtcatta caaagagca     660
gttcagataa cagattcaat gccctatgca gaaattacga gatattgcaa aactcacatt    720
gacaaaatcc aaacagtatt cagaacctc tcttattttg acggcgtcaa ttttgcagct    780
cgtgcaaat gccctgcttt gttttcggtg ggactcatgg acgacatttg cccaccttca    840
acagttttg ccgcttacaa ttattacgct ggtgagaaag atattagaat ttacccatac    900
aacaaccatg aaggcggtgg ttccttccat acactggaaa aattgaaatt tgtgaaaaaa    960
acaatttcta tgagagagtg a                                              981
```

<210> SEQ ID NO 56
<211> LENGTH: 326
<212> TYPE: PRT
<213> ORGANISM: Thermotoga lettingae

<400> SEQUENCE: 56

Met Val Tyr Phe Asp Met Pro Leu Glu Asp Leu Arg Lys Tyr Leu Pro
1               5                   10                  15

Gln Arg Tyr Glu Glu Lys Asp Phe Asp Asp Phe Trp Lys Gln Thr Ile
            20                  25                  30

His Glu Thr Arg Gly Tyr Phe Gln Glu Pro Ile Leu Lys Lys Val Asp
        35                  40                  45

Phe Tyr Leu Gln Asn Val Glu Thr Phe Asp Val Thr Phe Ser Gly Tyr
    50                  55                  60

```
Arg Gly Gln Lys Ile Lys Gly Trp Leu Ile Leu Pro Lys Phe Arg Asn
 65                  70                  75                  80

Gly Lys Leu Pro Cys Val Val Glu Phe Val Gly Tyr Gly Gly Gly Arg
                 85                  90                  95

Gly Phe Pro Tyr Asp Trp Leu Leu Trp Ser Ala Ala Tyr Ala His
            100                 105                 110

Phe Ile Met Asp Thr Arg Gly Gln Gly Ser Asn Trp Met Lys Gly Asp
        115                 120                 125

Thr Pro Asp Tyr Glu Asp Asn Pro Ser Asp Pro Gln Tyr Pro Gly Phe
    130                 135                 140

Leu Thr Lys Gly Val Leu Asn Pro Glu Thr Tyr Tyr Arg Arg Val
145                 150                 155                 160

Phe Met Asp Ala Phe Met Ala Val Glu Thr Ile Ser Gln Leu Glu Gln
                165                 170                 175

Ile Asp Ser Gln Thr Ile Ile Leu Ser Gly Ala Ser Gln Gly Gly Gly
            180                 185                 190

Ile Ala Leu Ala Val Ser Ala Leu Ser Ser Lys Val Met Ala Leu Leu
        195                 200                 205

Cys Asp Val Pro Phe Leu Cys His Tyr Lys Arg Ala Val Gln Ile Thr
    210                 215                 220

Asp Ser Met Pro Tyr Ala Glu Ile Thr Arg Tyr Cys Lys Thr His Ile
225                 230                 235                 240

Asp Lys Ile Gln Thr Val Phe Arg Thr Leu Ser Tyr Phe Asp Gly Val
                245                 250                 255

Asn Phe Ala Ala Arg Ala Lys Cys Pro Ala Leu Phe Ser Val Gly Leu
            260                 265                 270

Met Asp Asp Ile Cys Pro Pro Ser Thr Val Phe Ala Ala Tyr Asn Tyr
        275                 280                 285

Tyr Ala Gly Glu Lys Asp Ile Arg Ile Tyr Pro Tyr Asn Asn His Glu
    290                 295                 300

Gly Gly Gly Ser Phe His Thr Leu Glu Lys Leu Lys Phe Val Lys Lys
305                 310                 315                 320

Thr Ile Ser Met Arg Glu
                325

<210> SEQ ID NO 57
<211> LENGTH: 978
<212> TYPE: DNA
<213> ORGANISM: Thermotoga petrophilia

<400> SEQUENCE: 57
atggcctttt tcgatttacc actcgaagaa ctgaagaaat atcgtccaga gcggtacgaa      60
gagaaagact tcgatgagtt ctgggaaggg acactcgcag agaacgaaaa gttcccctta     120
gaccccgtct tcgagaggat ggagtctcac ctcaaaacag tcgaagcgta cgatgtaact     180
ttctccggat acatgggaca gaggatcaag gggtggctcc ttgttccaaa actggaagaa     240
gaaaaacttc cctgcgttgt gcagtacata ggatacaacg gtggaagagg attccctcac     300
gactggctgt tctggccttc tatgggttac atatgtttcg tcatggatac tcgaggacag     360
ggaagcggct ggatgaaagg agatacaccg gattaccctg aggatcccgt tgaccctcag     420
tatccaggat tcatgacaag aggaatactg gatcccagaa cttactacta cagacgagtc     480
ttcacggacg ctgtcagagc cgttgaagcg gctgcttctt ttcctcgggt agatcacgaa     540
agaatcgtga tagctggagg cagtcagggt ggcggaatag cccttgcggt gagcgctctc     600
tcaaagaaag caaaggctct tctgtgcgat gtgccgtttc tgtgtcactt cagaagggca     660
```

```
gtgcagcttg tggatacgca tccatacgcg gagatcacga actttctaaa gacccacagg    720
gacaaggaag aaatcgtgtt caggactctt tcctatttcg atggagtgaa cttcgcagtc    780
agagcgaaga tccctgcgct gttttctgtg ggtctcatgg acaacatttg tcctccttca    840 acggttttg  ctgcctacaa tcactacgct gggccgaagg aaatcagaat ctatccgtac    900
aacaaccacg agggaggagg ctcttccag  gcaattgaac aggtgaaatt cttgaagaga    960
ctatttgaga aaggctag                                                  978
```

<210> SEQ ID NO 58
<211> LENGTH: 325
<212> TYPE: PRT
<213> ORGANISM: Thermotoga petrophilia

<400> SEQUENCE: 58

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Gly Thr Leu
            20                  25                  30

Ala Glu Asn Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Met Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270

Met Asp Asn Ile Cys Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320
```

```
Leu Phe Glu Lys Gly
              325

<210> SEQ ID NO 59
<211> LENGTH: 978
<212> TYPE: DNA
<213> ORGANISM: Thermotoga sp.

<400> SEQUENCE: 59 atggccttttt tcgatttacc actcgaagaa ctgaagaaat accgtccgga gcggtacgaa      60
gagaaagact tcgatgagtt ctggaaagaa acactcgcag agagcgaaaa gtttcccctg     120
gaccccgtct tcgagaggat ggagtctcac ctcaaaacgg tcgaagtgta cgatgtcacc     180
ttctccggat acagaggaca gaggatcaag gggtggctcc ttgttccaaa attggaagaa     240
gaaaaacttc cctgcgttgt gcagtacata ggatacaacg gtggaagagg attccctcac     300
gactggctgt tctggccttc tatgggttac atatgtttcg tcatggatac tcgaggacag     360
ggaagcggct ggctgaaagg agatacaccg gattaccctg aggatcccgt tgaccctcag     420
tatccaggat tcatgacaag aggaatactg gatcccagaa cttactacta cagacgagtc     480
ttcacggacg ctgtcagagc cgttgaagcc gctgcttctt ttcctcgggt agatcacgaa     540
agaatcgtga tagctggagg cagtcagggt ggcggaatag cccttgcggt gagcgctctc     600
tcaaagaaag caaaggctct tctgtgcgat gtgccgtttc tgtgtcactt cagaagggca     660
gtgcagcttg tggatacgca tccatacgcg gagatcacga actttctaaa gactcacagg     720
gacaaggaag aaatcgtgtt caggactctt tcctatttcg atggagtgaa cttcgcagtc     780
agagcgaaga tccctgcgct gttttctgtg ggtctcatgg acaacatttg tcctccttca     840 acggttttttg ctgcctacaa tcactacgct gggccgaagg aaatcagaat ctatccgtac     900
aacaaccacg agggaggagg ctcttttccag gcaattgaac aggtgaaatt cttgaagaga     960
ctatttgaga aaggctag                                                  978

<210> SEQ ID NO 60
<211> LENGTH: 325
<212> TYPE: PRT
<213> ORGANISM: Thermotoga sp.

<400> SEQUENCE: 60

Met Ala Phe Phe Asp Leu Pro Leu Glu Glu Leu Lys Lys Tyr Arg Pro
  1               5                  10                  15

Glu Arg Tyr Glu Glu Lys Asp Phe Asp Glu Phe Trp Lys Glu Thr Leu
             20                  25                  30

Ala Glu Ser Glu Lys Phe Pro Leu Asp Pro Val Phe Glu Arg Met Glu
         35                  40                  45

Ser His Leu Lys Thr Val Glu Val Tyr Asp Val Thr Phe Ser Gly Tyr
     50                  55                  60

Arg Gly Gln Arg Ile Lys Gly Trp Leu Leu Val Pro Lys Leu Glu Glu
 65                  70                  75                  80

Glu Lys Leu Pro Cys Val Val Gln Tyr Ile Gly Tyr Asn Gly Gly Arg
                 85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Asp Pro Val Asp Pro Gln Tyr Pro Gly Phe
    130                 135                 140
```

```
Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Arg
            165                 170                 175

Val Asp His Glu Arg Ile Val Ile Ala Gly Ser Gln Gly Gly
        180                 185                 190

Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
        210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
            245                 250                 255

Asn Phe Ala Val Arg Ala Lys Ile Pro Ala Leu Phe Ser Val Gly Leu
            260                 265                 270

Met Asp Asn Ile Cys Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
        290                 295                 300

Gly Gly Gly Ser Phe Gln Ala Ile Glu Gln Val Lys Phe Leu Lys Arg
305                 310                 315                 320

Leu Phe Glu Lys Gly
                325

<210> SEQ ID NO 61
<211> LENGTH: 990
<212> TYPE: DNA
<213> ORGANISM: Thermotoga sp.

<400> SEQUENCE: 61
atggcgctat ttgatatgcc tctggaaaag ttaagatcat accttcccga tagatacgag      60
gaggaagatt tgatctgtt ctggaaagag actcttgagg agtcaagaaa attcccactg     120
gatcctattt ttgaaagagt agattatctg ctggagaacg tggaagtata cgatgtcacc     180
ttctccggtt acaggggtca agaataaaag gcgtggttga ttctaccggt tgttaagaag     240
gaagaaaggc ttccctgcat cgttgaattc ataggttaca ggggaggaag aggttttccc     300
ttcgattggc tcttctggag cagtgcgggg tatgcccatt cgtgatgga cactcgcggc     360
cagggaacca gtagagtaaa gggtgatact cctgactact gtgatgaacc ataaatcct      420
caattccccg gattcatgac gcggggaata ctggatccca ggacttacta ttacagaaga     480
gttttaccg atgctgtaag agcagtggaa accgcttcga gtttcccggg aatagatccc     540
gaaaggatag ccgtcgtggg aacaagccag ggtgggggaa ttgcattggc ggtggcggcg     600
cttttccgaaa ttccaaaggc tcttgtatcg aatgttccgt ttctgtgtca tttcagaaga     660
gcggttcaga taacagataa cgctccttac agtgagatag tgaattattt gaaagtccac     720
agagacaaag aggaaattgt gttcagaacg ctttcgtact ttgatggagt gactttgct      780
gcgagggcaa aaataccagc acttttctct gttgctctca tggacaaaac ctgtccacct     840
tctacagttt ttgctgctta caaccattac gctggtccaa agaaatcaa agtgtatcca      900
ttcaacgaac atgaaggtgg agaatctttc cagagaatgg aggaacttcg ctttatgaaa     960
aggattctaa aaggggaatt caaagcatga                                      990
```

```
<210> SEQ ID NO 62
<211> LENGTH: 329
<212> TYPE: PRT
<213> ORGANISM: Thermotoga sp.

<400> SEQUENCE: 62

Met Ala Leu Phe Asp Met Pro Leu Glu Lys Leu Arg Ser Tyr Leu Pro
1               5                   10                  15

Asp Arg Tyr Glu Glu Asp Phe Asp Leu Phe Trp Lys Glu Thr Leu
            20                  25                  30

Glu Glu Ser Arg Lys Phe Pro Leu Asp Pro Ile Phe Glu Arg Val Asp
        35                  40                  45

Tyr Leu Leu Glu Asn Val Glu Val Tyr Asp Val Thr Phe Ser Gly Tyr
    50                  55                  60

Arg Gly Gln Arg Ile Lys Ala Trp Leu Ile Leu Pro Val Val Lys Lys
65                  70                  75                  80

Glu Glu Arg Leu Pro Cys Ile Val Glu Phe Ile Gly Tyr Arg Gly Gly
                85                  90                  95

Arg Gly Phe Pro Phe Asp Trp Leu Phe Trp Ser Ser Ala Gly Tyr Ala
            100                 105                 110

His Phe Val Met Asp Thr Arg Gly Gln Gly Thr Ser Arg Val Lys Gly
        115                 120                 125

Asp Thr Pro Asp Tyr Cys Asp Glu Pro Ile Asn Pro Gln Phe Pro Gly
    130                 135                 140

Phe Met Thr Arg Gly Ile Leu Asp Pro Arg Thr Tyr Tyr Arg Arg
145                 150                 155                 160

Val Phe Thr Asp Ala Val Arg Ala Val Glu Thr Ala Ser Ser Phe Pro
                165                 170                 175

Gly Ile Asp Pro Glu Arg Ile Ala Val Val Gly Thr Ser Gln Gly Gly
            180                 185                 190

Gly Ile Ala Leu Ala Val Ala Ala Leu Ser Glu Ile Pro Lys Ala Leu
        195                 200                 205

Val Ser Asn Val Pro Phe Leu Cys His Phe Arg Arg Ala Val Gln Ile
    210                 215                 220

Thr Asp Asn Ala Pro Tyr Ser Glu Ile Val Asn Tyr Leu Lys Val His
225                 230                 235                 240

Arg Asp Lys Glu Glu Ile Val Phe Arg Thr Leu Ser Tyr Phe Asp Gly
                245                 250                 255

Val Asn Phe Ala Ala Arg Ala Lys Ile Pro Ala Leu Phe Ser Val Ala
            260                 265                 270

Leu Met Asp Lys Thr Cys Pro Pro Ser Thr Val Phe Ala Ala Tyr Asn
        275                 280                 285

His Tyr Ala Gly Pro Lys Glu Ile Lys Val Tyr Pro Phe Asn Glu His
    290                 295                 300

Glu Gly Gly Glu Ser Phe Gln Arg Met Glu Glu Leu Arg Phe Met Lys
305                 310                 315                 320

Arg Ile Leu Lys Gly Glu Phe Lys Ala
                325

<210> SEQ ID NO 63
<211> LENGTH: 48
<212> TYPE: DNA
<213> ORGANISM: Artificial Sequence
<220> FEATURE:
<223> OTHER INFORMATION: Synthetic construct

<400> SEQUENCE: 63
```

```
taactgcaga aggaggaata ggacatggcc ttcttcgatt taccactc        48
```

<210> SEQ ID NO 64
<211> LENGTH: 38
<212> TYPE: DNA
<213> ORGANISM: Artificial Sequence
<220> FEATURE:
<223> OTHER INFORMATION: Synthetic construct

<400> SEQUENCE: 64

```
tgatctagat tagcctttct caaatagttt tttcaaga                   38
```

<210> SEQ ID NO 65
<211> LENGTH: 1011
<212> TYPE: DNA
<213> ORGANISM: Artificial Sequence
<220> FEATURE:
<223> OTHER INFORMATION: Synthetic construct

<400> SEQUENCE: 65

```
taactgcaga aggaggaata ggacatggcc ttcttcgatt taccactcga agaactgaag    60
aaatatcgtc cagagcggta cgaagagaaa gacttcgatg agttctggga agagacactc   120
gcagagagcg aaaagttccc cttagacccc gtcttcgaga ggatggagtc tcacctcaaa   180
acagtcgaag cgtacgatgt caccttctcc ggatacaggg gacagaggat caaagggtgg   240
ctccttgttc caaaactgga agaagaaaaa cttccctgcg ttgtgcagta cataggatac   300
aacggtggaa gaggattccc tcacgactgg ctgttctggc cttctatggg ttacatatgt   360
ttcgtcatgg atactcgagg tcagggaagc ggctggctga aggagacac accggattac    420
cctgagggtc ccgttgaccc tcagtatcca ggattcatga caagaggaat actggatccc   480
agaacttact actacagacg agtcttcacg gacgctgtca gagccgttga agctgctgct   540
tcttttcctc aggtagatca agaaagaatc gtgatagctg gaggcagtca gggtggcgga   600
atagcccttg cggtgagcgc tctctcaaag aaagcaaagg ctcttctgtg cgatgtgccg   660
tttctgtgtc acttcagaag agcagtacag cttgtggata cgcatccata cgcggagatc   720
acgaactttc taaagaccca cagagacaag gaagaaatcg tgttcaggac tctttcctat   780
ttcgatggag tgaacttcgc agccagagcg aagatccctg cgctgttttc tgtgggtctc   840
atggacaaca tttgtcctcc ttcaacggtt ttcgctgcct acaattacta cgctggaccg   900
aaggaaatca gaatctatcc gtacaacaac cacgagggag gaggctcttt ccaagcggtt   960
gaacaggtga aattcttgaa aaaactattt gagaaaggct aatctagatc a            1011
```

<210> SEQ ID NO 66
<211> LENGTH: 24
<212> TYPE: DNA
<213> ORGANISM: Artificial Sequence
<220> FEATURE:
<223> OTHER INFORMATION: Primer

<400> SEQUENCE: 66

```
atggctttct tgacatgcc gctg                                   24
```

<210> SEQ ID NO 67
<211> LENGTH: 27
<212> TYPE: DNA
<213> ORGANISM: Artificial Sequence
<220> FEATURE:
<223> OTHER INFORMATION: Primer

<400> SEQUENCE: 67

```
ttagccttct tcgaacaggc gtttcag                                        27
```

<210> SEQ ID NO 68
<211> LENGTH: 978
<212> TYPE: DNA
<213> ORGANISM: Artificial Sequence
<220> FEATURE:
<223> OTHER INFORMATION: Synthetic construct

<400> SEQUENCE: 68

```
atggctttct ttgacatgcc gctggaagaa ctgaaaaagt accgtccgga acgttacgag    60
gaaaaagact tgacgaatt ttggcgcgaa accctgaaag aatccgaggg tttcccactg    120
gacccggtat ttgaaaaagt tgacttccac ctgaagaccg tcgaaactta cgacgtcacc   180
ttcagcggtt atcgtggcca gcgtatcaaa ggttggctgc tggtaccgaa actggcggaa   240
gagaaactgc cgtgtgttgt tcagtacatt ggttacaacg gtggccgtgg tttcccgcac   300
gactggctgt tctggccgtc tatgggttac atctgcttcg ttatggacac ccgtggtcag   360
ggtagcggtt ggatgaaggg tgatactccg gactacccgg aaggtccggt ggacccgcag   420
tacccgggct tcatgacgcg cggcatcctg atcctggca cctattacta ccgtcgtgtg    480
tttgtcgatg ccgtgcgcgc cgttgaagcc gctatcagct cccacgcgt cgattctcgt    540
aaagtggtag ttgctggtgg ctctcaaggt ggcggcattg cactggcagt tccgcgctg    600
tccaaccgtg ttaaagccct gctgtgcgat gttccgttcc tgtgccactt ccgtcgtgcg   660
gtacagctgg tggacaccca cccgtacgta gaaattacga cttcctgaa acccatcgt    720
gataaagaag agatcgtatt ccgtaccctg tcttactttg atggcgttaa ttttgcggct   780
cgtgcaaaag taccggcgct gttcagcgta ggtctgatgg acactatttg ccgccgtct   840
accgtattcg cagcctacaa ccactacgct ggtccgaaag aaatccgcat ctacccgtac   900
aacaaccacg aaggtggtgg ttcttccag gcaatcgaac aggttaaatt cctgaaacgc   960
ctgttcgaag aaggctaa                                                 978
```

<210> SEQ ID NO 69
<211> LENGTH: 325
<212> TYPE: PRT
<213> ORGANISM: Thermotoga neapolitana
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 69

```
Met Ala Phe Phe Asp Met Pro Leu Glu Glu Leu Lys Lys Tyr Arg Pro
1               5                   10                  15

Glu Arg Tyr Glu Glu Lys Asp Phe Asp Glu Phe Trp Arg Glu Thr Leu
            20                  25                  30

Lys Glu Ser Glu Gly Phe Pro Leu Asp Pro Val Phe Glu Lys Val Asp
        35                  40                  45

Phe His Leu Lys Thr Val Glu Thr Tyr Asp Val Thr Phe Ser Gly Tyr
    50                  55                  60

Arg Gly Gln Arg Ile Lys Gly Trp Leu Leu Val Pro Lys Leu Ala Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
```

```
                    115                 120                 125
Thr Pro Asp Tyr Pro Glu Gly Pro Val Asp Pro Gln Tyr Pro Gly Phe
            130                 135                 140

Met Thr Arg Gly Ile Leu Asp Pro Gly Thr Tyr Tyr Arg Arg Val
145                 150                 155                 160

Phe Val Asp Ala Val Arg Ala Val Glu Ala Ala Ile Ser Phe Pro Arg
                165                 170                 175

Val Asp Ser Arg Lys Val Val Ala Gly Ser Gln Gly Gly Gly
            180                 185                 190

Ile Ala Leu Ala Val Ser Ala Leu Ser Asn Arg Val Lys Ala Leu Leu
                195                 200                 205

Cys Asp Val Pro Phe Leu Cys His Phe Arg Arg Ala Val Gln Leu Val
            210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Val Pro Ala Leu Phe Ser Val Gly Leu
            260                 265                 270

Met Asp Thr Ile Xaa Pro Pro Ser Thr Val Phe Ala Ala Tyr Asn His
275                 280                 285

Tyr Ala Gly Pro Lys Glu Ile Arg Ile Tyr Pro Tyr Asn Asn His Glu
            290                 295                 300

Gly Gly Gly Ser Phe Gln Ala Ile Glu Gln Val Lys Phe Leu Lys Arg
305                 310                 315                 320

Leu Phe Glu Glu Gly
                325

<210> SEQ ID NO 70
<211> LENGTH: 325
<212> TYPE: PRT
<213> ORGANISM: Thermotoga maritima
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 70

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
                20                  25                  30

Ala Glu Ser Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
        50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140
```

```
Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
            165                 170                 175

Val Asp Gln Glu Arg Ile Val Ile Ala Gly Ser Gly Gly Gly
        180                 185                 190

Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
            210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Xaa Pro Pro Ser Thr Val Phe Ala Ala Tyr Asn Tyr
                275                 280                 285

Tyr Ala Gly Pro Lys Glu Ile Arg Ile Tyr Pro Tyr Asn Asn His Glu
            290                 295                 300

Gly Gly Gly Ser Phe Gln Ala Val Glu Val Lys Phe Leu Lys Lys
305                 310                 315                 320

Leu Phe Glu Lys Gly
                325

<210> SEQ ID NO 71
<211> LENGTH: 326
<212> TYPE: PRT
<213> ORGANISM: Thermotoga lettingae
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 71

Met Val Tyr Phe Asp Met Pro Leu Glu Asp Leu Arg Lys Tyr Leu Pro
1               5                   10                  15

Gln Arg Tyr Glu Glu Lys Asp Phe Asp Asp Phe Trp Lys Gln Thr Ile
            20                  25                  30

His Glu Thr Arg Gly Tyr Phe Gln Glu Pro Ile Leu Lys Lys Val Asp
        35                  40                  45

Phe Tyr Leu Gln Asn Val Glu Thr Phe Asp Val Thr Phe Ser Gly Tyr
50                  55                  60

Arg Gly Gln Lys Ile Lys Gly Trp Leu Ile Leu Pro Lys Phe Arg Asn
65                  70                  75                  80

Gly Lys Leu Pro Cys Val Val Glu Phe Val Gly Tyr Gly Gly Arg
                85                  90                  95

Gly Phe Pro Tyr Asp Trp Leu Leu Trp Ser Ala Ala Gly Tyr Ala His
            100                 105                 110

Phe Ile Met Asp Thr Arg Gly Gln Gly Ser Asn Trp Met Lys Gly Asp
        115                 120                 125

Thr Pro Asp Tyr Glu Asp Asn Pro Ser Asp Pro Gln Tyr Pro Gly Phe
130                 135                 140

Leu Thr Lys Gly Val Leu Asn Pro Glu Thr Tyr Tyr Arg Arg Val
145                 150                 155                 160

Phe Met Asp Ala Phe Met Ala Val Glu Thr Ile Ser Gln Leu Glu Gln
            165                 170                 175
```

```
Ile Asp Ser Gln Thr Ile Ile Leu Ser Gly Ala Ser Gln Gly Gly Gly
            180                 185                 190

Ile Ala Leu Ala Val Ser Ala Leu Ser Ser Lys Val Met Ala Leu Leu
            195                 200                 205

Cys Asp Val Pro Phe Leu Cys His Tyr Lys Arg Ala Val Gln Ile Thr
            210                 215                 220

Asp Ser Met Pro Tyr Ala Glu Ile Thr Arg Tyr Cys Lys Thr His Ile
225                 230                 235                 240

Asp Lys Ile Gln Thr Val Phe Arg Thr Leu Ser Tyr Phe Asp Gly Val
                245                 250                 255

Asn Phe Ala Ala Arg Ala Lys Cys Pro Ala Leu Phe Ser Val Gly Leu
            260                 265                 270

Met Asp Asp Ile Xaa Pro Pro Ser Thr Val Phe Ala Ala Tyr Asn Tyr
            275                 280                 285

Tyr Ala Gly Glu Lys Asp Ile Arg Ile Tyr Pro Tyr Asn Asn His Glu
            290                 295                 300

Gly Gly Gly Ser Phe His Thr Leu Glu Lys Leu Lys Phe Val Lys Lys
305                 310                 315                 320

Thr Ile Ser Met Arg Glu
                325

<210> SEQ ID NO 72
<211> LENGTH: 325
<212> TYPE: PRT
<213> ORGANISM: Thermotoga petrophilia
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 72

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Gly Thr Leu
            20                  25                  30

Ala Glu Asn Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
        50                  55                  60

Met Gly Gln Arg Ile Lys Gly Trp Leu Leu Val Pro Lys Leu Glu Glu
65              70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
            115                 120                 125

Thr Pro Asp Tyr Pro Glu Asp Pro Val Asp Pro Gln Tyr Pro Gly Phe
            130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Ser Gln Gly Gly Gly
            180                 185                 190

Ile Ala Leu Ala Val Ser Ala Leu Ser Lys Lys Ala Lys Ala Leu Leu
```

```
                    195                 200                 205
Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
                260                 265                 270

Met Asp Asn Ile Xaa Pro Pro Ser Thr Val Phe Ala Ala Tyr Asn His
            275                 280                 285

Tyr Ala Gly Pro Lys Glu Ile Arg Ile Tyr Pro Tyr Asn Asn His Glu
        290                 295                 300

Gly Gly Gly Ser Phe Gln Ala Ile Glu Gln Val Lys Phe Leu Lys Arg
305                 310                 315                 320

Leu Phe Glu Lys Gly
                325

<210> SEQ ID NO 73
<211> LENGTH: 325
<212> TYPE: PRT
<213> ORGANISM: Thermotoga sp.
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 73

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Lys Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Val Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220
```

-continued

```
Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270

Met Asp Asn Ile Xaa Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
        290                 295                 300

Gly Gly Gly Ser Phe Gln Ala Ile Glu Gln Val Lys Phe Leu Lys Arg
305                 310                 315                 320

Leu Phe Glu Lys Gly
                325
```

CONTROL OF ENZYMATIC PERACID GENERATION

This application is a DIV of U.S. patent application Ser. No. 12/539,025, filed Aug. 11, 2009, now U.S. Pat. No. 8,129,153, which claims the benefit of U.S. Provisional Patent Application No. 61/088,673, filed 10 Aug. 13, 2008 and U.S. Provisional Patent Application No. 61/102,520, filed Oct. 3, 2008, which are incorporated by reference herein in their entireties.

FIELD OF THE INVENTION

This invention relates to the field of peracid biosynthesis and in situ enzyme catalysis. Specifically, a process is provided to control the production of peracids generated by the perhydrolysis activity of enzymes identified structurally as belonging to the CE-7 family of carbohydrate esterases, including cephalosporin acetyl hydrolases (CAHs; E.C. 3.1.1.41) and acetyl xylan esterases (AXEs; E.C. 3.1.1.72). The enzymatic process produces percarboxylic acids from carboxylic acid ester substrates. Elucidation of the specific activity versus pH profile of the reaction allows control of the reaction by varying parameters including buffer concentration and pH. Disinfectant formulations comprising the peracids produced by the processes described herein are provided.

BACKGROUND OF THE INVENTION

Peracid compositions have been reported to be effective antimicrobial agents. Methods to clean, disinfect, and/or sanitize hard surfaces, meat products, living plant tissues, and medical devices against undesirable microbial growth have been described (U.S. Pat. No. 6,545,047; U.S. Pat. No. 6,183,807; U.S. Pat. No. 6,518,307; U.S. patent application publication 20030026846; and U.S. Pat. No. 5,683,724). Peracids have also been reported to be useful in preparing bleaching compositions for laundry detergent applications (U.S. Pat. No. 3,974,082; U.S. Pat. No. 5,296,161; and U.S. Pat. No. 5,364,554).

Peracids can be prepared by the chemical reaction of a carboxylic acid and hydrogen peroxide (see *Organic Peroxides*, Daniel Swern, ed., Vol. 1, pp 313-516; Wiley Interscience, New York, 1971). The reaction is usually catalyzed by a strong inorganic acid, such as concentrated sulfuric acid. The reaction of hydrogen peroxide with a carboxylic acid is an equilibrium reaction, and the production of peracid is favored by the use of an excess concentration of peroxide and/or carboxylic acid, or by the removal of water.

Enzyme catalysts can also catalyze the rapid production of peracid at the time of use and/or application, avoiding the need for storage of peracid solutions, which may cause peracid concentration to decrease over time. The high concentrations of carboxylic acids typically used to produce peracid via the direct chemical reaction with hydrogen peroxide are not required for enzymatic production of peracid, where the enzyme-catalyzed reaction can use a carboxylic acid ester as substrate at a much lower concentration than is typically used in the chemical reaction. The enzyme-catalyzed reaction can be performed across a broad range of pH, depending on enzyme activity and stability at a given pH, and on the substrate specificity for perhydrolysis at a given pH.

Esterases, lipases and some proteases have the ability to catalyze the hydrolysis of alkyl esters to produce the corresponding carboxylic acids (Formula 1):

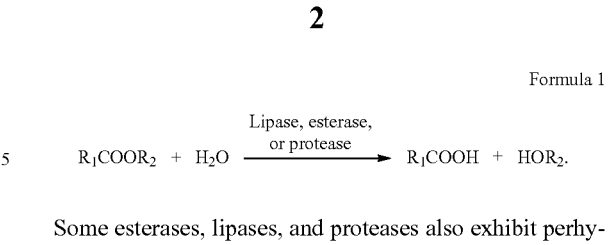

Formula 1

$$R_1COOR_2 + H_2O \xrightarrow{\text{Lipase, esterase, or protease}} R_1COOH + HOR_2.$$

Some esterases, lipases, and proteases also exhibit perhydrolysis activity, catalyzing the synthesis of peracids from alkyl esters (Formula 2):

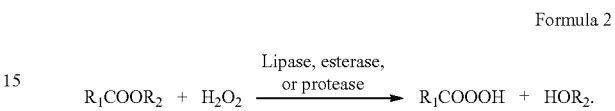

Formula 2

$$R_1COOR_2 + H_2O_2 \xrightarrow{\text{Lipase, esterase, or protease}} R_1COOOH + HOR_2.$$

The CE-7 class of carbohydrate esterases has been found to have highly specific activity for perhydrolysis of esters, particularly acetyl esters of alcohols, diols and glycerols. U.S. patent application Ser. Nos. 11/638,635; 11/743,354; 11/943,872; and 12/143,375 to DiCosimo et al. disclose enzymes structurally classified as members of the CE-7 family of carbohydrate esterases (e.g., cephalosporin C deacetylases [CAHs] and acetyl xylan esterases [AXEs]) that are characterized by significant perhydrolysis activity for converting carboxylic acid esters (in the presence of a suitable source of peroxygen, such as hydrogen peroxide) into peroxycarboxylic acids at concentrations sufficient for use as a disinfectant and/or a bleaching agent. Under certain reaction conditions, CE-7 esterases can catalyze the production of concentrations of peracid at least as high as 4000-5000 ppm in 1 min and up to at least 9000 ppm in 5 min to 30 min (U.S. patent application Ser. No. 12/143,375 to DiCosimo et al.). Peroxycarboxylic acids can be corrosive to certain metal surfaces, however, so it may be desirable to limit the total amount of peracid produced during the reaction to prevent or minimize the corrosive effect of the resulting solution. For example, applications that require production of no more than 200 ppm to 1000 ppm of peracid in 1 minute often employ reaction conditions that yield a final concentration of peracid well above these limits. In an application for in situ generation of peracid for disinfection of hard surfaces, it is desirable to have the ability to rapidly generate the desired concentration of peracid without significantly exceeding the upper efficacious disinfectant concentration, thereby limiting or preventing the corrosion of certain components of the surface. In an application for in situ generation of peracid for bleaching of laundry or textiles, similar limitations to the concentration of peracid generated above that required for bleaching are also desirable.

In addition to catalyzing the production of peracids, CE-7 esterases can also catalyze the hydrolysis of peracid to produce carboxylic acid and hydrogen peroxide. Therefore, under reaction conditions where the enzyme retains its activity for an extended period of time, it may destroy the peracid produced in the first enzyme-catalyzed reaction of ester and peroxide, producing carboxylic acid (e.g., acetic acid) as a byproduct that can impart an undesirable odor to the disinfectant solution. This peracid hydrolysis activity of the enzyme could also jeopardize the long term stability of peracid-containing formulations produced by CE-7 esterases over the course of several hours, or even several days or weeks, depending on the stability of the peracid in the disinfectant formulation.

Peracid solutions have a wide variety of applications. Though progress has been made in devising efficient and effective ways to produce peracid solutions, improved methods are needed. An in situ process for producing peracids that limits the enzyme-catalyzed production of peracids in a peracid concentration-dependent manner would allow targeted concentrations of peracids to be produced in a task-appropriate way.

SUMMARY OF THE INVENTION

Disclosed herein are enzyme-catalyzed processes of producing a target concentration of peracid. The enzyme-catalyzed production of peracids is limited in a peracid concentration-dependent manner. Also disclosed herein are processes of disinfecting surfaces or inanimate objects, and of bleaching of textiles or laundry, through the use of peracid-containing solutions that deliver a targeted concentration of peracid. The described processes are enabled by the first discovery that enzymes belonging to the structural family of CE-7 esterases (e.g., cephalosporin C deacetylases [CAHs] and acetyl xylan esterases [AXEs]) exhibit significant perhydrolysis activity for converting carboxylic acid esters into peracids, and by the second discovery that the activity of said enzymes for both perhydrolysis of esters to produce peracids and for hydrolysis of peracids to produce carboxylic acids and hydrogen peroxide decreases significantly or is inactivated as the pH of the reaction decreases over the course of the reaction that produces peracid and/or carboxylic acid. The activity of the CE-7 esterases for production of peracid, and optionally for hydrolysis of peracid, may be controlled by a number of methods, including but not limited to selecting the initial pH of the reaction, or by selecting the buffer and buffer concentration in the perhydrolysis reaction, or by a combination of selection of initial pH and buffer and buffer concentration, such that a targeted concentration of peracid, or targeted range of peracid concentration, is produced.

In one embodiment, the processes provide a means for producing enzyme-catalyzed peracid solutions having peracid concentrations sufficient to disinfect surfaces or inanimate objects and also reduce or prevent the corrosive effects associated with higher concentrations of peracid in solution. In a second embodiment, the processes provide a means for producing enzyme-catalyzed peracid solutions having peracid concentrations sufficient to disinfect or remove stains from textiles or laundry and also reduce or prevent the damaging effects associated with higher concentrations of peracid in solution towards dyed textiles or clothing, or damaging effects associated with fabric integrity. In some embodiments the processes provide a means for producing enzyme-catalyzed peracid solutions suitable to disinfect surfaces or inanimate objects where the duration of the enzymatic activity is insufficient to mediate a substantial secondary enzyme-catalyzed hydrolysis of the peracid produced in the initial enzyme-catalyzed reaction, where the secondary enzyme-catalyzed hydrolysis of the peracid yields a carboxylic acid (e.g., acetic acid).

One way to control the amount of peracid produced by the enzyme-catalyzed reaction is to use reaction conditions that selectively reduce, or inactivate, the catalytic function of the enzyme. The catalytic activity of perhydrolase enzymes can be controlled in a number of ways, such as altering the pH of the reaction mixture. Accordingly, the initial pH of the reaction mixture may be adjusted such that the pH of the reaction decreases as peracid is produced, ultimately resulting in the reaction mixture having a pH at which the enzyme activity is significantly reduced or inactivated. Alternatively, when only low concentrations of peracid are desirable, the initial pH of the reaction can be low enough to substantially reduce enzyme activity, resulting in only a very short period of enzyme-catalyzed peracid production. Another way to control the amount of peracid produced by the enzyme-catalyzed reaction is to employ a buffer concentration in the reaction mixture such that its buffering capacity is limited, causing the buffer to be quickly exhausted as peracid and other reaction products (e.g., carboxylic acid) are produced, and thereby reducing the pH of the reaction mixture and reducing, or inactivating, enzyme activity. One way to control the amount of peracid produced by an enzyme-catalyzed reaction is to select a reaction mixture initial pH and a buffer with a pKa that will cause the pH of the reaction mixture to decrease such that the enzymatic activity of the reaction is reduced or inactivated as the desired amount of peracid is produced. Another approach is to use a pH-sensitive enzyme with a high catalytic rate to produce a reaction with a high initial output of peracid that causes the pH of the reaction mixture to decrease to a point at which catalytic activity is significantly decreased or inactivated. Each of these approaches, however, requires selecting an enzyme for use in the reaction that has pH-sensitive catalytic activity, such that the ability of the enzyme to catalyze the production of peracid is eliminated, or substantially reduced, when the reaction mixture reaches a desired pH. In addition, the specific activity versus reaction pH profile of the enzyme must be understood in order to design perhydrolysis reactions that produce targeted amount of peracid. Described herein are pH-sensitive perhydrolase enzymes and methods of producing targeted concentrations of peracid in a fixed period of time.

Described are aqueous peracid solutions that maintain a relatively stable concentration of peracid, i.e., within about 20% of a target peracid concentration, following pH-mediated reduction, or inactivation, of enzyme catalyst activity. In some preferred embodiments, aqueous peracid solutions that maintain a peracid concentration within about 15% of a target peracid concentration, and more preferably within about 10% of a target peracid concentration, following pH-mediated reduction, or inactivation, of enzyme catalyst activity are provided. The stability of the peracid concentration can persist for hours after the reduction, or inactivation, of the enzyme-catalyzed production of peracid. In one embodiment, the peracid concentration is stable for about 3 hours, about 6 hours, about 9 hours, about 12 hours, about 15 hours, about 18 hours, about 21 hours, about 24 hours, about 30 hours, about 36 hours, about 42 hours, or about 48 hours after the enzyme-catalyzed production of peracid has ceased.

Specific examples of perhydrolases are exemplified from *Bacillus subtilis* (ATCC® 31954™), *B. subtilis* BE1010 (Payne and Jackson, *J. Bacteriol.* 173:2278-2282 (1991)), *B. subtilis* ATCC® 6633™ (U.S. Pat. No. 6,465,233), *B. subtilis* ATCC® 29233™; *B. licheniformis* ATCC® 14580™ (Rey et al., *Genome Biol.*, 5(10):article 77 (2004)), *Clostridium thermocellum* ATCC®27405™ (Copeland et al., GENBANK® ZP_00504991, *B. pumilus* PS213 (Degrassi et al., *Microbiology*, 146:1585-1591 (2000)), *Thermotoga neapolitana* (GENBANK® AAB70869.1), *Bacillus clausii* KSM-K16 (GENBANK® YP_175265), *Bacillus* sp. NRRL B-14911 (GENBANK® ZP_01168674), *Bacillus halodurans* C-125 (GENBANK® NP 244192), *Thermoanaerobacterium* sp. JW/SL YS485 (GENBANK® AAB68821), *Bacillus subtilis* subsp. *subtilis* str. 168 (GENBANK® NP_388200), *Thermotoga maritima* MSB8 (GENBANK® NP_227893.1), *Thermoanaerobacterium saccharolyticum* (GENBANK® S41858), *Thermotoga lettingae* (GENBANK® CP000812), *Thermotoga petrophila* (GENBANK® CP000702), and *Thermotoga* sp. RQ2 (GENBANK® CP000969).

Each of the present perhydrolase enzymes described herein share conserved structural features (i.e., a conserved signature motif) as well as superior perhydrolysis activity relative to other α/β-hydrolases, which makes this family of enzymes particularly suitable for generating peracids in situ at concentrations sufficient for use as a disinfectant and/or bleaching agent. Suitable perhydrolases useful in the present process can be identified by a conserved signature motif found within the CE-7 family of carbohydrate esterases.

Provided herein is a process for producing a target concentration of peroxycarboxylic acid comprising:
a. selecting a set of reaction components to produce a target concentration of peroxycarboxylic acid, said reaction components comprising:
  1) at least one:
    i) ester having the structure $[X]_m R_5$ wherein X is an ester group of the formula $R_6C(O)O$
    $R_6$ is a C1 to C7 linear, branched or cyclic hydrocarbyl moiety, optionally substituted with hydroxyl groups or C1 to C4 alkoxy groups, wherein $R_6$ optionally comprises one or more ether linkages when $R_6$ is C2 to C7;
    $R_5$ is a C1 to C6 linear, branched, or cyclic hydrocarbyl moiety optionally substituted with hydroxyl groups; wherein each carbon atom in $R_5$ individually comprises no more than one hydroxyl group or no more than one ester group; wherein $R_5$ optionally comprises one or more ether linkages;
    m is an integer from 1 to the number of carbon atoms in $R_5$;
    said ester having a solubility in water of at least 5 parts per million at 25° C.; or
    ii) glyceride having the structure

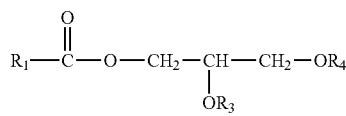

wherein $R_1$ is C1 to C7 straight chain or branched chain alkyl optionally substituted with an hydroxyl or a C1 to C4 alkoxy group and $R_3$ and $R_4$ are individually H or $R_1C(O)$; or
    iii) acetylated monosaccharide, acetylated disaccharide, or acetylated polysaccharide;
    or mixtures thereof;
  2) a source of peroxygen;
  3) an enzyme catalyst having perhydrolysis activity, wherein said enzyme catalyst comprises an enzyme having a CE-7 signature motif that aligns with a reference sequence SEQ ID NO: 2 using CLUSTALW, said signature motif comprising:
    i) an RGQ motif at amino acid positions 118-120 of SEQ ID NO:2;
    ii) a GXSQG motif at amino acid positions 179-183 of SEQ ID NO:2; and
    iii) an HE motif at amino acid positions 298-299 of SEQ ID NO:2; and
    wherein said enzyme comprises at least 30% amino acid identity to SEQ ID NO: 2; and
  4) optionally at least one buffer; and
b. combining the selected set of reaction components under aqueous reaction conditions to form a reaction mixture; whereby reaction products are formed comprising peroxycarboxylic acid; wherein the reaction products comprising peroxycarboxylic acid reduce the reaction mixture pH to less than about 6.0 within about 1 minute to about 10 minutes of combining the reaction components and produce the target concentration of peroxycarboxylic acid; wherein the reduction in the reaction mixture pH is used to control the target concentration of peroxycarboxylic acid produced.

Also provided herein is a process for disinfecting a hard surface or inanimate object by producing a target concentration of peroxycarboxylic acid comprising:
a. selecting a set of reaction components to produce a target concentration of peroxycarboxylic acid, said reaction components comprising:
  1) at least one:
    i) ester having the structure $[X]_m R_5$ wherein X is an ester group of the formula $R_6C(O)O$
    $R_6$ is a C1 to C7 linear, branched or cyclic hydrocarbyl moiety, optionally substituted with hydroxyl groups or C1 to C4 alkoxy groups, wherein $R_6$ optionally comprises one or more ether linkages when $R_6$ is C2 to C7;
    $R_5$ is a C1 to C6 linear, branched, or cyclic hydrocarbyl moiety optionally substituted with hydroxyl groups; wherein each carbon atom in $R_5$ individually comprises no more than one hydroxyl group or no more than one ester group; wherein $R_5$ optionally comprises one or more ether linkages;
    m is an integer from 1 to the number of carbon atoms in $R_5$;
    said ester having a solubility in water of at least 5 parts per million at 25° C.; or
    ii) glyceride having the structure

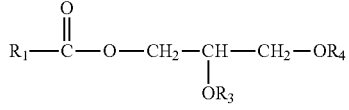

wherein $R_1$ is C1 to C7 straight chain or branched chain alkyl optionally substituted with an hydroxyl or a C1 to C4 alkoxy group and $R_3$ and $R_4$ are individually H or $R_1C(O)$; or
    iii) acetylated monosaccharide, acetylated disaccharide, or acetylated polysaccharide;
    or mixtures thereof;
  2) a source of peroxygen;
  3) an enzyme catalyst having perhydrolysis activity, wherein said enzyme catalyst comprises an enzyme having a CE-7 signature motif that aligns with a reference sequence SEQ ID NO: 2 using CLUSTALW, said signature motif comprising:
    i) an RGQ motif at amino acid positions 118-120 of SEQ ID NO:2;
    ii) a GXSQG motif at amino acid positions 179-183 of SEQ ID NO:2; and iii) an HE motif at amino acid positions 298-299 of SEQ ID NO:2; and
wherein said enzyme comprises at least 30% amino acid identity to SEQ ID NO: 2; and
4) optionally at least one buffer;
b. combining the selected set of reaction components under aqueous reaction conditions to form a reaction mixture; whereby reaction products are formed comprising peroxycarboxylic acid; wherein the reaction products comprising peroxycarboxylic acid reduce the reaction mixture pH to less than about 6.0 within about 1 minute to about 10 minutes of combining the reaction components and produce the target concentration of peroxycarboxylic acid; wherein the reduction in the reaction mixture pH is used to control the target concentration of peroxycarboxylic acid produced; and
c. applying the peroxycarboxylic acid produced in step (b) to a hard surface or inanimate object.

In some embodiments, the peroxycarboxylic acid produced is diluted.

In another embodiment, the catalyst is a substantially similar enzyme having an amino acid sequence at least 90%, 91%, 92%, 93%, 94%, 95%, 96%, 97%, 98%, or 99% identical to one or more amino acid sequences selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 30, SEQ ID NO: 54, SEQ ID NO: 56, SEQ ID NO: 58, SEQ ID NO: 60, and SEQ ID NO: 62.

In another embodiment, the perhydrolase catalyst comprises an enzyme having an amino acid sequence encoded by a nucleic acid molecule that hybridizes to a nucleic acid sequence selected from the group consisting of SEQ ID NO: 1; SEQ ID NO: 3; SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 29, SEQ ID NO: 55, SEQ ID NO: 57, SEQ ID NO: 59, and SEQ ID NO: 61 under stringent hybridization conditions. In a preferred embodiment, the present invention includes an enzyme having perhydrolase activity encoded by isolated nucleic acid molecule that hybridizes under stringent conditions to a nucleic acid molecule having a nucleic acid sequence selected from the group consisting of SEQ ID NO: 1, SEQ ID NO: 9, SEQ ID NO: 13, and SEQ ID NO: 15.

In another embodiment, the perhydrolase catalyst comprises a variant *Thermotoga* enzyme having at least 95% amino acid sequence identity (or, in various embodiments, 96%, 97%, 98%, or 99% sequence identity), based on the CLUSTAL method of alignment (such as CLUSTALW) with pairwise alignment default parameters of KTUPLE=1, GAP PENALTY=3, WINDOW=5 and DIAGONALS SAVED=5, when compared to SEQ ID NOs: 69, 70, 71, 72, or 73, provided that a substitution to amino acid 277 of SEQ ID NOs: 69, 70, 71, 72, or 73 is selected from the group consisting of serine, threonine, valine, and alanine.

In another embodiment, the perhydrolase catalyst comprises a variant *Thermotoga* enzyme comprising an amino acid sequence selected from the group consisting of SEQ ID NOs: 69, 70, 71, 72, and 73 provided the amino acid residue 277 is selected from the group consisting of serine, threonine, valine, and alanine.

In a specific embodiment, the perhydrolase catalyst comprises a variant *Thermotoga neapolitana* enzyme comprising amino acid sequence SEQ ID NO: 69 wherein amino acid residue 277 is substituted with an amino acid selected from the group consisting of serine, threonine, valine, and alanine.

In a further specific embodiment, the perhydrolase catalyst is a variant *Thermotoga maritima* enzyme comprising amino acid sequence SEQ ID NO: 70 wherein amino acid residue 277 is substituted with an amino acid selected from the group consisting of serine, threonine, valine, and alanine.

In some aspects, the aqueous reaction mixture includes a buffer and has a specific initial pH. The buffer may be any buffer suitable for carrying out an enzymatic perhydrolysis reaction at the desired pH. In some aspects, the buffer is selected from the group consisting of the sodium salt, the potassium salt or mixed sodium and potassium salts of bicarbonate buffer, citrate buffer, methylphosphonate buffer, pyrophosphate buffer and phosphate buffer. In some aspects, the buffer is bicarbonate buffer or citrate buffer. In some aspects, the reaction mixture containing a buffer has an initial pH of about 5.5 to about 8.5. In some aspects, the reaction mixture containing a buffer has an initial pH of about 8.5. In some aspects, the reaction mixture containing a buffer has an initial pH of about 8.1. In some aspects, the reaction mixture containing a buffer has an initial pH of about 7.2. In some aspects, the reaction mixture containing a buffer has an initial pH of about 6.5. In some aspects, the reaction mixture containing a buffer has an initial pH of about 6.0. In some aspects, the reaction mixture containing a buffer has an initial pH of about 5.5.

In some aspects, the buffer included in the aqueous reaction mixture can establish the initial pH of the mixture. In some aspects, the buffer produces an aqueous reaction mixture with an initial pH of about 5.5 to about 8.5. In some aspects, the buffer produces an aqueous reaction mixture with an initial pH of about 8.1. In some aspects, the buffer produces an aqueous reaction mixture with an initial pH of about 7.2. In some aspects, the buffer produces an aqueous reaction mixture with an initial pH of about 6.5. In some aspects, the buffer produces an aqueous reaction mixture with an initial pH of about 6.0. In some aspects, the buffer produces an aqueous reaction mixture with an initial pH of about 5.5.

In some aspects, the aqueous reaction mixture may include at least one buffer having a specific concentration. The buffer may be any buffer suitable for carrying out an enzymatic perhydrolysis reaction. In some aspects, the reaction mixture contains buffer at a concentration of about 0.01 mM to about 200 mM. In some aspects, the reaction mixture contains buffer at a concentration of about 50 mM. In some aspects, the reaction mixture contains buffer having a concentration of about 25 mM to about 0.1 mM. In some aspects, the reaction mixture contains bicarbonate buffer having a concentration of about 25 mM to about 0.1 mM. In some aspects, the reaction mixture contains buffer having a concentration of less than about 5 mM. In some aspects, the reaction mixture contains bicarbonate buffer having a concentration of less than about 5 mM.

In a preferred embodiment, the substrate is selected from the group consisting of monoacetin; diacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-glucal; monoesters or diesters of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,6-pentanediol, 1,2-hexanediol, 2,5-hexanediol, 1,6-hexanediol; and mixtures thereof.

BRIEF DESCRIPTION OF THE BIOLOGICAL SEQUENCES

The following sequences comply with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. §1.822.

SEQ ID NO: 1 is the nucleic acid sequence of the cephalosporin C deacetylase (cah) coding region from *Bacillus subtilis* ATCC® 31954T".

SEQ ID NO: 2 is the deduced amino acid sequence of the cephalosporin C deacetylase from *Bacillus subtilis* ATCC® 31954™.

SEQ ID NO: 3 is the nucleic acid sequence of the cephalosporin C deacetylase coding region from *B. subtilis* subsp. *subtilis* str. 168.

SEQ ID NO: 4 is the deduced amino acid sequence of the cephalosporin C deacetylase from *B. subtilis* subsp. *subtilis* str. 168, and is identical to the deduced amino acid sequence of the cephalosporin C deacetylase from *B. subtilis* BE1010.

SEQ ID NO: 5 is the nucleic acid sequence of the cephalosporin acetylesterase coding region from *B. subtilis* ATCC® 6633™.

SEQ ID NO: 6 is the deduced amino acid sequence of the cephalosporin acetylesterase from *B. subtilis* ATCC® 6633™.

SEQ ID NO: 7 is the nucleic acid sequence of the cephalosporin C deacetylase coding region from *B. licheniformis* ATCC® 14580™.

SEQ ID NO: 8 is the deduced amino acid sequence of the cephalosporin C deacetylase from *B. licheniformis* ATCC® 14580™.

SEQ ID NO: 9 is the nucleic acid sequence of the acetyl xylan esterase coding region from *B. pumilus* PS213.

SEQ ID NO: 10 is the deduced amino acid sequence of the acetyl xylan esterase from *B. pumilus* PS213.

SEQ ID NO: 11 is the nucleic acid sequence of the acetyl xylan esterase coding region from *Clostridium thermocellum* ATCC® 27405™.

SEQ ID NO: 12 is the deduced amino acid sequence of the acetyl xylan esterase from *Clostridium thermocellum* ATCC® 27405™.

SEQ ID NO: 13 is the nucleic acid sequence of the acetyl xylan esterase coding region from *Thermotoga neapolitana*.

SEQ ID NO: 14 is the deduced amino acid sequence of the acetyl xylan esterase from *Thermotoga neapolitana*.

SEQ ID NO: 15 is the nucleic acid sequence of the acetyl xylan esterase coding region from *Thermotoga maritima* MSB8.

SEQ ID NO: 16 is the deduced amino acid sequence of the acetyl xylan esterase from *Thermotoga maritima* MSB8.

SEQ ID NO: 17 is the nucleic acid sequence of the acetyl xylan esterase coding region from *Thermoanaerobacterium* sp. JW/SL YS485.

SEQ ID NO: 18 is the deduced amino acid sequence of the acetyl xylan esterase from *Thermoanaerobacterium* sp. JW/SL YS485.

SEQ ID NO: 19 is the nucleic acid sequence of the cephalosporin C deacetylase coding region from *Bacillus* sp. NRRL B-14911.

SEQ ID NO: 20 is the deduced amino acid sequence of the cephalosporin C deacetylase from *Bacillus* sp. NRRL B-14911.

SEQ ID NO: 21 is the nucleic acid sequence of the cephalosporin C deacetylase coding region from *Bacillus halodurans* C-125.

SEQ ID NO: 22 is the deduced amino acid sequence of the cephalosporin C deacetylase from *Bacillus halodurans* C-125.

SEQ ID NO: 23 is the nucleic acid sequence of the cephalosporin C deacetylase coding region from *Bacillus clausii* KSM-K16.

SEQ ID NO: 24 is the deduced amino acid sequence of the cephalosporin C deacetylase from *Bacillus* clausii KSM-K16.

SEQ ID NOs: 25 and 26 are primers used to PCR amplify perhydrolase genes from *Bacillus subtilis* species for construction of pSW194 and pSW189.

SEQ ID NO: 27 is the nucleic acid sequence of the PCR product cloned into pSW194.

SEQ ID NO: 28 is the nucleic acid sequence of the PCR product cloned into pSW189.

SEQ ID NO: 29 is the nucleic acid sequence of the *Bacillus subtilis* ATCC® 29233™ cephalosporin C deacetylase (cah) gene.

SEQ ID NO: 30 is the deduced amino acid sequence of the *Bacillus subtilis* ATCC® 29233™ cephalosporin C deacetylase (CAH).

SEQ ID NOs: 31 and 32 are primers used to PCR amplify the *Bacillus licheniformis* ATCC® 14580™ cephalosporin C deacetylase gene for construction of pSW191.

SEQ ID NOs: 33 and 34 are primers used to PCR amplify the *Bacillus pumilus* PS213 acetyl xylan esterase coding sequence (GENBANK® AJ249957) for construction of pSW195.

SEQ ID NO: 35 is the nucleic acid sequence of the kanamycin resistance gene.

SEQ ID NO 36 is the nucleic acid sequence of plasmid pKD13.

SEQ ID NOs: 37 and 38 are primers used to generate a PCR product encoding the kanamycin gene flanked by regions having homology to the katG catalase gene in *E. coli* MG1655. The product was used to disrupt the endogenous katG gene.

SEQ ID NO: 39 is the nucleic acid sequence of the PCR product encoding the kanamycin resistance gene flanked by regions having homology to the katG catalase gene in *E. coli* MG1655. The product was used to disrupt the endogenous katG gene.

SEQ ID NO: 40 is the nucleic acid sequence of the katG catalase gene in *E. coli* MG1655.

SEQ ID NO: 41 is the deduced amino acid sequence of the KatG catalase in *E. coli* MG1655.

SEQ ID NO: 42 is the nucleic acid sequence of plasmid pKD46.

SEQ ID NOs: 43 and 44 are primers used to confirm the disruption of the katG gene.

SEQ ID NO: 45 is the nucleic acid sequence of plasmid pCP20.

SEQ ID NOs: 46 and 47 are primers used to generate a PCR product encoding the kanamycin gene flanked by regions having homology to the katE catalase gene in *E. coli* MG1655. The product was used to disrupt the endogenous katE gene.

SEQ ID NO: 48 is the nucleic acid sequence of the PCR product encoding the kanamycin resistance gene flanked by regions having homology to the katE catalase gene in *E. coli* MG1655. The product was used to disrupt the endogenous katE gene.

SEQ ID NO: 49 is the nucleic acid sequence of the katE catalase gene in *E. coli* MG1655.

SEQ ID NO: 50 is the deduced amino acid sequence of the KatE catalase in *E. coli* MG1655.

SEQ ID NOs: 51 and 52 are primers used to confirm disruption of the katE gene in the single knockout strain *E. coli* MG1655 ΔkatE, and in the double-knockout strain *E. coli* MG1655 ΔkatG ΔkatE, herein referred to as *E. coli* KLP18.

SEQ ID NO: 53 is the amino acid sequence of the region encompassing amino acids residues 118 through 299 of SEQ ID NO: 2.

SEQ ID NO: 54 is the deduced amino acid sequence of the acetyl xylan esterase from *Thermoanaerobacterium saccharolyticum* (GENBANK® Accession No. S41858).

SEQ ID NO: 55 is the nucleic acid sequence of the acetyl xylan esterase coding region from *Thermotoga lettingae*.

SEQ ID NO: 56 is the deduced amino acid sequence of the acetyl xylan esterase from *Thermotoga lettingae*.

SEQ ID NO: 57 is the nucleic acid sequence of the acetyl xylan esterase coding region from *Thermotoga petrophila*.

SEQ ID NO: 58 is the deduced amino acid sequence of an acetyl xylan esterase from *Thermotoga petrophila*.

SEQ ID NO: 59 is the nucleic acid sequence of the acetyl xylan esterase coding region from *Thermotoga* sp. RQ2 identified herein as "RQ2(a)".

SEQ ID NO: 60 is the deduced amino acid sequence of an acetyl xylan esterase (GENBANK® Accession No. ACB09222) from *Thermotoga* sp. RQ2 identified herein as "RQ2(a)".

SEQ ID NO: 61 is the nucleic acid sequence of the acetyl xylan esterase coding region from *Thermotoga* sp. RQ2 identified herein as "RQ2(b)".

SEQ ID NO: 62 is the deduced amino acid sequence of an acetyl xylan esterase (GENBANK® Accession No. ACB08860) from *Thermotoga* sp. RQ2 identified herein as "RQ2(b)".

SEQ ID NOs: 63 and 64 are primers used to PCR amplify the *Thermotoga maritima* MSB8 acetyl xylan esterase gene (GENBANK accession #NP_227893.1).

SEQ ID NO: 65 is the PCR amplified nucleic acid sequence of the *Thermotoga maritima* MSB8 acetyl xylan esterase used to generate pSW207.

SEQ ID NOs: 66 and 67 are primers used to PCR amplify the *Thermotoga neapolitana* acetyl xylan esterase gene (GENBANK® 58632) for construction of pSW196.

SEQ ID NO: 68 is the nucleic acid sequence of the codon-optimized version of the *Thermotoga neapolitana* acetyl xylan esterase gene in plasmid pSW196.

SEQ ID NO: 69 represents the deduced amino acid sequence of the acetyl xylan esterase variants derived from the wild-type sequence of an acetyl xylan esterase from *Thermotoga neapolitana*, where the Xaa residue at position 277 is Ala, Val, Ser, or Thr.

SEQ ID NO: 70 represents the deduced amino acid sequence of the acetyl xylan esterase variants derived from the wild-type sequence of an acetyl xylan esterase from *Thermotoga maritima* MSB8, where the Xaa residue at position 277 is Ala, Val, Ser, or Thr.

SEQ ID NO: 71 represents the deduced amino acid sequence of the acetyl xylan esterase variants derived from the wild-type sequence of an acetyl xylan esterase from *Thermotoga lettingae*, where the Xaa residue at position 277 is Ala, Val, Ser, or Thr.

SEQ ID NO: 72 represents the deduced amino acid sequence of the acetyl xylan esterase variants derived from the wild-type sequence of an acetyl xylan esterase from *Thermotoga petrophila*, where the Xaa residue at position 277 is Ala, Val, Ser, or Thr.

SEQ ID NO: 73 represents the deduced amino acid sequence of the acetyl xylan esterase variants derived from the wild-type sequence of an acetyl xylan esterase from *Thermotoga* sp. RQ2 described herein as "RQ2(a)", where the Xaa residue at position 277 is Ala, Val, Ser, or Thr.

DETAILED DESCRIPTION

The stated problems have been solved by the discovery that enzymes belonging to the CE-7 carbohydrate esterase family exhibit significant perhydrolysis activity for converting carboxylic acid ester substrates to peracids that can be regulated by controlling the pH of the reaction mixture. Elucidation of the specific activity versus pH profile of CE-7 carbohydrate esterases allows for the control of enzyme-driven production of peracids by varying reaction parameters including buffer concentration and pH. Having this understanding, this family of structurally related enzymes can be used to generate stable, targeted concentrations of peracids for disinfection and/or bleaching applications.

In this disclosure, a number of terms and abbreviations are used. The following definitions apply unless specifically stated otherwise.

As used herein, the term "comprising" means the presence of the stated features, integers, steps, or components as referred to in the claims, but does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, the term "peracid" is synonymous with peroxyacid, peroxycarboxylic acid, peroxy acid, percarboxylic acid and peroxoic acid.

As used herein, the term "peracetic acid" is abbreviated as "PAA" and is synonymous with peroxyacetic acid, ethaneperoxoic acid and all other synonyms of CAS Registry Number 79-21-0.

As used herein, the term "monoacetin" is synonymous with glycerol monoacetate, glycerin monoacetate, and glyceryl monoacetate.

As used herein, the term "diacetin" is synonymous with glycerol diacetate; glycerin diacetate, glyceryl diacetate, and all other synonyms of CAS Registry Number 25395-31-7.

As used herein, the term "triacetin" is synonymous with glycerin triacetate; glycerol triacetate; glyceryl triacetate, 1,2,3-triacetoxypropane, 1,2,3-propanetriol triacetate and all other synonyms of CAS Registry Number 102-76-1.

As used herein, the term "monobutyrin" is synonymous with glycerol monobutyrate, glycerin monobutyrate, and glyceryl monobutyrate.

As used herein, the term "dibutyrin" is synonymous with glycerol dibutyrate and glyceryl dibutyrate.

As used herein, the term "tributyrin" is synonymous with glycerol tributyrate, 1,2,3-tributyrylglycerol, and all other synonyms of CAS Registry Number 60-01-5.

As used herein, the term "monopropionin" is synonymous with glycerol monopropionate, glycerin monopropionate, and glyceryl monopropionate.

As used herein, the term "dipropionin" is synonymous with glycerol dipropionate and glyceryl dipropionate.

As used herein, the term "tripropionin" is synonymous with glyceryl tripropionate, glycerol tripropionate, 1,2,3-tripropionylglycerol, and all other synonyms of CAS Registry Number 139-45-7.

As used herein, the term "ethyl acetate" is synonymous with acetic ether, acetoxyethane, ethyl ethanoate, acetic acid ethyl ester, ethanoic acid ethyl ester, ethyl acetic ester and all other synonyms of CAS Registry Number 141-78-6.

As used herein, the term "ethyl lactate" is synonymous with lactic acid ethyl ester and all other synonyms of CAS Registry Number 97-64-3.

As used herein, the terms "acetylated sugar" and "acetylated saccharide" refer to mono-, di- and polysaccharides comprising at least one acetyl group. Examples include, but are not limited to, glucose pentaacetate, xylose tetraacetate, acetylated xylan, acetylated xylan fragments, β-D-ribofuranose-1,2,3,5-tetraacetate, tri-O-acetyl-D-galactal, and tri-O-acetyl-glucal.

As used herein, the terms "hydrocarbyl", "hydrocarbyl group", and "hydrocarbyl moiety" mean a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, pentyl, cyclopentyl, methylcyclopentyl, hexyl, cyclohexyl, benzyl, and phenyl. In a preferred embodiment, the hydrocarbyl moiety is a straight chain, branched or cyclic arrangement of carbon atoms connected by single carbon to carbon bonds and/or by ether linkages, and substituted accordingly with hydrogen atoms.

As used herein, the terms "monoesters" and "diesters" of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,6-pentanediol, 1,2-hexanediol, 2,5-hexanediol, 1,6-hexanediol, refer to said compounds comprising at least one ester group of the formula RC(O)O, wherein R is a C1 to C7 linear hydrocarbyl moiety.

As used herein, the terms "suitable enzymatic reaction mixture", "components suitable for in situ generation of a peracid", "suitable reaction components", "selected set of reaction components", and "suitable aqueous reaction mixture" refer to the materials and water in which the reactants and enzyme catalyst come into contact. The reaction components are selected such that the pH of the reaction mixture is used to control the production of the desired target concentration of peroxycarboxylic acid by decreasing and/or inactivating the enzyme catalyst's perhydrolysis activity.

As used herein, the term "reaction products" will refer to the mixture of compounds formed within the reaction mixture after combining the selected reaction components. The reaction products are comprised of the enzymatically-generated peroxycarboxylic acid (e.g., peracetic acid) as well as one or more hydrolysis products (enzymatic and/or chemical hydrolysis products), such as the corresponding carboxylic acid (e.g., acetic acid). In one embodiment, combining the selected set of reaction components generates a reaction mixture capable of forming reaction products that reduce the pH of the reaction mixture whereby the perhydrolysis activity of the enzyme catalyst is substantially decreased and/or inactivated within 10 minutes of combining the reaction components, preferably within about 1 minute to about 10 minutes. In one embodiment, the perhydrolysis activity of the enzyme catalyst is reduced at least 80% in 10 minutes or less after combining the reaction components. The reaction products provide a reaction mixture pH suitable to control the amount of enzymatically-generated peroxycarboxylic acid. The initial reaction pH will be dependent on a number of variables, including reaction component concentrations, reaction temperature, the presence or absence of a buffer, the buffer pKa, and the buffer concentration. In one embodiment, the pH of the reaction mixture drops below about 6.0 within 10 minutes of combining the selected set of reaction components. In another embodiment, the reaction products reduce the reaction mixture pH to less than about 6.0 within about 1 minute to about 10 minutes of combining the reaction components.

The components of the suitable aqueous reaction mixture are provided herein and those skilled in the art appreciate the range of component variations suitable for this process. In one embodiment, the suitable enzymatic reaction mixture produces peracid in situ upon combining the reaction components. As such, the reaction components may be provided as a multicomponent system wherein one or more of the reaction components remains separated until use. The design of systems and means for separating and combining multiple active components are known in the art and generally will depend upon the physical form of the individual reaction components. For example, multiple active fluids (liquid-liquid) systems typically use multichamber dispenser bottles or two-phase systems (U.S. Patent Application Pub. No. 2005/0139608; U.S. Pat. No. 5,398,846; U.S. Pat. No. 5,624,634; U.S. Pat. No. 6,391,840; E.P. Patent 0807156B1; U.S. Patent Appln. Pub. No. 2005/0008526; and PCT Publication No. WO 00/11713A1) such as found in some bleaching applications wherein the desired bleaching agent is produced upon mixing the reactive fluids. Other forms of multicomponent systems used to generate peracid may include, but are not limited to those designed for one or more solid components or combinations of solid-liquid components, such as powders (e.g., many commercially available bleaching composition, U.S. Pat. No. 5,116,575), multi-layered tablets (U.S. Pat. No. 6,210,639), water dissolvable packets having multiple compartments (U.S. Pat. No. 6,995,125) and solid agglomerates that react upon the addition of water (U.S. Pat. No. 6,319,888).

One embodiment provides, a process for producing a targeted concentration of peroxycarboxylic acid by controlling the catalytic activity of an enzyme, comprising: combining selected reaction components, under suitable aqueous reaction conditions, to produce a target concentration of peroxycarboxylic acid, said reaction components comprising:
  a first mixture comprising:
    i) an enzyme catalyst having perhydrolase activity, said enzyme catalyst comprising an enzyme having a CE-7 signature motif; and
    ii) a carboxylic acid ester substrate, said first mixture optionally comprising a component selected from the group consisting of an inorganic or organic buffer, a corrosion inhibitor, a wetting agent, and combinations thereof; and a second mixture comprising a source of peroxygen and water, said second mixture optionally comprising a chelating agent.

In a further related embodiment, the carboxylic acid ester substrate in the first mixture of the formulation is selected from the group consisting of:

i) esters having the structure

wherein X=an ester group of the formula $R_6$—C(O)O $R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;

$R_5$=a C1 to C6 linear, branched, or cyclic hydrocarbyl moiety optionally substituted with hydroxyl groups; wherein each carbon atom in $R_5$ individually comprises no more than one hydroxyl group or no more than one ester group; wherein $R_5$ optionally comprises one or more ether linkages;

m=1 to the number of carbon atoms in $R_5$; and wherein said esters have a solubility in water of at least 5 ppm at 25° C.;

ii) glycerides having the structure

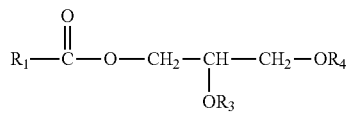

wherein $R_1$=C1 to C7 straight chain or branched chain alkyl optionally substituted with an hydroxyl or a C1 to C4 alkoxy group and $R_3$ and $R_4$ are individually H or $R_1$C(O); and iii) acetylated saccharides selected from the group consisting of acetylated monosaccharides, acetylated disaccharides, and acetylated polysaccharides;

In another embodiment, the carboxylic acid ester substrate in the first mixture of the formulation is defined by the following formula:

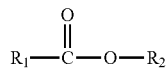

wherein $R_1$=C1 to C7 straight chain or branched chain alkyl optionally substituted with an hydroxyl or a C1 to C4 alkoxy group and $R_2$=C1 to $C_{10}$ straight chain or branched chain alkyl, alkenyl, alkynyl, aryl, alkylaryl, alkylheteroaryl, heteroaryl, $(CH_2CH_2$—O$)_n$H or $(CH_2CH(CH_3)$—O$)_n$H and n=1 to 10.

In a preferred embodiment, $R_6$ is C1 to C7 linear hydrocarbyl moiety, optionally substituted with hydroxyl groups or C1 to C4 alkoxy groups, optionally comprising one or more ether linkages. In a further preferred embodiment, $R_6$ is C2 to C7 linear hydrocarbyl moiety, optionally substituted with hydroxyl groups, and/or optionally comprising one or more ether linkages.

In another embodiment, the carboxylic acid ester substrate is selected from the group consisting of monoacetin; diacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-glucal; monoesters or diesters of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,6-pentanediol, 1,2-hexanediol, 2,5-hexanediol, 1,6-hexanediol; and mixtures thereof.

In another embodiment, the carboxylic acid ester is selected from the group consisting of monoacetin, diacetin, triacetin, and combinations thereof. In another embodiment, the carboxylic acid ester is an acetylated saccharide. In another embodiment, the substrate is a C1 to C6 polyol comprising one or more ester groups. In a preferred embodiment, one or more of the hydroxyl groups on the C1 to C6 polyol are substituted with one or more acetoxy groups (e.g. 1,3-propanediol diacetate, 1,4-butanediol diacetate, etc.). In another embodiment, the enzyme catalyst is a particulate solid. In another embodiment, the first reaction mixture described above is a solid tablet or powder.

As used herein, the term "perhydrolysis" is defined as the reaction of a selected substrate with peroxide to form a peracid. Typically, inorganic peroxide is reacted with the selected substrate in the presence of a catalyst to produce the peracid. Alternatively, hydrogen peroxide can be generated in situ by the reaction of a substrate and oxygen catalyzed by an enzyme having oxidase activity (e.g., glucose oxidase, alcohol oxidase, monoamine oxidase, lactate oxidase, amino acid oxidase). As used herein, the term "chemical perhydrolysis" includes perhydrolysis reactions in which a substrate (a peracid precursor) is combined with a source of hydrogen peroxide wherein peracid is formed in the absence of an enzyme catalyst.

As used herein, the term "perhydrolase activity" refers to the catalyst activity per unit mass (for example, milligram) of protein, dry cell weight, or immobilized catalyst weight.

As used herein, "one unit of enzyme activity" or "one unit of activity" or "U" is defined as the amount of perhydrolase activity required for the production of 1 μmol of peracid product per minute at a specified temperature.

As used herein, the terms "enzyme catalyst" and "perhydrolase catalyst" refer to a catalyst comprising an enzyme having perhydrolysis activity and may be in the form of a whole microbial cell, permeabilized microbial cell(s), one or more cell components of a microbial cell extract, partially purified enzyme, or purified enzyme. The enzyme catalyst may also be chemically modified (e.g., by pegylation or by reaction with cross-linking reagents). The perhydrolase catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. As described herein, all of the present enzymes having perhydrolysis activity are structurally members of the carbohydrate family esterase family 7 (CE-7 family) of enzymes (see Coutinho, P. M., Henrissat, B. "Carbohydrate-active enzymes: an integrated database approach" in *Recent Advances in Carbohydrate Bioengineering*, H. J. Gilbert, G. Davies, B. Henrissat and B. Svensson eds., (1999) The Royal Society of Chemistry, Cambridge, pp. 3-12).

Members of the CE-7 family include cephalosporin C deacetylases (CAHs; E.C. 3.1.1.41) and acetyl xylan esterases (AXEs; E.C. 11.1.72). Members of the CE-7 esterase family share a conserved signature motif (Vincent et al., *J. Mol. Biol.*, 330:593-606 (2003)). Perhydrolases comprising the CE-7 signature motif and/or a substantially similar structure are suitable for use in the present invention. Means to identify substantially similar biological molecules are well known in the art (e.g. sequence alignment protocols, nucleic acid hybridizations, presence of a conserved signature motif, etc.). In one aspect, the enzyme catalyst in the present process comprises a substantially similar enzyme having at least 30%, preferably at least 33%, more preferably at least 40%, more preferably at least 50%, even more preferably at least 60%, yet even more preferable at least 70%, yet even more preferably at least 80%, yet even more preferably at least 90%, 91%, 92%, 93%, 94%, 95%, 96%, 97%, 98%, or 99% amino acid identity to the sequences provided herein. The nucleic acid molecules encoding the present CE-7 carbohydrate esterases are also provided herein. In a further embodiment, the perhydrolase catalyst useful in the present process is encoded by a nucleic acid molecule that hybridizes stringent conditions to one of the present nucleic acid molecules.

As used herein, the terms "cephalosporin C deacetylase" and "cephalosporin C acetyl hydrolase" refers to an enzyme (E.C. 3.1.1.41) that catalyzes the deacetylation of cephalosporins such as cephalosporin C and 7-aminocephalosporanic acid (Mitsushima et al., *Appl. Environ. Microbiol.* 61(6): 2224-2229 (1995); U.S. Pat. No. 5,528,152; and U.S. Pat. No. 5,338,676). As described herein, several cephalosporin C deacetylases are provided having significant perhydrolysis activity.

As used herein, "acetyl xylan esterases" refers to an enzyme (E.C. 311.72; AXEs) that catalyzes the deacetylation of acetylated xylans and other acetylated saccharides. As illustrated herein, several enzymes classified as acetyl xylan esterases are provided having significant perhydrolase activity.

As used herein, the term "*Bacillus subtilis* (ATCC® 31954™)" refers to a bacterial cell deposited to the American Type Culture Collection (ATCC®) having international depository accession number ATCC® 31954™. *Bacillus subtilis* ATCC® 31954™ has been reported to have an ester hydrolase ("diacetinase") activity capable of hydrolyzing glycerol esters having 2-carbon to 8-carbon acyl groups, especially diacetin (U.S. Pat. No. 4,444,886; herein incorporated by reference in its entirety). As described herein, an enzyme having significant perhydrolase activity has been isolated from *B. subtilis* ATCC® 31954™ and is provided as SEQ ID NO: 2. The amino acid sequence of the isolated enzyme has 100% amino acid identity to the cephalosporin C deacetylase provided by GENBANK® Accession No. BAA01729.1.

As used herein, the term "*Bacillus subtilis* BE1010" refers to the strain of *Bacillus subtilis* as reported by Payne and Jackson (*J. Bacteriol.* 173:2278-22.82 (1991)). *Bacillus subtilis* BE1010 is a derivative *Bacillus subtilis* subsp. *subtilis* strain BR151 (ATCC® 33677™) having a chromosomal deletion in the genes encoding subtilisin and neutral protease. As described herein, an enzyme having significant perhydrolase activity has been isolated from *B. subtilis* BE1010 and is provided as SEQ ID NO: 4. The amino acid sequence of the isolated enzyme has 100% amino acid identity to the cephalosporin C deacetylase reported in *Bacillus subtilis* subsp. *subtilis* strain 168 (Kunst et al., *Nature*, 390:249-256 (1997)).

As used herein, the term "*Bacillus subtilis* ATCC® 29233™" refers to a strain of *Bacillus subtilis* deposited to the American Type Culture Collection (ATCC) having international depository accession number ATCC® 29233™. As described herein, an enzyme having significant perhydrolase activity has been isolated and sequenced from *B. subtilis* ATCC® 29233 and is provided as SEQ ID NO: 30.

As used herein, the term "*Clostridium thermocellum* ATCC® 27405™" refers to a strain of *Clostridium thermocellum* deposited to the American Type Culture Collection (ATCC®) having international depository accession number ATCC® 27405™. The amino acid sequence of the enzyme having perhydrolase activity from *C. thermocellum* ATCC® 27405™ is provided as SEQ ID NO: 12.

As used herein, the term "*Bacillus subtilis* ATCC® 6633™" refers to a bacterial cell deposited to the American Type Culture Collection (ATCC®) having international depository accession number ATCC® 6633™. *Bacillus subtilis* ATCC® 6633™ has been reported to have cephalosporin acetylhydrolase activity (U.S. Pat. No. 6,465,233). The amino acid sequence of the enzyme having perhydrolase activity from *B. subtilis* ATCC® 6633™ is provided as SEQ ID NO: 6.

As used herein, the term "*Bacillus licheniformis* ATCC® 14580Th" refers to a bacterial cell deposited to the American Type Culture Collection (ATCC) having international depository accession number ATCC® 14580™. *Bacillus licheniformis* ATCC® 14580™ has been reported to have cephalosporin acetylhydrolase activity (GENBANK® YP_077621). The amino acid sequence of the enzyme having perhydrolase activity from *B. licheniformis* ATCC® 14580™ is provided as SEQ ID NO: 8.

As used herein, the term "*Bacillus pumilus* PS213" refers to a bacterial cell reported to have acetyl xylan esterase activity (GENBANK® AJ249957). The amino acid sequence of the enzyme having perhydrolase activity from *Bacillus pumilus* PS213 is provided as SEQ ID NO: 10.

As used herein, the term "*Thermotoga neapolitana*" refers to a strain of *Thermotoga neapolitana* reported to have acetyl xylan esterase activity (GENBANK® AAB70869). The amino acid sequence of the enzyme having perhydrolase activity from *Thermotoga neapolitana* is provided as SEQ ID NO: 14.

As used herein, the term "*Thermotoga maritima* MSB8" refers to a bacterial cell reported to have acetyl xylan esterase activity (GENBANK® NP_227893.1). The amino acid sequence of the enzyme having perhydrolase activity from *Thermotoga maritima* MSB8 is provided as SEQ ID NO: 16.

As used herein, the term "*Bacillus clausii* KSM-K16" refers to a bacterial cell reported to have cephalosporin-C deacetylase activity (GENBANK® YP_175265). The amino acid sequence of the enzyme having perhydrolase activity from *Bacillus clausii* KSM-K16 is provided as SEQ ID NO: 24.

As used herein, the term "*Thermoanearobacterium saccharolyticum*" refers to a bacterial strain reported to have acetyl xylan esterase activity (GENBANK® 541858). The amino acid sequence of the enzyme having perhydrolase activity from *Thermoanearobacterium saccharolyticum* is provided as SEQ ID NO: 54.

As used herein, the term "*Thermotoga lettingae*" refers to a bacterial cell reported to have acetyl xylan esterase activity (GENBANK® CP000812). The deduced amino acid sequence of the enzyme having perhydrolase activity from *Thermotoga lettingae* is provided as SEQ ID NO: 56.

As used herein, the term "*Thermotoga petrophila*" refers to a bacterial cell reported to have acetyl xylan esterase activity (GENBANK® CP000702). The deduced amino acid sequence of the enzyme having perhydrolase activity from *Thermotoga lettingae* is provided as SEQ ID NO: 58.

As used herein, the term "*Thermotoga* sp. RQ2" refers to a bacterial cell reported to have acetyl xylan esterase activity (GENBANK® CP000969). Two different acetyl xylan esterases have been identified from *Thermotoga* sp. RQ2 and are referred to herein as "RQ2(a)" (the deduced amino acid sequence provided as SEQ ID NO: 60) and "RQ2(b)" (the deduced amino acid sequence provided as SEQ ID NO: 62).

As used herein, an "isolated nucleic acid molecule" and "isolated nucleic acid fragment" will be used interchangeably and refers to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid (or as defined herein) | Xaa | X |

As used herein, "substantially similar" refers to nucleic acid molecules wherein changes in one or more nucleotide bases results in the addition, substitution, or deletion of one or more amino acids, but does not affect the functional properties (i.e., perhydrolytic activity) of the protein encoded by the DNA sequence. As used herein, "substantially similar" also refers to an enzyme having an amino acid sequence that is at least 30%, preferably at least 33%, more preferably at least 40%, more preferably at least 50%, even more preferably at least 60%, even more preferably at least 70%, even more preferably at least 80%, yet even more preferably at least 90%, 91%, 92%, 93%, 94%, 95%, 96%, 97%, 98%, or 99% identical to the amino acid sequences reported herein wherein the resulting enzyme retains the present functional properties perhydrolytic activity). "Substantially similar" may also refer to an enzyme having perhydrolytic activity encoded by nucleic acid molecules that hybridize under stringent conditions to the nucleic acid molecules reported herein. It is therefore understood that the invention encompasses more than the specific exemplary sequences.

For example, it is well known in the art that alterations in a gene which result in the production of a chemically equivalent amino acid at a given site, but do not affect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences are encompassed by the present invention. In one embodiment, substantially similar sequences are defined by their ability to hybridize, under stringent conditions (0.1×SSC, 0.1% SDS, 65° C. and washed with 2×SSC, 0.1% SDS followed by 0.1×SSC, 0.1% SDS, 65° C.) with the sequences exemplified herein. In one embodiment, the present invention includes enzymes having perhydrolase activity encoded by isolated nucleic acid molecules that hybridize under stringent conditions to the nucleic acid molecules reported herein. In a preferred embodiment, the present invention includes an enzyme having perhydrolase activity encoded by isolated nucleic acid molecule that hybridizes under stringent conditions to a nucleic acid molecule having a nucleic acid sequence selected from the group consisting of SEQ ID NO: 1, SEQ ID NO: 9, SEQ ID NO: 13, and SEQ ID NO: 15.

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J. and Russell, D., T. *Molecular Cloning: A Laboratory Manual*, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes from closely related organisms. Post-hybridization washes typically determine stringency conditions. One set of preferred conditions uses a series of washes stating with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of conditions uses higher temperatures in which the washes are identical to those above except for the temperature of the final two 30 min washes in 0.2×SSC, 0.5% SDS was increased to 60° C. Another preferred set of stringent hybridization conditions is 0.1×SSC, 0.1% SDS, 65° C. and washed with 2×SSC, 0.1% SDS followed by a final wash of 0.1×SSC, 0.1% SDS, 65° C. with the sequences exemplified herein.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (Sambrook and Russell, supra). For hybridizations with shorter nucleic acids, i.e., oligonucleotides, the position of mismatches becomes more important, and the length of the oligonucleotide determines its specificity (Sambrook and Russell, supra). In one aspect, the length for a hybridizable nucleic acid is at least about 10 nucleotides. Preferably, a minimum length for a hybridizable nucleic acid is at least about 15 nucleotides in length, more preferably at least about 20 nucleotides in length, even more preferably at least 30 nucleotides in length, even more preferably at least 300 nucleotides in length, and most preferably at least 800 nucleotides in length. Furthermore, the skilled artisan will recognize that the temperature and wash solution salt concentration may be adjusted as necessary according to factors such as length of the probe.

As used herein, the term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs. Sequence alignments and percent identity calculations may be performed using the Megalign program of the LASERGENE bioinformatics computing suite (DNASTAR Inc., Madison, Wis.), the AlignX program of Vector NTI v. 7.0 (Informax, Inc., Bethesda, Md.), or the EMBOSS Open Software Suite (EMBL-EBI; Rice et al., *Trends in Genetics* 16, (6) pp 276-277 (2000)). Multiple alignment of the sequences can be performed using the Clustal method (i.e., CLUSTALW; for example version 1.83) of alignment (Higgins and Sharp, *CABIOS,* 5:151-153 (1989); Higgins et al., *Nucleic Acids Res.,* 22:4673-4680 (1994); and Chema et al., *Nucleic Acids Res.,* 31 (13):3497-500 (2003)), available from the European Molecular Biology Laboratory via the European Bioinformatics Institute) with the default parameters. Suitable parameters for CLUSTALW protein alignments include GAP Existence penalty=15, GAP extension=0.2, matrix=Gonnet (e.g., Gonnet250), protein ENDGAP=−1, Protein GAPDIST=4, and KTUPLE=1. In one embodiment, a fast or slow alignment is used with the default settings where a slow alignment is preferred. Alternatively, the parameters using the CLUSTALW method (version 1.83) may be modified to also use KTUPLE=1, GAP PENALTY=10, GAP extension=1, matrix=BLOSUM (e.g. BLOSUM64), WINDOW=5, and TOP DIAGONALS SAVED=5.

In one aspect of the present invention, suitable isolated nucleic acid molecules (isolated polynucleotides of the present invention) encode a polypeptide having an amino acid sequence that is at least about 30%, preferably at least 33%, preferably at least 40%, preferably at least 50%, preferably at least 60%, more preferably at least 70%, more preferably at least 80%, even more preferably at least 85%, even more preferably at least 90%, 91%, 92%, 93%, 94%, 95%, 96%, 97%, 98%, or 99% identical to the amino acid sequences reported herein. Suitable nucleic acid molecules of the present invention not only have the above homologies, but also typically encode a polypeptide having about 300 to about 340 amino acids, more preferably about 310 to about 330 amino acids, and most preferably about 318 amino acids.

As used herein, the terms "signature motif", "CE-7 signature motif", and "diagnostic motif" refer to conserved structures shared among a family of enzymes having a defined activity. The signature motif can be used to define and/or identify the family of structurally related enzymes having similar enzymatic activity for a defined family of substrates. The signature motif can be a single contiguous amino acid sequence or a collection of discontiguous, conserved motifs that together form the signature motif. Typically, the conserved motif(s) is represented by an amino acid sequence. As described herein, the present perhydrolases belong to the family of CE-7 carbohydrate esterases. This family of enzymes can be defined by the presence of a signature motif (Vincent et al., supra).

As used herein, "codon degeneracy" refers to the nature of the genetic code permitting variation of the nucleotide sequence without affecting the amino acid sequence of an encoded polypeptide. Accordingly, the present invention relates to any nucleic acid molecule that encodes all or a substantial portion of the amino acid sequences encoding the present microbial polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

As used herein, "synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as pertaining to a DNA sequence, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequences to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, "gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different from that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-loop structure.

As used herein, "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene at different stages of development, or in response to different environmental or physiological conditions. Promoters that cause a gene to be expressed at most times are commonly referred to as "constitutive promoters". It is further recognized that since in most cases the exact boundaries of regulatory sequences have not been completely defined, DNA fragments of different lengths may have identical promoter activity.

As used herein, the "3' non-coding sequences" refer to DNA sequences located downstream of a coding sequence and include polyadenylation recognition sequences (normally limited to eukaryotes) and other sequences encoding regulatory signals capable of affecting mRNA processing or gene expression. The polyadenylation signal is usually characterized by affecting the addition of polyadenylic acid tracts (normally limited to eukaryotes) to the 3' end of the mRNA precursor.

As used herein, the term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., that the coding sequence is under the transcriptional control of the promoter. Coding sequences can be operably linked to regulatory sequences in sense or antisense orientation.

As used herein, the term "expression" refers to the transcription and stable accumulation of sense (mRNA) or antisense RNA derived from the nucleic acid molecule described herein. Expression may also refer to translation of mRNA into a polypeptide.

As used herein, "transformation" refers to the transfer of a nucleic acid molecule into the genome of a host organism, resulting in genetically stable inheritance. In the present invention, the host cell's genome includes chromosomal and extrachromosomal (e.g. plasmid) genes. Host organisms containing the transformed nucleic acid molecules are referred to as "transgenic" or "recombinant" or "transformed" organisms.

As used herein, the terms "plasmid", "vector" and "cassette" refer to an extrachromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

As used herein, the term "sequence analysis software" refers to any computer algorithm or software program that is useful for the analysis of nucleotide or amino acid sequences. "Sequence analysis software" may be commercially available or independently developed. Typical sequence analysis software will include, but is not limited to, the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNASTAR (DNASTAR, Inc. 1228 S. Park St. Madison, Wis. 53715 USA), CLUSTALW (for example, version 1.83; Thompson et al., *Nucleic Acids Research,* 22(22):4673-4680 (1994), and the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Publisher: Plenum, New York, N.Y.), Vector NTI (Informax, Bethesda, Md.) and Sequencher v. 4.05. Within the context of this application it will be understood that where sequence analysis software is used for analysis, that the results of the analysis will be based on the "default values" of the program referenced, unless otherwise specified. As used herein "default values" will mean any set of values or parameters set by the software manufacturer that originally load with the software when first initialized.

As used herein, the term "biological contaminants" refers to one or more unwanted and/or pathogenic biological entities including, but not limited to, microorganisms, spores, viruses, prions, and mixtures thereof. The process produces an efficacious concentration of at least one percarboxylic acid useful to reduce and/or eliminate the presence of the viable biological contaminants. In a preferred embodiment, the microbial contaminant is a viable pathogenic microorganism.

As used herein, the term "disinfect" refers to the process of destruction of or prevention of the growth of biological contaminants. As used herein, the term "disinfectant" refers to an agent that disinfects by destroying, neutralizing, or inhibiting the growth of biological contaminants. Typically, disinfectants are used to treat inanimate objects or surfaces. As used herein, the term "antiseptic" refers to a chemical agent that inhibits the growth of disease-carrying microorganisms. In one aspect of the embodiment, the biological contaminants are pathogenic microorganisms.

As used herein, the term "virucide" refers to an agent that inhibits or destroys viruses, and is synonymous with "viricide". An agent that exhibits the ability to inhibit or destroy viruses is described as having "virucidal" activity. Peracids can have virucidal activity. Typical alternative virucides known in the art which may be suitable for use with the present invention include, for example, alcohols, ethers, chloroform, formaldehyde, phenols, beta propiolactone, iodine, chlorine, mercury salts, hydroxylamine, ethylene oxide, ethylene glycol, quaternary ammonium compounds, enzymes, and detergents.

As used herein, the term "biocide" refers to a chemical agent, typically broad spectrum, which inactivates or destroys microorganisms. A chemical agent that exhibits the ability to inactivate or destroy microorganisms is described as having "biocidal" activity. Peracids can have biocidal activity. Typical alternative biocides known in the art, which may be suitable for use in the present invention include, for example, chlorine, chlorine dioxide, chloroisocyanurates, hypochlorites, ozone, acrolein, amines, chlorinated phenolics, copper salts, organo-sulphur compounds, and quaternary ammonium salts.

As used herein, the phrase "minimum biocidal concentration" refers to the minimum concentration of a biocidal agent that, for a specific contact time, will produce a desired lethal, irreversible reduction in the viable population of the targeted microorganisms. The effectiveness can be measured by the $\log_{10}$ reduction in viable microorganisms after treatment. In one aspect, the targeted reduction in viable microorganisms after treatment is at least a 3-log reduction, more preferably at least a 4-log reduction, and most preferably at least a 5-log reduction. In another aspect, the minimum biocidal concentration is at least a 6-log reduction in viable microbial cells.

As used herein, the terms "peroxygen source" and "source of peroxygen" refer to compounds capable of providing hydrogen peroxide at a concentration of about 1 mM or more when in an aqueous solution including, but not limited to, hydrogen peroxide, hydrogen peroxide adducts (e.g., urea-hydrogen peroxide adduct (carbamide peroxide)), perborates, and percarbonates. As described herein, the concentration of the hydrogen peroxide provided by the peroxygen compound in the aqueous reaction mixture is initially at least 1 mM or more upon combining the reaction components. In one embodiment, the hydrogen peroxide concentration in the aqueous reaction mixture is at least 10 mM. In another embodiment, the hydrogen peroxide concentration in the aqueous reaction mixture is at least 100 mM. In another embodiment, the hydrogen peroxide concentration in the aqueous reaction mixture is at least 200 mM. In another embodiment, the hydrogen peroxide concentration in the aqueous reaction mixture is 500 mM or more. In yet another embodiment, the hydrogen peroxide concentration in the aqueous reaction mixture is 1000 mM or more. The molar ratio of the hydrogen peroxide to enzyme substrate, e.g. triglyceride, ($H_2O_2$:substrate) in the aqueous reaction mixture may be from about 0.002 to 20, preferably about 0.1 to 10, and most preferably about 0.5 to 5. Alternatively, a peroxygen source (e.g., hydrogen peroxide) can be generated in situ by the reaction of a substrate and oxygen catalyzed by an enzyme having oxidase activity (e.g., glucose oxidase, alcohol oxidase, monoamine oxidase, lactate oxidase, amino acid oxidase).

Suitable Reaction Conditions for Controlling the Enzyme-Catalyzed Preparation of Peracids from Carboxylic Acid Esters and Hydrogen Peroxide In one aspect, a process is provided to produce an aqueous mixture comprising a target concentration of peracid by reacting carboxylic acid esters and an inorganic peroxide, not limited to hydrogen peroxide, sodium perborate or sodium percarbonate, in the presence of an enzyme catalyst having pH-sensitive perhydrolysis activity. In one embodiment, the enzyme catalyst comprises a perhydrolase having a structure belonging to the CE-7 carbohydrate esterase family.

In another embodiment, the perhydrolase catalyst is structurally classified as a cephalosporin C deacetylase. In another embodiment, the perhydrolase catalyst is structurally classified as an acetyl xylan esterase.

In one embodiment, the perhydrolase catalyst comprises an enzyme having a CE-7 signature motif that aligns with a reference sequence SEQ ID NO: 2 using CLUSTALW, said signature motif comprising:

i) an RGQ motif at amino acid positions 118-120 of SEQ ID NO:2;
ii) a GXSQG motif at amino acid positions 179-183 of SEQ ID NO:2; and
iii) an HE motif at amino acid positions 298-299 of SEQ ID NO:2;

wherein said enzyme also comprises at least 30% amino acid identity to SEQ ID NO: 2.

In a further embodiment, the signature motif additional comprises a forth conserved motif defined as an LXD motif at amino acid residues 267-269 when aligned to reference sequence SEQ ID NO: 2 using CLUSTALW.

In another embodiment, the perhydrolase catalyst comprises an enzyme having an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 30, SEQ ID NO: 54, SEQ ID NO: 56, SEQ ID NO: 58, SEQ ID NO: 60, and SEQ ID NO: 62, or a substantially similar enzyme having perhydrolase activity derived by substituting, deleting or adding one or more amino acids to said amino acid sequence.

In another embodiment, a substantially similar enzyme having an amino acid sequence that is at least 90%, 91%, 92%, 93%, 94%, 95%, 96%, 97%, 98%, or 99% identical to one or more amino acid sequences selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 30, SEQ ID NO: 54, SEQ ID NO: 56, SEQ ID NO: 58, SEQ ID NO: 60, and SEQ ID NO: 62.

In another embodiment, the perhydrolase catalyst comprises an enzyme having an amino acid sequence encoded by a nucleic acid molecule that hybridizes to a nucleic acid sequence selected from the group consisting of SEQ ID NO: 1; SEQ ID NO: 3; SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 29, SEQ ID NO: 55, SEQ ID NO: 57, SEQ ID NO: 59, and SEQ ID NO: 61 under stringent hybridization conditions.

In another embodiment, the perhydrolase catalyst comprises an enzyme having at least 30%, preferably at last 36%, amino acid identity to a contiguous signature motif defined as SEQ ID NO: 61 wherein the conserved motifs described above (e.g. RGQ, GXSQG, and LIE, and optionally, LXD) are conserved.

In one embodiment, suitable substrates include esters provided by the following formula:

wherein X=an ester group of the formula $R_6C(O)O$
$R_6$=C1 to C7 linear, branched or cyclic hydrocarbyl moiety, optionally substituted with hydroxyl groups or C1 to C4 alkoxy groups, wherein $R_6$ optionally comprises one or more ether linkages for R6=C2 to C7;

$R_5$=a C1 to C6 linear, branched, or cyclic hydrocarbyl moiety optionally substituted with hydroxyl groups; wherein each carbon atom in $R_5$ individually comprises no more than one hydroxyl group or no more than one ester group; wherein $R_5$ optionally comprises one or more ether linkages;

m=1 to the number of carbon atoms in $R_5$; and wherein said esters have a solubility in water of at least 5 ppm at 25° C.

In another embodiment, suitable substrates also include esters of the formula:

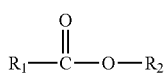

wherein $R_1$=C1 to C7 straight chain or branched chain alkyl optionally substituted with an hydroxyl or a C1 to C4 alkoxy group and $R_2$=$C_1$ to $C_{10}$ straight chain or branched chain alkyl, alkenyl, alkynyl, aryl, alkylaryl, alkylheteroaryl, heteroaryl, $(CH_2CH_2$—$O)_n H$ or $(CH_2CH(CH_3)$—$O)_n H$ and n=1 to 10.

In another embodiment, suitable substrates include glycerides of the formula:

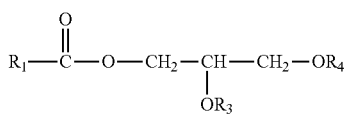

wherein $R_1$=C1 to C7 straight chain or branched chain alkyl optionally substituted with an hydroxyl or a C1 to C4 alkoxy group and $R_3$ and $R_4$ are individually H or $R_1C(O)$.

In another embodiment, $R_6$ is C1 to C7 linear hydrocarbyl moiety, optionally substituted with hydroxyl groups or C1 to C4 alkoxy groups, optionally comprising one or more ether linkages. In a further preferred embodiment, $R_6$ is C2 to C7 linear hydrocarbyl moiety, optionally substituted with hydroxyl groups, and/or optionally comprising one or more ether linkages.

In another embodiment, suitable substrates also include acetylated saccharides selected from the group consisting of acetylated mono-, di-, and polysaccharides. In a preferred embodiment, the acetylated saccharides include acetylated mono-, di-, and polysaccharides. In another embodiment, the acetylated saccharides are selected from the group consisting of acetylated xylan, fragments of acetylated xylan, acetylated xylose (such as xylose tetraacetate), acetylated glucose (such as glucose pentaacetate), β-D-ribofuranose-1,2,3,5-tetraacetate, tri-O-acetyl-D-galactal, and tri-O-acetyl-D-glucal, and acetylated cellulose. In a preferred embodiment, the acetylated saccharide is selected from the group consisting of β-D-ribofuranose-1,2,3,5-tetraacetate, tri-O-acetyl-D-galactal, and tri-O-acetyl-D-glucal, and acetylated cellulose. As such, acetylated carbohydrates may be suitable substrates for generating percarboxylic acids using the present process (i.e., in the presence of a peroxygen source).

In one embodiment, the substrate is selected from the group consisting of: monoacetin; diacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-glucal; monoesters or diesters of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,6-pentanediol, 1,2-hexanediol, 2,5-hexanediol, 1,6-hexanediol; and mixtures thereof.

In a preferred embodiment, the substrate is selected from the group consisting of ethyl acetate, methyl lactate, ethyl lactate, methyl glycolate, ethyl glycolate, methyl methoxyacetate, ethyl methoxyacetate, methyl 3-hydroxybutyrate, ethyl 3-hydroxybutyrate, triethyl 2-acetyl citrate, glucose pentaacetate, gluconolactone, glycerides (mono-, di-, and triglycerides) such as monoacetin, diacetin, triacetin, monopropionin, dipropionin (glyceryl dipropionate), tripropionin (1,2,3-tripropionylglycerol), monobutyrin, dibutyrin (glyceryl dibutyrate), tributyrin (1,2,3-tributyrylglycerol), acetylated saccharides, and mixtures thereof.

In a further preferred aspect, the carboxylic acid ester substrates are selected from the group consisting of monoacetin, diacetin, triacetin, monopropionin, dipropionin, tripropionin, monobutyrin, dibutyrin, tributyrin, ethyl acetate, and ethyl lactate. In yet another aspect, the carboxylic acid ester substrates are selected from the group consisting of diacetin, triacetin, ethyl acetate, and ethyl lactate. In a preferred aspect, the carboxylic acid ester is a glyceride selected from the group consisting of monoacetin, diacetin, triacetin, and mixtures thereof.

The carboxylic acid ester is present in the reaction mixture at a concentration sufficient to produce the desired concentration of peracid upon enzyme-catalyzed perhydrolysis. The carboxylic acid ester need not be completely soluble in the reaction mixture, but has sufficient solubility to permit conversion of the ester by the perhydrolase catalyst to the corresponding peracid. The carboxylic acid ester is present in the reaction mixture at a concentration of 0.0005 wt % to 40 wt % of the reaction mixture, preferably at a concentration of 0.1 wt % to 20 wt % of the reaction mixture, and more preferably at a concentration of 0.5 wt % to 10 wt % of the reaction mixture. The wt % of carboxylic acid ester may optionally be greater than the solubility limit of the carboxylic acid ester, such that the concentration of the carboxylic acid ester is at least 0.0005 wt % in the reaction mixture that is comprised of water, enzyme catalyst, and source of peroxide, where the remainder of the carboxylic acid ester remains as a second separate phase of a two-phase aqueous/organic reaction mixture. Not all of the added carboxylic acid ester must immediately dissolve in the aqueous reaction mixture, and after an initial mixing of all reaction components, additional continuous or discontinuous mixing is optional.

The peroxygen source may include, but is not limited to, hydrogen peroxide, hydrogen peroxide adducts (e.g., urea-hydrogen peroxide adduct (carbamide peroxide)) perborate salts and percarbonate salts. The concentration of peroxygen compound in the reaction mixture may range from 0.0033 wt % to about 50 wt %, preferably from 0.033 wt % to about 40 wt %, more preferably from 0.33 wt % to about 30 wt %.

Many perhydrolase catalysts (whole cells, permeabilized whole cells, and partially purified whole cell extracts each containing an enzyme having perhydrolase activity) have been reported to also have one or more enzymes having catalase activity (EC 1.11.1.6). Catalases catalyze the conversion of hydrogen peroxide into oxygen and water. In one aspect, the perhydrolysis catalyst lacks catalase activity. In another aspect, a catalase inhibitor is added to the reaction mixture. Examples of catalase inhibitors include, but are not limited to, sodium azide and hydroxylamine sulfate. One of skill in the art can adjust the concentration of catalase inhibitor as needed. The concentration of the catalase inhibitor typically ranges from 0.1 mM to about 1 M; preferably about 1 mM to about 50 mM; more preferably from about 1 mM to about 20 mM. In one aspect, sodium azide concentration typically ranges from about 20 mM to about 60 mM while hydroxylamine sulfate is concentration is typically about 0.5 mM to about 30 mM, preferably about 10 mM.

In another embodiment, the perhydrolase catalyst lacks significant catalase activity or is engineered to decrease or eliminate catalase activity. The catalase activity in a host cell can be down-regulated or eliminated by disrupting expression of the gene(s) responsible for the catalase activity using well known techniques including, but not limited to, transposon mutagenesis, RNA antisense expression, targeted mutagenesis, and random mutagenesis. In a preferred embodiment, the gene(s) encoding the endogenous catalase activity are down-regulated or disrupted (i.e. knocked-out). As used herein, a "disrupted" gene is one where the activity and/or function of the protein encoded by the modified gene is no longer present. Means to disrupt a gene are well-known in the art and may include, but are not limited to insertions, deletions, or mutations to the gene so long as the activity and/or function of the corresponding protein is no longer present. In a further preferred embodiment, the production host is an *E. coli* production host comprising a disrupted catalase gene selected from the group consisting of katG (SEQ ID NO: 40) and katE (SEQ ID NO: 49). In another embodiment, the production host is an *E. coli* strain comprising a down-regulation and/or disruption in both katg1 and a katE catalase genes. An *E. coli* strain comprising a double-knockout of katG and katE is provided herein (see Example 3; *E. coli* strain KLP18).

The catalase negative *E. coli* strain KLP18 (katG and katE double knockout) that was constructed (Example 3) was demonstrated to be a superior host for large scale (10-L and greater) production of perhydrolase enzymes compared to the catalase negative strain UM2 (*E. coli* Genetic Stock Center #7156, Yale University, New Haven Conn.), as determined by growth under fermenter conditions. Although both KLP18 and UM2 are catalase-negative strains, UM2 is known to have numerous nutritional auxotrophies, and therefore requires media that is enriched with yeast extract and peptone. Even when employing enriched media for fermentation, UM2 grew poorly and to a limited maximum cell density (OD). In contrast, KLP18 had no special nutritional requirements and grew to high cell densities on mineral media alone or with additional yeast extract.

The concentration of the perhydrolase catalyst in the aqueous reaction mixture depends on the specific catalytic activity of the catalyst, and is chosen to obtain the desired rate of reaction. The weight of perhydrolase catalyst in perhydrolysis reactions typically ranges from 0.0001 mg to 10 mg per mL of total reaction volume, preferably from 0.001 mg to 1.0 mg per mL. The catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. The use of immobilized catalysts permits the recovery and reuse of the catalyst in subsequent reactions. The enzyme catalyst may be in the form of whole microbial cells, permeabilized microbial cells, microbial cell extracts, partially-purified or purified enzymes, and mixtures thereof.

In one aspect, the concentration of peracid generated by the combination of chemical perhydrolysis and enzymatic perhydrolysis of the carboxylic acid ester is sufficient to provide an effective concentration of peracid for bleaching or disinfection at a desired pH. In another aspect, the present methods provide combinations of enzymes and enzyme substrates to produce the desired effective concentration of peracid, where, in the absence of added enzyme, there is a significantly lower concentration of peracid produced. Although there may in some cases be substantial chemical perhydrolysis of the enzyme substrate by direct chemical reaction of inorganic peroxide with the enzyme substrate, there may not be a sufficient concentration of peracid generated to provide an effective concentration of peracid in the desired applications, and a significant increase in total peracid concentration is achieved by the addition of an appropriate perhydrolase catalyst to the reaction mixture.

Peracids can be corrosive to certain metal surfaces, caustic to users, or otherwise destructive, so it may be desirable to limit the total amount of peracid produced during the reaction to prevent or minimize its corrosive effect. For example, applications that require production of no more than about 100 to about 1000 ppm of peracid in about 1 minute to about 5 minutes often employ reaction conditions that yield a final concentration of peracid well above this limit. In such instances it can be desirable to regulate the amount of peracid produced and, in some cases, to regulate the rate at which the peracid is produced.

As described herein, an aqueous reaction mixture can produce a limited amount of peracid if the proper reaction conditions are used. One component of the reaction mixture that can be important in this regard is a buffer, specifically the pKa and concentration of the buffer. These characteristics of the buffer can regulate the pH of the reaction mixture as peracids are produced, and where byproduct carboxylic acids may also be produced by the enzyme-catalyzed hydrolysis of peracid to carboxylic acid and hydrogen peroxide; therefore, selecting a buffer with the proper characteristics is one way to control, or inactivate, the catalytic activity of a pH-sensitive enzyme catalyst in order to produce a target concentration of peracid. The buffer may be any buffer suitable for carrying out an enzymatic perhydrolysis reaction at the desired pH. In some aspects, the buffer is selected from the group consisting of the sodium salt, the potassium salt or mixed sodium and potassium salts of bicarbonate buffer, citrate buffer, methylphosphonate buffer, pyrophosphate buffer and phosphate buffer. In some aspects, the buffer is bicarbonate buffer or citrate buffer. In some aspects, the aqueous reaction mixture having a specific initial pH includes a buffer.

One way to control the amount of peracid produced by an enzyme-driven reaction is to use reaction conditions that selectively reduce, or inactivate, the catalytic function of the enzyme. Accordingly, the initial pH of the reaction mixture may be adjusted such that the pH of the reaction falls as peracid is produced, ultimately resulting in the reaction mixture having a pH that prevents efficient, or substantial, enzyme activity. In one embodiment, the initial pH of the reaction mixture is about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, or about 8.5.

In some aspects, the buffer included in the aqueous reaction mixture can establish the initial pH of the reaction mixture. In some aspects, the buffer produces an aqueous reaction mixture with an initial pH of about 4.0 to about 10.0. In some aspects, the buffer produces an aqueous reaction mixture with an initial pH of about 5.0 to about 9.0. In some aspects, the buffer produces an aqueous reaction mixture with an initial pH of about 6.0 to about 8.5. In some aspects, the buffer produces an aqueous reaction mixture with an initial pH of about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, or about 8.5. In some aspects, the reaction mixture containing a buffer has an initial pH of about 8.1. In some aspects, the buffer in a reaction mixture having an initial pH of about 8.1 is bicarbonate buffer. In some aspects, the reaction mixture containing a buffer has an initial pH of about 7.2. In some aspects, the buffer in a reaction mixture having an initial pH of about 7.2 is citrate buffer. In some aspects, the buffer in a reaction mixture having an initial pH of about 7.2 is bicarbonate buffer. In some aspects, the buffer in a reaction mixture having an initial pH of about 7.2 is phosphate buffer. In some aspects, the reaction mixture containing a buffer has an initial pH of about 6.5. In some aspects, the buffer in a reaction mixture having an initial pH of about 6.5 is citrate buffer. In some aspects, the buffer in a reaction mixture having an initial pH of about 6.5 is bicarbonate buffer. In some aspects, the buffer in a reaction mixture having an initial pH of about 6.5 is phosphate buffer. In some aspects, the reaction mixture containing a buffer has an initial pH of about 6.0. In some aspects, the buffer in a reaction mixture having an initial pH of about 6.0 is citrate buffer. In some aspects, the buffer in a reaction mixture having an initial pH of about 6.0 is bicarbonate buffer. In some aspects, the buffer in a reaction mixture having an initial pH of about 6.0 is phosphate buffer. In some aspects, the reaction mixture containing a buffer has an initial pH of about 5.5. In some aspects, the buffer in a reaction mixture having an initial pH of about 5.5 is citrate buffer. In some aspects, the buffer in a reaction mixture having an initial pH of about 5.5 is bicarbonate buffer.

As described herein, an aqueous reaction mixture can produce a limited amount of peracid if the proper reaction conditions are used. One aspect of the reaction mixture that can be important in this regard is buffer concentration. For example, a dilute buffer has limited capacity to buffer the reaction mixture as peracid is produced, thereby reducing the pH of the reaction mixture and reducing, or inactivating, enzyme activity. The concentration of the buffer can regulate the pH of the reaction mixture as peracids are produced; therefore, selecting a buffer with the proper concentration is one way to control, or inactivate, the catalytic activity of a pH-sensitive enzyme catalyst to produce a target concentration of peracid. Accordingly, in some aspects, the aqueous reaction mixture includes a buffer having a specific concentration. The buffer may be any buffer suitable for carrying out an enzymatic perhydrolysis reaction. In some aspects, the buffer is selected from the group consisting of, but not limited to, the sodium salt, potassium salt, or mixture of sodium and potassium salts of bicarbonate buffer, citrate buffer, acetate buffer, phosphate buffer, pyrophosphate buffer and methylphosphonate buffer. In some aspects, the buffer is sodium bicarbonate buffer or sodium citrate buffer. In some aspects, the buffer has a concentration of about 0.01 mM to about 200 mM. In some aspects, the buffer has a concentration of about 0.01 mM to about 100 mM. In some aspects, the buffer has a concentration of about 0.01 mM to about 50 mM. In some aspects, the buffer has a concentration of about 100, 95, 90, 85, 80, 75, 70, 65, 60, 55, 50, 45, 40, 35, 30, 25, 20, 15, 10, 5 2.5, 1, 0.5, or about 0.1 mM. In some aspects, the buffer has a concentration of about 50 mM. In some aspects, the buffer having an initial concentration of about 50 mM is citrate buffer. In some aspects, the buffer having an initial concentration of about 50 mM is bicarbonate buffer. In some aspects, the buffer has a concentration of about 25 mM to about 1 mM. In some aspects, the buffer having an initial concentration of about 25 mM to about 1 mM is citrate buffer. In some aspects, the buffer having an initial concentration of about 25 mM to about 1 mM is bicarbonate buffer.

The amount of peracid produced by an enzyme-driven reaction can also be regulated by selecting a reaction mixture initial pH and a buffer with a pKa that will cause the pH of the reaction mixture to fall such that the enzymatic activity of the reaction is reduced or inactivated once the desired concentration of peracid is produced. In one aspect, the initial pH of the reaction mixture is about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, or about 8.5 and the pKa of the buffer is about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0 or about 8.1.

In another embodiment, an enzyme catalyst sensitive to acidic pH, where the enzyme activity decreases significantly with decreasing pH, could be used to control an enzyme-catalyzed reaction because the production of peracid would cause the pH of the reaction mixture to fall to a point at which catalytic activity would be reduced significantly or inactivated. In reactions where the enzyme activity may also catalyze the hydrolysis of peracid to carboxylic acid and hydrogen peroxide, the production of carboxylic acid may also cause the pH of the reaction mixture to fall to a point at which catalytic activity would be reduced significantly or inactivated. For example, in one embodiment, total protein extract from B. subtilis ATCC® 31954™ could be used as a catalyst. In another embodiment, a particular enzyme from B. subtilis ATCC® 31954™ having perhydrolase activity could be used as a catalyst. In one embodiment, total protein extract from B. pumilus could be used as a catalyst. In another embodiment, a particular enzyme from B. pumilus having perhydrolase activity could be used as a catalyst. In one embodiment, total protein extract from T. neapolitana could be used as a catalyst. In another embodiment, a particular protein from T. neapolitana having perhydrolase activity could be used as a catalyst. In one embodiment, total protein extract from T. maritima could be used as a catalyst. In another embodiment, a particular protein from T. maritima having perhydrolase activity could be used as a catalyst.

The production of peracid in an aqueous reaction mixture can alter the enzymatic activity of an enzyme catalyzing the production of peracid. For example, production of peracid can lower the pH of the reaction mixture, which can reduce or inactivate the activity of an enzyme catalyst. In reactions where the enzyme activity may also catalyze the hydrolysis of peracid to carboxylic acid and hydrogen peroxide, the production of carboxylic acid may also cause the pH of the reaction mixture to fall to a point at which catalytic activity would be reduced significantly or inactivated. Accordingly, in some aspects, the production of peracid or peracid and carboxylic acid reduces the activity of an enzyme catalyst by about 25% to about 100%. In some aspects, the production of peracid or peracid and carboxylic acid reduces the activity of an enzyme catalyst by about 40% to about 90%. In some aspects, the production of peracid or peracid and carboxylic acid reduces the activity of an enzyme catalyst by about 60% to about 80%. In some aspects, the production of peracid or peracid and carboxylic acid reduces the activity of an enzyme catalyst by about 50%, 55%, 60%, 65%, 70%, 75%, 80%, 85%, 90%, 95% or about 100%. In some aspects, the production of peracid or peracid and carboxylic acid reduces the pH of the reaction mixture such that the activity of the enzyme catalyst is reduced by at least about 75%. In some aspects, the production of peracid or peracid and carboxylic acid reduces the pH of the reaction mixture such that the activity of the enzyme catalyst is reduced by at least about 85%. The pH of the final reaction mixture containing peracid is from about 2 to about 9. In some embodiments the pH of the final reaction mixture containing peracid is from about 3 to about 8, more preferably from about 4 to about 7. In some embodiments the pH of the final reaction mixture containing peracid is from about 5 to about 6. In some embodiments the pH of the final reaction mixture containing peracid is from about 5 to about 5.5. In some embodiments the pH of the final reaction mixture containing peracid is from about 4.5 to about 5.

The concentration of peracid generated (e.g. peracetic acid) by the perhydrolysis of at least one carboxylic acid ester is at least about 2 ppm, preferably at least 20 ppm, more preferably at least 100 ppm, more preferably at least 200 ppm, more preferably at least 300 ppm, more preferably at least 500 ppm, more preferably at least 800 ppm, more preferably at least about 1000 ppm within 10 minutes, preferably within 5 minutes, and most preferably within 1 minute of initiating the perhydrolysis reaction. In some aspects, the concentration of peracid generated (e.g. peracetic acid) by the perhydrolysis of at least one carboxylic acid ester is from about 100 ppm to about 1200 ppm, but is not more that about 2500 ppm, within 10 minutes, preferably within 5 minutes, and most preferably within 1 minute of initiating the perhydrolysis reaction. More preferably, the concentration of peracid generated by the perhydrolysis of at least one carboxylic acid ester is from about 400 ppm to about 600 ppm, within 10 minutes, preferably within 5 minutes, and most preferably within 1 minute of initiating the perhydrolysis reaction. The product mixture comprising the peracid may be optionally diluted with water, or a solution predominantly comprised of water, to produce a mixture with the desired lower concentration of peracid. In one aspect, the reaction time required to produce the desired concentration of peracid is not greater than about two hours, preferably not greater than about 30 minutes, more preferably not greater than about 10 minutes, even more preferably not greater than about 5 minutes, and most preferably in about 1 minute or less. In other aspects, a hard surface or inanimate object contaminated with a concentration of a microbial population is contacted with the peracid formed in accordance with the processes described herein within about 1 minute to about 168 hours of combining said reaction components, or within about 1 minute to about 48 hours, or within about 1 minute to 2 hours of combining said reaction components, or any such time interval therein.

In an application for in situ generation of peracetic acid for disinfection of hard surfaces, it can be desirable to rapidly generate a sufficient amount of peracid to disinfect a hard surface, without significantly exceeding the upper efficacious concentration, thereby limiting or preventing the corrosion of the surface. Peracids can be produced in this manner using enzyme-catalyzed reactions having the appropriate buffer, pH, and enzyme concentrations and using an enzyme that is significantly reduced in activity or inactivated by a decrease in pH. Accordingly, in one aspect, the enzyme-catalyzed reaction mixture incorporates a catalytic enzyme that loses activity after producing from about 500 ppm to about 600 ppm of peracid, due to the acidic pH of the reaction mixture once the desired amount of peracid is produced. This sort of reaction mixture can be modified in other embodiments to cause the catalytic enzyme to lose activity after the production of from about 100 ppm to about 200 ppm of peracid, from about 200 ppm to about 300 ppm of peracid, from about 300 ppm to about 400 ppm of peracid, from about 400 ppm to about 500 ppm of peracid, from about 600 ppm to about 700 ppm of peracid, from about 700 to about 800 ppm of peracid, from about 800 ppm to about 900 ppm of peracid, from about 900 ppm to about 1000 ppm of peracid, or from about 100 ppm to about 500 ppm of peracid, from about 500 ppm to about 1000 ppm of peracid, or from about 1000 ppm to about 2000 ppm of peracid, as needed based on the particular application.

In some aspects, it is also important to produce peracids in a short period of time; however, many of these applications also require production of only a fixed amount of peracid. For example, it can be desirable for a mixture giving rise to a peracid-based disinfectant solution to produce only from about 100 ppm to about 1200 ppm of peracid in about 1 minute, such that substantial amounts of peracid are not produced following the first minute of production. Accordingly, provided herein are enzyme-catalyzed reactions for producing peracids in concentrations from about 100 ppm to about 1200 ppm are produced in about 1 minute without significant production of peracids thereafter.

Of course, those of skill in the art will recognize that other reaction conditions relating to pH, pKa, buffer concentration, and catalyst activity/pH sensitivity will provide the means to limit peracid production by the methods described herein. Such conditions and uses thereof are within the scope of this disclosure.

Described are aqueous peracid solutions that maintain a relatively stable concentration of peracid, i.e. within about 20% of a target peracid concentration, after the reduction, or inactivation, of the enzyme-catalyzed production of peracid, and methods for generating such stable peracid solutions. In one embodiment, the stability of the aqueous reaction product comprising the target concentration of peracid concentration is measured in a closed system (for example, a reaction chamber or a container made of a material that does not substantially react with (or enhance degradation of) the peroxycarboxylic acid produced) at room temperature (approximately 21-22° C.). In some preferred embodiments, the aqueous peracid solutions maintain a peracid concentration within about 15%, and more preferably within about 10%, of a target peracid concentration, after the reduction, or inactivation, of the enzyme-catalyzed production of peracid. The stability of the peracid concentration can persist for hours after the reduction, or inactivation, of the enzyme-catalyzed production of peracid. In one embodiment, the peracid concentration is stable for about 3 hours after the enzyme-catalyzed production of peracid is over. In another embodiment, the peracid concentration is stable for about 6 hours after the enzyme-catalyzed production of peracid is over. In one embodiment, the peracid concentration is stable for about 9 hours after the enzyme-catalyzed production of peracid is over. In one embodiment, the peracid concentration is stable for about 12 hours after the enzyme-catalyzed production of peracid is over. In another embodiment, the peracid concentration is stable for about 15 hours after the enzyme-catalyzed production of peracid is over. In another embodiment, the peracid concentration is stable for about 18 hours after the enzyme-catalyzed production of peracid is over. In one embodiment, the peracid concentration is stable for about 21 hours after the enzyme-catalyzed production of peracid is over. In another embodiment, the peracid concentration is stable for about 24 hours after the enzyme-catalyzed production of peracid is over. In one embodiment, the peracid concentration is stable for about 30 hours after the enzyme-catalyzed production of peracid is over. In one embodiment, the peracid concentration is stable for about 36 hours after the enzyme-catalyzed production of peracid is over. In one embodiment, the peracid concentration is stable for about 42 hours after the enzyme-catalyzed production of peracid is over. In another embodiment, the peracid concentration is stable for about 48 hours after the enzyme-catalyzed production of peracid is over. In one embodiment, the peracid concentration is stable for greater than 48 hours after the enzyme-catalyzed production of peracid is over.

The temperature of the reaction is chosen to control both the reaction rate and the stability of the enzyme catalyst activity. The temperature of the reaction may range from just above the freezing point of the reaction mixture (approximately 0° C.) to about 75° C., with a preferred range of reaction temperature of from about 5° C. to about 55° C.

In another aspect, the enzymatic perhydrolysis reaction mixture may contain an organic solvent that acts as a dispersant to enhance the rate of dissolution of the carboxylic acid ester in the reaction mixture. Such solvents include, but are not limited to, propylene glycol methyl ether, acetone, cyclohexanone, diethylene glycol butyl ether, tripropylene glycol methyl ether, diethylene glycol methyl ether, propylene glycol butyl ether, dipropylene glycol methyl ether, cyclohexanol, benzyl alcohol, isopropanol, ethanol, propylene glycol, and mixtures thereof.

In another aspect, the enzymatic perhydrolysis product may contain additional components that provide desirable functionality. These additional components include, but are not limited to buffers, detergent builders, thickening agents, emulsifiers, surfactants, wetting agents, corrosion inhibitors (e.g., benzotriazole), enzyme stabilizers, and peroxide stabilizers (e.g., metal ion chelating agents). Many of the additional components are well known in the detergent industry (see, for example, U.S. Pat. No. 5,932,532; hereby incorporated by reference). Examples of emulsifiers include, but are not limited to polyvinyl alcohol or polyvinylpyrrolidone. Examples of thickening agents include, but are not limited to LAPONITE® RD, corn starch, PVP, CARBOWAX®, CARBOPOL®, CABOSIL®, polysorbate 20, PVA, and lecithin. Examples of buffering systems include, but are not limited to sodium phosphate monobasic/sodium phosphate dibasic; sulfamic acid/triethanolamine; citric acid/triethanolamine; tartaric acid/triethanolamine; succinic acid/triethanolamine; and acetic acid/triethanolamine. Examples of surfactants include, but are not limited to a) non-ionic surfactants such as block copolymers of ethylene oxide or propylene oxide, ethoxylated or propoxylated linear and branched primary and secondary alcohols, and aliphatic phosphine oxides b) cationic surfactants such as quaternary ammonium compounds, particularly quaternary ammonium compounds having a C8-C20 alkyl group bound to a nitrogen atom additionally bound to three C1-C2 alkyl groups, c) anionic surfactants such as alkane carboxylic acids (e.g., C8-C20 fatty acids), alkyl phosphonates, alkane sulfonates (e.g., sodium dodecylsulphate "SDS") or linear or branched alkyl benzene sulfonates, alkene sulfonates and d) amphoteric and zwitterionic surfactants such as aminocarboxylic acids, aminodicarboxylic acids, alkybetaines, and mixtures thereof. Additional components may include fragrances, dyes, stabilizers of hydrogen peroxide (e.g., metal chelators such as 1-hydroxyethylidene-1,1-diphosphonic acid (DEQUEST® 2010, Solutia Inc., St. Louis, Mo. and ethylenediaminetetraacetic acid (EDTA)), TURPINAL® SL, DEQUEST® 0520, DEQUEST® 0531, stabilizers of enzyme activity (e.g., polyethyleneglycol (PEG)), and detergent builders.

In another aspect, the enzymatic perhydrolysis product may be pre-mixed to generate the desired concentration of peroxycarboxylic acid prior to contacting the surface or inanimate object to be disinfected.

In another aspect, the enzymatic perhydrolysis product is not pre-mixed to generate the desired concentration of peroxycarboxylic acid prior to contacting the surface or inanimate object to be disinfected, but instead, the components of the reaction mixture that generate the desired concentration of percarboxylic acid are contacted with the surface or inanimate object to be disinfected, generating the desired concentration of peroxycarboxylic acid. In some embodiments, the components of the reaction mixture combine or mix at the locus. In some embodiments, the reaction components are delivered or applied to the locus and subsequently mix or combine to generate the desired concentration of peroxycarboxylic acid.

In Situ Production of Peracids Using a Perhydrolase Catalyst

Cephalosporin C deacetylases (E.C. 3.1.1.41; systematic name cephalosporin C acetylhydrolases; CAHs) are enzymes having the ability to hydrolyze the acetyl ester bond on cephalosporins such as cephalosporin C, 7-aminocephalosporanic acid, and 7-(thiophene-2-acetamido)cephalosporanic acid (Abbott, B. and Fukuda, D., *Appl. Microbiol.* 30(3):413-419 (1975)). CAHs belong to a larger family of structurally related enzymes referred to as the carbohydrate esterase family seven (CE-7; see Coutinho, P. M., Henrissat, B. "Carbohydrate-active enzymes: an integrated database approach" in *Recent Advances in Carbohydrate Bioengineering*, H. J. Gilbert, G. Davies, B. Henrissat and B. Svensson eds., (1999) The Royal Society of Chemistry, Cambridge, pp. 3-12.)

The CE-7 family includes both CAHs and acetyl xylan esterases (AXEs; E.C. 3.1.1.72). CE-7 family members share a common structural motif and are quite unusual in that they typically exhibit ester hydrolysis activity for both acetylated xylooligosaccharides and cephalosporin C, suggesting that the CE-7 family represents a single class of proteins with a multifunctional deacetylase activity against a range of small substrates (Vincent et al., *J. Mol. Biol.*, 330:593-606 (2003)). Vincent et al. describes the structural similarity among the members of this family and defines a signature sequence motif characteristic of the CE-7 family.

Members of the CE-7 family are found in plants, fungi (e.g., *Cephalosporidium acremonium*), yeasts (e.g., *Rhodosporidium toruloides, Rhodotorula glutinis*), and bacteria such as *Thermoanaerobacterium* sp.; *Norcardia lactamdurans*, and various members of the genus *Bacillus* (Politino et al., *Appl. Environ. Microbiol.*, 63(12):4807-4811 (1997); Sakai et al., *J. Ferment. Bioeng.* 85:53-57 (1998); Lorenz, W. and Wiegel, J., *J. Bacteriol* 179:5436-5441 (1997); Cardoza et al., *Appl. Microbiol. Biotechnol.*, 54(3):406-412 (2000); Mitsushima et al., supra (1995), Abbott, B. and Fukuda, D., *Appl. Microbiol.* 30(3):413-419 (1975); Vincent et al., supra, Takami et al., *NAR*, 28(21):4317-4331 (2000); Rey et al., *Genome Biol.*, 5(10): article 77 (2004); Degrassi et al., *Microbiology.*, 146:1585-1591 (2000); U.S. Pat. No. 6,645,233. U.S. Pat. No. 5,281,525; U.S. Pat. No. 5,338,676; and WO 99/03984. A non-comprehensive list of CE-7 carbohydrate esterase family members having significant homology to SEQ ID NO: 2 are provided in Table 1.

TABLE 1

Example of CE-7 Enzymes Having Significant Homology to SEQ ID NO: 2.

| Source Organism (GENBANK® Accession No. of the CE-7 enzyme) | Nucleotide Sequence (SEQ ID NO:) | Amino Acid Sequence (SEQ ID NO:) | % Amino Acid Identity to SEQ ID NO: 2 | Reference |
|---|---|---|---|---|
| *B. subtilis* ATCC® 31954™ | 1 | 2 | 100 | *B. subtilis* SHS 0133 Mitsushima et al. supra (1995) |
| *B. subtilis* subsp. *subtilis* str. 168 (NP_388200) *B. subtilis* BE1010 | 3 | 4 | 98 | Kunst et al., supra. WO99/03984 Payne and Jackson, *J. Bacteriol.* 173: 2278-2282 (1991)) |
| *B. subtilis* ATCC® 6633™ (YP_077621.1) | 5 | 6 | 96 | U.S. Pat. No. 6,465,233 |
| *B. subtilis* ATCC® 29233™ | 29 | 30 | 96 | Abbott and Fukuda, supra |
| *B. licheniformis* ATCC® 14580™ (YP_077621.1) | 7 | 8 | 77 | Rey et al., supra |
| *B. pumilus* PS213 (CAB76451.2) | 9 | 10 | 76 | Degrassi et al., supra |
| *Clostridium thermocellum* ATCC® 27405™ (ZP_00504991) | 11 | 12 | 57 | Copeland et al. US Dept. of Energy Joint Genome Institute (JGI-PGF) Direct Submission GENBANK® ZP_00504991 |
| *Thermotoga neapolitana* (AAB70869.1) | 13 | 14 | 42 | See GENBANK® AAB70869.1 |
| *Thermotoga maritima* MSB8 (NP_227893.1) | 15 | 16 | 42 | Nelson et al., *Nature* 399 (6734): 323-329 (1999) |
| *Bacillus* sp. NRRL B-14911 (ZP_01168674) | 19 | 20 | 40 | Siefert et al. J. Craig Venter Institute. Direct Submission Under GENBANK® ZP_01168674 |
| *Thermoanaerobacterium* sp. (AAB68821.1) | 17 | 18 | 37 | Lorenz and Wiegel, supra |
| *Bacillus halodurans* C-125 (NP_244192) | 21 | 22 | 36 | Takami et al., supra |
| *Thermoanearobacterium saccharolyticum* (S41858) | — | 54 | 35 | Lee, Y. E. and Zeikus, J. G., *J Gen Microbiol.* (1993), 139 Pt 6: 1235-1243 |
| *Bacillus clausii* KSM-K16 (YP_175265) | 23 | 24 | 33 | Kobayashi et al., *Appl. Microbiol. Biotechnol.* 43 (3), 473-481 (1995) |
| *Thermotoga lettingae* (CP000812) | 55 | 57 | 37 | Copeland et al. US Dept. of Energy Joint Genome Institute Direct Submission GENBANK® CP000812 |

TABLE 1-continued

Example of CE-7 Enzymes Having Significant Homology to SEQ ID NO: 2.

| Source Organism (GENBANK® Accession No. of the CE-7 enzyme) | Nucleotide Sequence (SEQ ID NO:) | Amino Acid Sequence (SEQ ID NO:) | % Amino Acid Identity to SEQ ID NO: 2. | Reference |
|---|---|---|---|---|
| *Thermotoga Petrophila* (CP000702) | 57 | 58 | 41 | Copeland et al. US Dept. of Energy Joint Genome Institute Direct Submission GENBANK® CP000702 |
| *Thermotoga* sp. RQ2 RQ2(a) (CP000969) | 59 | 60 | 42 | Copeland et al. US Dept. of Energy Joint Genome Institute Direct Submission GENBANK® CP000969 |
| *Thermotoga* sp. RQ2 RQ2(b) (CP000969) | 61 | 63 | 42 | Copeland et al. US Dept. of Energy Joint Genome Institute Direct Submission GENBANK® CP000969 |

The present perhydrolases are all members of the CE-7 carbohydrate esterase family. As described by Vincent et al. (supra), members of the family share a common signature motif that is characteristic of this family. A CLUSTALW alignment of the present perhydrolases indicates that all of the members belong to the CE-7 carbohydrate esterase family. A comparison of the overall percent amino acid identity amount the present perhydrolases is provided in Table 2.

TABLE 2

Percent Amino Acid Identity Between Perhydrolases[1]

|    | 1   | 2   | 3   | 4   | 5   | 6   | 7   | 8   | 9   | 10  | 11  | 12  | 13  | 14  | 15  |
|----|-----|-----|-----|-----|-----|-----|-----|-----|-----|-----|-----|-----|-----|-----|-----|
| 1  | 100 |     |     |     |     |     |     |     |     |     |     |     |     |     |     |
| 2  | 99  | 100 |     |     |     |     |     |     |     |     |     |     |     |     |     |
| 3  | 99  | 99  | 100 |     |     |     |     |     |     |     |     |     |     |     |     |
| 4  | 96  | 96  | 97  | 100 |     |     |     |     |     |     |     |     |     |     |     |
| 5  | 77  | 76  | 77  | 76  | 100 |     |     |     |     |     |     |     |     |     |     |
| 6  | 76  | 76  | 76  | 76  | 68  | 100 |     |     |     |     |     |     |     |     |     |
| 7  | 57  | 57  | 57  | 56  | 56  | 56  | 100 |     |     |     |     |     |     |     |     |
| 8  | 42  | 43  | 43  | 43  | 43  | 42  | 41  | 100 |     |     |     |     |     |     |     |
| 9  | 42  | 43  | 42  | 43  | 43  | 42  | 42  | 72  | 100 |     |     |     |     |     |     |
| 10 | 42  | 43  | 43  | 43  | 44  | 42  | 43  | 71  | 91  | 100 |     |     |     |     |     |
| 11 | 41  | 43  | 43  | 43  | 45  | 42  | 43  | 71  | 97  | 91  | 100 |     |     |     |     |
| 12 | 41  | 42  | 42  | 42  | 43  | 41  | 42  | 71  | 98  | 91  | 97  | 100 |     |     |     |
| 13 | 37  | 37  | 37  | 36  | 39  | 38  | 38  | 64  | 65  | 67  | 66  | 65  | 100 |     |     |
| 14 | 34  | 36  | 35  | 36  | 35  | 36  | 33  | 36  | 32  | 34  | 34  | 33  | 36  | 100 |     |
| 15 | 33  | 34  | 33  | 33  | 32  | 34  | 32  | 30  | 30  | 32  | 31  | 31  | 32  | 34  | 100 |

[1] = Percent identity determined using blast2seq algorithm using BLOSUM62, gap open = 11, gap extension = 1, x_drop = 0, expect = 10, and wordsize = 3. Tatiana A. Tatusova, Thomas L. Madden (1999), "Blast 2 sequences - a new tool for comparing protein and nucleotide sequences", *FEMS Microbiol Lett.* 174: 247-250

1. *B. subtilis* ATCC® 31954™
2. *B. subtilis* BE1010
3. *B. subtilis* ATCC® 29233™
4. *B. subtilis* ATCC® 6633™
5. *B. licheniformis* 14580
6. *B. pumilus* PS213
7. *C. thermocellum* ATCC® 27405™
8. *Thermotoga* sp. RQ2(b)
9. *Thermotoga* sp. RQ2(a)
10. *T. neapolitana*
11. *T. maritima*
12. *T. petrophila*
13. *T. lettingae*
14. *T. saccharolyticum*
15. *B. clausii*

Although variation is observed in terms of overall percent amino acid identity (i.e. the *Clostridium thermocellum* ATCC® 27405™ perhydrolase; SEQ ID NO: 12 shares only 57% amino acid identity with the *Bacillus subtilis* ATCC® 31954™ perhydrolase; SEQ ID NO: 2, while the *Bacillus clausii* perhydrolase (SEQ ID NO: 24) shares only 33% identity with SEQ ID NO: 2), each of the present perhydrolase enzymes share the CE-7 signature motif. Accordingly, the perhydrolase catalyst of the present invention is an enzyme structurally classified as belonging to the CE-7 carbohydrate esterase family. Each of the present perhydrolase enzymes comprises the CE-7 signature (diagnostic) motif.

Vincent et al. (supra) analyzed the structure CE-7 esterases and identified several highly conserved motifs that are diagnostic for the family. These highly conserved motifs include the Arg118-Gly119-Gln120 (RGQ), Gly179-Xaa180-Ser181-Gln182-Gly183 (GXSQG), and His298-Glu299 (HE). In addition, there is a highly conserved Lys267-Xaa268-Asp269 (LXD) motif that may be used to further characterize the signature motif. All sequence numbering is relative to the numbering of a reference sequence (*B. subtilis* ATCC® 31954™ perhydrolase; SEQ ID NO: 2).

In one embodiment, suitable perhydrolytic enzymes can be identified by the presence of the CE-7 signature motif (Vincent et al., supra). In a preferred embodiment, perhydrolases comprising the CE-7 signature motif are identified using a CLUSTALW alignment against the *Bacillus subtilis* ATCC® 31954™ perhydrolase (SEQ ID NO: 2; i.e. the reference sequence used for relative amino acid position numbering). As per the amino acid residue numbering of SEQ ID NO: 2, the CE-7 signature motif comprises 3 conserved motifs defined as:

a) Arg118-Gly119-Gln120;
b) Gly179-Xaa180-Ser181-Gln182-Gly183; and
c) His298-Glu299.

Typically, the Xaa at amino acid residue position 180 is glycine, alanine, proline, tryptophan, or threonine. Two of the three amino acid residues belonging to the catalytic triad are in bold. In one embodiment, the Xaa at amino acid residue position 180 is selected from the group consisting of glycine, alanine, proline, tryptophan, and threonine.

Further analysis of the conserved motifs within the CE-7 carbohydrate esterase family indicates the presence of an additional conserved motif (LXD at amino acid positions 267-269 of SEQ ID NO: 2) that may be to further define a perhydrolase belonging to the CE-7 carbohydrate esterase family (FIGS. 1a-c). In a further embodiment, the signature motif defined above includes a forth conserved motif defined as:

Leu267-Xaa268-Asp269.

The Xaa at amino acid residue position 268 is typically isoleucine, valine, or methionine. The forth motif includes the aspartic acid residue (bold) that is the third member of the catalytic triad (Ser181-Asp269-His298).

Any number of well-known global alignment algorithms (i.e. sequence analysis software) may be used to align two or more amino acid sequences (representing enzymes having perhydrolase activity) to determine the existence of the present signature motif (for example, CLUSTALW or Needleman and Wunsch (*J. Mol. Biol.*, 48:443-453 (1970)). The aligned sequence(s) is compared to the reference sequence (SEQ ID NO: 2). In one embodiment, a CLUSTAL alignment (CLUSTALW) using a reference amino acid sequence (as used herein the CAH sequence (SEQ ID NO: 2) from the *Bacillus subtilis* ATCC® 31954™) is used to identify perhydrolases belonging to the CE-7 esterase family. The relative numbering of the conserved amino acid residues is based on the residue numbering of the reference amino acid sequence to account for small insertions or deletions (5 amino acids or less) within the aligned sequence.

A comparison of the overall percent identity among perhydrolases exemplified herein indicates that enzymes having as little as 33% identity to SEQ ID NO: 2 (while retaining the signature motif) exhibit significant perhydrolase activity and are structurally classified as CE-7 carbohydrate esterases. In one embodiment, the present perhydrolases include enzymes comprising the present signature motif and at least 30%, preferably at least 33%, more preferably at least 40%, even more preferably at least 42%, even more preferably at least 50%, even more preferably at least 60%, even more preferably at least 70%, even more preferably at least 80%, even more preferably at least 90%, and most preferably at least 90%, 91%, 92%, 93%, 94%, 95%, 96%, 97%, 98%, or 99% amino acid identity to SEQ ID NO: 2.

All of the present perhydrolases are comprised of the above signature motif as shown in Table 3.

TABLE 3

Conserved motifs found within the present enzymes having perhydrolase activity.

| Perhydrolase Sequence | RGQ motif[a] (Residue #s) | GXSQG motif[a] (Residue #s) | LXD motif[b] Residue #s) | HE motif[a] (Residue #s) |
|---|---|---|---|---|
| SEQ ID NO: 2 | 118-120 | 179-183 | 267-269 | 298-299 |
| SEQ ID NO: 4 | 118-120 | 179-183 | 267-269 | 298-299 |
| SEQ ID NO: 6 | 118-120 | 179-183 | 267-269 | 298-299 |
| SEQ ID NO: 8 | 119-121 | 180-184 | 268-270 | 299-300 |
| SEQ ID NO: 10 | 118-120 | 179-183 | 267-269 | 298-299 |
| SEQ ID NO: 12 | 119-121 | 181-185 | 269-271 | 300-301 |
| SEQ ID NO: 14 | 118-120 | 186-190 | 272-274 | 303-304 |
| SEQ ID NO: 16 | 118-120 | 186-190 | 272-274 | 303-304 |
| SEQ ID NO: 18 | 117-119 | 180-184 | 270-272 | 301-302 |
| SEQ ID NO: 20 | 133-135 | 193-197 | 282-284 | 313-314 |
| SEQ ID NO: 22 | 118-120 | 181-185 | 171-173 | 302-303 |
| SEQ ID NO: 24 | 117-119 | 180-184 | 270-272 | 301-302 |
| SEQ ID NO: 30 | 118-120 | 179-183 | 267-269 | 298-299 |
| SEQ ID NO: 54 | 117-119 | 180-184 | 270-272 | 301-302 |
| SEQ ID NO: 56 | 118-120 | 186-190 | 272-274 | 303-304 |
| SEQ ID NO: 58 | 118-120 | 186-190 | 272-274 | 303-304 |
| SEQ ID NO. 60 | 118-120 | 186-190 | 272-274 | 303-304 |
| SEQ ID NO. 62 | 119-121 | 187-191 | 273-275 | 304-305 |

[a] = Conserved motifs defined by Vincent et al., supra used to define the signature motif.
[b] = an additional motif identified herein useful in further defining the signature motif defined by Vincent et al., supra.

Alternatively, a contiguous signature motif (SEQ ID NO: 53) comprising the 4 conserved motifs (RGQ, GXSQG, LXD, and HE; Amino acids residues 118-299 of SEQ ID NO: 2) may also be used as a contiguous signature motif to identify CE-7 carbohydrate esterases. As such, suitable enzymes expected to have perhydrolase activity may also be identified as having at least 30% amino acid identify, preferably at least 36%, more preferably at least 40%, even more preferably at least 50%, yet more preferably at least 60%, yet even more preferably at least 70%, yet even more preferably at least 80%, yet even more preferably at least 90%, 91%, 92%, 93%, 94%, 95%, 96%, 97%, 98%, or 99% amino acid identity to SEQ ID NO: 53 (the 4 conserved motifs found in CE-7 carbohydrate esterases are underlined).

(SEQ ID NO: 53)
RGQQSSEDTSISLHGHALGWMTKGILDKDTYYYRGVYLDAVRALEVISS

FDEVDETRIGVTGGSQGGGLTIAAAALSDIPKAAVADYPYLSNFERAID

-continued

VALEQPYLEINSFFRRNGSPETEVQAMKTLSYFDIMNLADRVKVPVLMS

IGL<u>ID</u>KVTPPSTVFAAYNHLETEKELKVYRYFG<u>HE</u>.

A comparison using the contiguous signature sequence against the present CE-7 esterases having perhydrolase activity is provided in Table 4. BLASTP using default parameters was used.

TABLE 4

Percent Amino Acid Identity of Various CE-7 Carbohydrate Esterases having Perhydrolysis Activity Versus the Contiguous Signature Sequence (SEQ ID NO: 53).

| Perhydrolase Sequence | % Identity using BLASTP | E-score (expected) |
| --- | --- | --- |
| SEQ ID NO: 2 | 100 | 3e-92 |
| SEQ ID NO: 4 | 98 | 6e-91 |
| SEQ ID NO: 6 | 98 | 4e-98 |
| SEQ ID NO: 8 | 78 | 1e-78 |
| SEQ ID NO: 10 | 80 | 3e-76 |
| SEQ ID NO: 12 | 63 | 2e-56 |
| SEQ ID NO: 14 | 51 | 1e-41 |
| SEQ ID NO: 16 | 50 | 6e-35 |
| SEQ ID NO: 24 | 36 | 7e-21 |
| SEQ ID NO: 30 | 99 | 2e-90 |
| SEQ ID NO: 54 | 40 | 2e-26 |
| SEQ ID NO: 56 | 40 | 3e-30 |
| SEQ ID NO: 58 | 46 | 6e-35 |
| SEQ ID NO. 61 | 46 | 6e-35 |
| SEQ ID NO. 62 | 48 | 9e-36 |

Alternatively, the percent amino acid identity to the complete length of one or more of the present perhydrolases may also be used. Accordingly, suitable enzymes having an amino acid sequence having at least 30%, preferably at least 33%, preferably at least 40%, preferably at least 40%, more preferably at least 50%, more preferably at least 60%, more preferably at least 70%, even more preferably at least 80%, yet even more preferably at least 90%, and most preferably at least 90%, 91%, 92%, 93%, 94%, 95%, 96%, 97%, 98%, or 99% amino acid identity to SEQ ID NO: 2. In a further embodiment, suitable perhydrolase catalysts comprise an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 30, SEQ ID NO: 54, SEQ ID NO: 56, SEQ ID NO: 58, SEQ ID NO: 60, SEQ ID NO: 62. In preferred embodiments, suitable enzymes having perhydrolase activity having at least 90%, at least 91%, at least 92%, at least 93%, at least 94%, at least 95%, at least 96%, at least 97%, at least 98%, or at least 99% amino acid identity to SEQ ID NO: 2 or to SEQ ID NO: 10 or to SEQ ID NO: 14 or to SEQ ID NO: 16 may be used.

Suitable perhydrolase enzymes may also include enzymes having one or more deletions, substitutions, and/or insertions to one of the present perhydrolase enzymes (e.g. SEQ ID NOs. 2, 10, 14, and 16). As shown in Table 2, CE-7 carbohydrates esterases having perhydrolysis activity share as little as 32% overall amino acid identity. Based on the data provided in the present examples, additional enzymes having perhydrolase activity belonging to the CE-7 carbohydrate esterase family may have even lower percent identity, so long as the enzyme retains the conserved signature motif. As such, the numbers of deletions, substitutions, and/or insertions may vary so long as the conserved signature motifs (see Table 3) are found in their relative positions within the enzyme.

An enzyme catalyst comprising a variant enzyme having an amino acid sequence derived from one or more of the present sequences provided herein may also be used in the present processes. U.S. Provisional Patent Application No. 61/102,520 to DiCosimo et al. (incorporated herein by reference) describes enzyme catalysts having improved perhydrolysis activity. More specifically, DiCosimo et al. teaches how certain amino acid substitutions (alanine, valine, serine or threonine) to a key cysteine residue found within several *Thermotoga* acetyl xylan esterases increases perhydrolysis activity of the variant enzyme when compared to the wild-type acetyl xylan esterase. Because of the high homology between acetyl xylan esterases across the *Thermotoga* genus, it is expected that a substitution to the cysteine residue with an alanine, valine, serine, or threonine in any *Thermotoga* genus will produce similar results.

In one embodiment, the present processes may use variant *Thermotoga*-derived enzymes having at least 95% sequence identity (or, in various embodiments, 96%, 97%, 98%, or 99% sequence identity), based on the CLUSTAL method (such as CLUSTALW) of alignment with pairwise alignment default parameters of KTUPLE=1, GAP PENALTY=3, WINDOW=5 and DIAGONALS SAVED=5, when compared to SEQ ID NOs: 69, 70, 71, 72, or 73, provided that a substitution to amino acid 277 of SEQ ID NOs: 69, 70, 71, 72, or 73 is selected from the group consisting of serine, threonine, valine, and alanine.

In a more specific embodiment, the present processes may use a variant *Thermotoga* enzyme comprising an amino acid sequence selected from the group consisting of SEQ ID NOs: 69, 70, 71, 72, and 73 provided the amino acid residue 277 is selected from the group consisting of serine, threonine, valine, and alanine.

In a further specific embodiment, the present processes may use a variant *Thermotoga neapolitana* enzyme comprising an amino acid sequence SEQ ID NO: 69 wherein amino acid residue 277 is substituted with an amino acid selected from the group consisting of serine, threonine, valine, and alanine.

In a further specific embodiment, the present processes may use a variant *Thermotoga maritima* enzyme comprising an amino acid sequence SEQ ID NO: 70 wherein amino acid residue 277 is substituted with an amino acid selected from the group consisting of serine, threonine, valine, and alanine.

Additionally, it is well within one of skill in the art to identity suitable enzymes according to the structural similarity found within the corresponding nucleic acid sequence. Hybridization techniques can be used to identity similar gene sequences. Accordingly, suitable perhydrolase catalysts useful in the present processes comprise an amino acid sequence encoded by a nucleic acid molecule that hybridizes under stringent conditions to a nucleic acid molecule having a nucleic acid sequence selected from the group consisting of SEQ ID NO: 1; SEQ ID NO: 3; SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 29, SEQ ID NO: 55, SEQ ID NO: 57, SEQ ID NO: 59, and SEQ ID NO: 61.

In another embodiment, the perhydrolase catalyst comprises an enzyme having an amino acid sequence encoded by a nucleic acid molecule that hybridizes under stringent conditions to a nucleic acid sequence selected from the group consisting of SEQ ID NO: 1, SEQ ID NO: 9, SEQ ID NO: 13, and SEQ ID NO: 15.

The present method produces industrially useful, efficacious concentrations of peracids in situ under aqueous reaction conditions using the perhydrolase activity of an enzyme belonging to the CE-7 family of carbohydrate esterases. In one embodiment, the enzyme having perhydrolase activity is also classified structurally and functionally as a cephalosporin C deacetylase (CAH). In another embodiment, the enzyme having perhydrolase activity is classified structurally and functionally as an acetyl xylan esterase (AXE).

The peracids produced are quite reactive and may decrease in concentration over extended periods of time, depending on variables that include, but are not limited to, temperature and pH. As such, it may be desirable to keep the various reaction components separated, especially for liquid formulations. In one aspect, the hydrogen peroxide source is separate from either the substrate or the perhydrolase catalyst, preferably from both. This can be accomplished using a variety of techniques including, but not limited to, the use of multicompartment chambered dispensers (U.S. Pat. No. 4,585,150) and at the time of use physically combining the perhydrolase catalyst with an inorganic peroxide and the present substrates to initiate the aqueous enzymatic perhydrolysis reaction. The perhydrolase catalyst may optionally be immobilized within the body of reaction chamber or separated (e.g., filtered, etc.) from the reaction product comprising the peracid prior to contacting the surface and/or object targeted for treatment. The perhydrolase catalyst may be in a liquid matrix or in a solid form (i.e., powdered, tablet) or embedded within a solid matrix that is subsequently mixed with the substrates to initiate the enzymatic perhydrolysis reaction. In a further aspect, the perhydrolase catalyst may be contained within a dissolvable or porous pouch that may be added to the aqueous substrate matrix to initiate enzymatic perhydrolysis. In an additional further aspect, a powder comprising the enzyme catalyst is suspended in the substrate (e.g., triacetin), and at time of use is mixed with a source of peroxygen in water.

HPLC Assay Method for Determining the Concentration of Peracid and Hydrogen Peroxide.

A variety of analytical methods can be used in the present method to analyze the reactants and products including, but not limited to, titration, high performance liquid chromatography (HPLC), gas chromatography (GC), mass spectroscopy (MS), capillary electrophoresis (CE), the analytical procedure described by U. Karst et al., (*Anal. Chem.*, 69(17): 3623-3627 (1997)), and the 2,2'-azino-bis(3-ethylbenzothazoline)-6-sulfonate (ABTS) assay (S. Minning, et al., *Analytica Chimica Acta* 378:293-298 (1999) and WO 2004/058961 A1) as described in the present examples.

Determination of Minimum Biocidal Concentration of Peracids

The method described by J. Gabrielson, et al. (*J. Microbiol. Methods* 50: 63-73 (2002)) can be employed for determination of the Minimum Biocidal Concentration (MBC) of peracids, or of hydrogen peroxide and enzyme substrates. The assay method is based on XTT reduction inhibition, where XTT ((2,3-bis[2-methoxy-4-nitro-5-sulfophenyl]-5-[(phenylamino)carbonyl]-2H-tetrazolium, inner salt, monosodium salt) is a redox dye that indicates microbial respiratory activity by a change in optical density (OD) measured at 490 nm or 450 nm. However, there are a variety of other methods available for testing the activity of disinfectants and antiseptics including, but not limited to, viable plate counts, direct microscopic counts, dry weight, turbidity measurements, absorbance, and bioluminescence (see, for example Brock, Semour S., *Disinfection, Sterilization, and Preservation*, 5$^{th}$ edition, Lippincott Williams & Wilkins, Philadelphia, Pa., USA; 2001).

Uses of Enzymatically Prepared Peracid Compositions

The enzyme catalyst-generated peracid produced according to the present methods can be used in a variety of hard surface/inanimate object applications for reduction of concentrations of microbial, fungal, prion-related, and viral contamination, such as decontamination of medical instruments (e.g., endoscopes), textiles (e.g., garments, carpets), food preparation surfaces, food storage and food-packaging equipment, materials used for the packaging of food products, chicken hatcheries and grow-out facilities, animal enclosures, and spent process waters that have microbial and/or virucidal activity. The enzyme-generated peracids may be used in formulations designed to inactivate prions (e.g. certain proteases) to additionally provide biocidal activity. In a preferred aspect, the present peracid compositions are particularly useful as a disinfecting agent for non-autoclavable medical instruments and food packaging equipment. As the peracid-containing formulation may be prepared using GRAS or food-grade components (enzyme, enzyme substrate, hydrogen peroxide, and buffer), the enzyme-generated peracid may also be used for decontamination of animal carcasses, meat, fruits and vegetables, or for decontamination of prepared foods. The enzyme-generated peracid may be incorporated into a product whose final form is a powder, liquid, gel, film, solid or aerosol. The enzyme-generated peracid may be diluted to a concentration that still provides an efficacious decontamination.

The compositions comprising an efficacious concentration of peracid can be used to disinfect surfaces and/or objects contaminated (or suspected of being contaminated) with viable pathogenic microbial contaminants by contacting the surface or object with the products produced by the present processes. As used herein, "contacting" refers to placing a disinfecting composition comprising an effective concentration of peracid in contact with the surface or inanimate object suspected of contamination with a disease-causing entity for a period of time sufficient to clean and disinfect. Contacting includes spraying, treating, immersing, flushing, pouring on or in, mixing, combining, painting, coating, applying, affixing to and otherwise communicating a peracid solution or composition comprising an efficacious concentration of peracid, or a solution or composition that forms an efficacious concentration of peracid, with the surface or inanimate object suspected of being contaminated with a concentration of a microbial population. The disinfectant compositions may be combined with a cleaning composition to provide both cleaning and disinfection. Alternatively, a cleaning agent (e.g., a surfactant or detergent) may be incorporated into the formulation to provide both cleaning and disinfection in a single composition.

The compositions comprising an efficacious concentration of peracid can also contain at least one additional antimicrobial agent, combinations of prion-degrading proteases, a virucide, a sporicide, or a biocide. Combinations of these agents with the peracid produced by the claimed processes can provide for increased and/or synergistic effects when used to clean and disinfect surfaces and/or objects contaminated (or suspected of being contaminated) with pathogenic microorganisms, spores, viruses, fungi, and/or prions. Suitable antimicrobial agents include carboxylic esters (e.g., p-hydroxy alkyl benzoates and alkyl cinnamates), sulfonic acids (e.g., dodecylbenzene sulfonic acid), iodo-compounds or active halogen compounds (e.g., elemental halogens, halogen oxides (e.g., NaOCl, HOCl, HOBr, $ClO_2$), iodine, interhalides (e.g., iodine monochloride, iodine dichloride, iodine trichloride, iodine tetrachloride, bromine chloride, iodine monobromide, or iodine dibromide), polyhalides, hypochlorite salts, hypochlorous acid, hypobromite salts, hypobromous acid, chloro- and bromo-hydantoins, chlorine dioxide, and sodium chlorite), organic peroxides including benzoyl peroxide, alkyl benzoyl peroxides, ozone, singlet oxygen generators, and mixtures thereof, phenolic derivatives (e.g., o-phenyl phenol, o-benzyl-p-chlorophenol, tert-amyl phenol and $C_1$-$C_6$ alkyl hydroxy benzoates), quaternary ammonium compounds (e.g., alkyldimethylbenzyl ammonium chloride, dialkyldimethyl ammonium chloride and mixtures thereof), and mixtures of such antimicrobial agents, in an amount sufficient to provide the desired degree of microbial protection. Effective amounts of antimicrobial agents include about 0.001 wt % to about 60 wt % antimicrobial agent, about 0.01 wt % to about 15 wt % antimicrobial agent, or about 0.08 wt % to about 2.5 wt % antimicrobial agent.

In one aspect, the peracids formed by the present process can be used to reduce the concentration of viable microbial contaminants (e.g. a viable microbial population) when applied on and/or at a locus. As used herein, a "locus" comprises part or all of a target surface suitable for disinfecting or bleaching. Target surfaces include all surfaces that can potentially be contaminated with microorganisms, viruses, spores, fungi, prions or combinations thereof. Non-limiting examples include equipment surfaces found in the food or beverage industry (such as tanks, conveyors, floors, drains, coolers, freezers, equipment surfaces, walls, valves, belts, pipes, drains, joints, crevasses, combinations thereof, and the like); building surfaces (such as walls, floors and windows); non-food-industry related pipes and drains, including water treatment facilities, pools and spas, and fermentation tanks; hospital or veterinary surfaces (such as walls, floors, beds, equipment, (such as endoscopes) clothing worn in hospital/veterinary or other healthcare settings, including clothing, scrubs, shoes, and other hospital or veterinary surfaces); restaurant surfaces; bathroom surfaces; toilets; clothes and shoes; surfaces of barns or stables for livestock, such as poultry, cattle, dairy cows, goats, horses and pigs; hatcheries for poultry or for shrimp; and pharmaceutical or biopharmaceutical surfaces (e.g., pharmaceutical or biopharmaceutical manufacturing equipment, pharmaceutical or biopharmaceutical ingredients, pharmaceutical or biopharmaceutical excipients). Additional hard surfaces also include food products, such as beef, poultry, pork, vegetables, fruits, seafood, combinations thereof, and the like. The locus can also include water absorbent materials such as infected linens or other textiles. The locus also includes harvested plants or plant products including seeds, corms, tubers, fruit, and vegetables, growing plants, and especially crop growing plants, including cereals, leaf vegetables and salad crops, root vegetables, legumes, berried fruits, citrus fruits and hard fruits.

Non-limiting examples of hard surface materials are metals (e.g., steel, stainless steel, chrome, titanium, iron, copper, brass, aluminum, and alloys thereof), minerals (e.g., concrete), polymers and plastics (e.g., polyolefins, such as polyethylene, polypropylene, polystyrene, poly(meth)acrylate, polyacrylonitrile, polybutadiene, poly(acrylonitrile, butadiene, styrene), poly(acrylonitrile, butadiene), acrylonitrile butadiene; polyesters such as polyethylene terephthalate; and polyamides such as nylon). Additional surfaces include brick, tile, ceramic, porcelain, wood, vinyl, linoleum, and carpet.

Peracids have also been reported to be useful in preparing bleaching compositions for laundry detergent applications (U.S. Pat. No. 3,974,082; U.S. Pat. No. 5,296,161; and U.S. Pat. No. 5,364,554). Some bleaching applications may require a controlled level of bleaching activity for optimal performance. In an additional aspect, the peracids formed by the present process can be used for bleaching of laundry or textiles, where similar limitations to the concentration of peracid generated for bleaching are also desirable.

Recombinant Microbial Expression

The genes and gene products of the instant sequences may be produced in heterologous host cells, particularly in the cells of microbial hosts. Preferred heterologous host cells for expression of the instant genes and nucleic acid molecules are microbial hosts that can be found within the fungal or bacterial families and which grow over a wide range of temperature, pH values, and solvent tolerances. For example, it is contemplated that any of bacteria, yeast, and filamentous fungi may suitably host the expression of the present nucleic acid molecules. The perhydrolase may be expressed intracellularly, extracellularly, or a combination of both intracellularly and extracellularly, where extracellular expression renders recovery of the desired protein from a fermentation product more facile than methods for recovery of protein produced by intracellular expression. Transcription, translation and the protein biosynthetic apparatus remain invariant relative to the cellular feedstock used to generate cellular biomass; functional genes will be expressed regardless. Examples of host strains include, but are not limited to bacterial, fungal or yeast species such as *Aspergillus, Trichoderma, Saccharomyces, Pichia, Phaffia, Candida, Hansenula, Yarrowia, Salmonella, Bacillus, Acinetobacter, Zymomonas, Agrobacterium, Dythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. In one embodiment, bacterial host strains include *Escherichia, Bacillus*, and *Pseudomonas*. In a preferred embodiment, the bacterial host cell is *Escherichia coli*.

Large-scale microbial growth and functional gene expression may use a wide range of simple or complex carbohydrates, organic acids and alcohols or saturated hydrocarbons, such as methane or carbon dioxide in the case of photosynthetic or chemoautotrophic hosts, the form and amount of nitrogen, phosphorous, sulfur, oxygen, carbon or any trace micronutrient including small inorganic ions. The regulation of growth rate may be affected by the addition, or not, of specific regulatory molecules to the culture and which are not typically considered nutrient or energy sources.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell and/or native to the production host, although such control regions need not be so derived.

Initiation control regions or promoters, which are useful to drive expression of the present cephalosporin C deacetylase coding region in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1

(useful for expression in *Pichia*); and lac, ara, tet, trp, lP$_L$, lP$_R$, T7, tac, and trc (useful for expression in *Escherichia coli*) as well as the amy, apr, npr promoters and various phage promoters useful for expression in *Bacillus*.

Termination control regions may also be derived from various genes native to the preferred host cell. In one embodiment, the inclusion of a termination control region is optional. In another embodiment, the chimeric gene includes a termination control region derived the preferred host cell.

Industrial Production

A variety of culture methodologies may be applied to produce the present perhydrolase catalysts. For example, large-scale production of a specific gene product overexpressed from a recombinant microbial host may be produced by both batch and continuous culture methodologies.

A classical batch culturing method is a closed system where the composition of the media is set at the beginning of the culture and not subject to artificial alterations during the culturing process. Thus, at the beginning of the culturing process, the media is inoculated with the desired organism or organisms and growth or metabolic activity may occur without adding anything further to the system. Typically, however, a "batch" culture is batch with respect to the addition of carbon source and attempts are often made to control factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the fed-batch system. Fed-batch culture processes are also suitable in the present invention and comprise a typical batch system except that the substrate is added in increments as the culture progresses. Fed-batch systems are useful when catabolite repression is apt to inhibit the metabolism of the cells and where it is desirable to have limited amounts of substrate in the media. Measurement of the actual substrate concentration in fed-batch systems is difficult and is estimated on the basis of the changes of measurable factors such as pH, dissolved oxygen and the partial pressure of waste gases such as $CO_2$. Batch and fed-batch culturing methods are common and well known in the art and examples may be found in Thomas D. Brock in *Biotechnology: A Textbook of Industrial Microbiology*, Second Edition, Sinauer Associates, Inc., Sunderland, Mass. (1989) and Deshpande, Mukund V., *Appl. Biochem. Biotechnol.*, 36:227 (1992).

Commercial production of the desired perhydrolase catalysts may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include but are not limited to monosaccharides such as glucose and fructose, disaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally, the carbon substrate may also be one-carbon substrates such as carbon dioxide, methane or methanol (for example, when the host cell is a methylotrophic microorganism). Similarly, various species of *Candida* will metabolize alanine or oleic acid (Sutter et al., *Arch. Microbiol.*, 153:485-489 (1990)). Hence, it is contemplated that the source of carbon utilized in the present invention may encompass a wide variety of carbon-containing substrates and will only be limited by the choice of organism.

Recovery of the desired perhydrolase catalysts from a batch or fed batch fermentation, or continuous culture, may be accomplished by any of the methods that are known to those skilled in the art. For example, when the perhydrolase catalyst is produced intracellularly, the cell paste is separated from the culture medium by centrifugation or membrane filtration, optionally washed with water or an aqueous buffer at a desired pH, then a suspension of the cell paste in an aqueous buffer at a desired pH is homogenized to produce a cell extract containing the desired perhydrolase catalyst. The cell extract may optionally be filtered through an appropriate filter aid such as celite or silica to remove cell debris prior to a heat-treatment step to precipitate undesired protein from the perhydrolase catalyst solution. The solution containing the desired perhydrolase catalyst may then be separated from the precipitated cell debris and protein by membrane filtration or centrifugation, and the resulting partially-purified perhydrolase catalyst solution concentrated by additional membrane filtration, then optionally mixed with an appropriate carrier (for example, maltodextrin, phosphate buffer, citrate buffer, or mixtures thereof) and spray-dried to produce a solid powder comprising the desired perhydrolase catalyst.

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope be limited to the specific values recited when defining a range.

General Methods

The following examples are provided to demonstrate preferred aspects of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All reagents and materials were obtained from DIFCO Laboratories (Detroit, Mich.), GIBCO/BRL (Gaithersburg, Md.), TCI America (Portland, Oreg.), Roche Diagnostics Corporation (Indianapolis, Ind.) or Sigma/Aldrich Chemical Company (St. Louis, Mo.), unless otherwise specified.

The following abbreviations in the specification correspond to units of measure, techniques, properties, or compounds as follows: "sec" or "s" means second(s), "min" means minute(s), "h" or "hr" means hour(s), "4" means microliter(s), "mL" means milliliter(s), "L" means liter(s), "mM" means millimolar, "M" means molar, "mmol" means millimole(s), "ppm" means part(s) per million, "wt" means weight, "wt %" means weight percent, "g" means gram(s), "µg" means microgram(s), "ng" means nanogram(s), "g" means gravity, "HPLC" means high performance liquid chromatography, "dd H₂O" means distilled and deionized water, "dcw" means dry cell weight, "ATCC" or "ATCC®" means the American Type Culture Collection (Manassas, Va.), "U" means unit(s) of perhydrolase activity, "rpm" means revolution(s) per minute, and "EDTA" means ethylenediaminetetraacetic acid.

Example 1

Construction of a KatG Catalase Disrupted E. coli Strain

The kanamycin resistance gene (kan; SEQ ID NO: 35) was amplified from the plasmid pKD13 (SEQ ID NO: 36) by PCR (0.5 min at 94° C., 0.5 min at 55° C., 1 min at 70° C., 30 cycles) using primers identified as SEQ ID NO: 37 and SEQ ID NO: 38 to generate the PCR product identified as SEQ ID NO: 39. The katG nucleic acid sequence is provided as SEQ ID NO: 40 and the corresponding amino acid sequence is SEQ ID NO: 41. E. coli MG1655 (ATCC® 47076™) was transformed with the temperature-sensitive plasmid pKD46 (SEQ ID NO: 42), which contains the λ-Red recombinase genes (Datsenko and Wanner, 2000, PNAS USA 97:6640-6645), and selected on LB-amp plates for 24 h at 30° C. MG1655/pKD46 was transformed with 50-500 ng of the PCR product by electroporation (BioRad Gene Pulser, 0.2 cm cuvette, 2.5 kV, 200 W, 25 uF), and selected on LB-kan plates for 24 h at 37° C. Several colonies were streaked onto LB-kan plates and incubated overnight at 42° C. to cure the pKD46 plasmid. Colonies were checked to confirm a phenotype of kanR/ampS. Genomic DNA was isolated from several colonies using the PUREGENE® DNA purification system, and checked by PCR to confirm disruption of the katG gene using primers identified as SEQ ID NO: 43 and SEQ ID NO: 44. Several katG-disrupted strains were transformed with the temperature-sensitive plasmid pCP20 (SEQ ID NO: 45), which contains the FLP recombinase, used to excise the kan gene, and selected on LB-amp plates for 24 h at 37° C. Several colonies were streaked onto LB plates and incubated overnight at 42° C. to cure the pCP20 plasmid. Two colonies were checked to confirm a phenotype of kanS/ampS, and called MG1655 KatG1 and MG1655 KatG2.

Example 2

Construction of a KatE Catalase Disrupted E. coli Strain

The kanamycin resistance gene (SEQ ID NO: 35) was amplified from the plasmid pKD13 (SEQ ID NO: 36) by PCR (0.5 min at 94° C., 0.5 min at 55° C., 1 min at 70° C., 30 cycles) using primers identified as SEQ ID NO: 46 and SEQ ID NO: 47 to generate the PCR product identified as SEQ ID NO: 48. The katE nucleic acid sequence is provided as SEQ ID NO: 49 and the corresponding amino acid sequence is SEQ ID NO: 50. E. coli MG1655 (ATCC® 47076™) was transformed with the temperature-sensitive plasmid pKD46 (SEQ ID NO: 42), which contains the λ-Red recombinase genes, and selected on LB-amp plates for 24 h at 30° C. MG1655/pKD46 was transformed with 50-500 ng of the PCR product by electroporation (BioRad Gene Pulser, 0.2 cm cuvette, 2.5 kV, 200 W, 25 uF), and selected on LB-kan plates for 24 h at 37° C. Several colonies were streaked onto LB-kan plates and incubated overnight at 42° C. to cure the pKD46 plasmid. Colonies were checked to confirm a phenotype of kanR/ampS. Genomic DNA was isolated from several colonies using the PUREGENE DNA purification system, and checked by PCR to confirm disruption of the katE gene using primers identified as SEQ ID NO: 51 and SEQ ID NO: 52. Several katE-disrupted strains were transformed with the temperature-sensitive plasmid pCP20 (SEQ ID NO: 45), which contains the FLP recombinase, used to excise the kan gene, and selected on LB-amp plates for 24 h at 37° C. Several colonies were streaked onto LB plates and incubated, overnight at 42° C. to cure the pCP20 plasmid. Two colonies were checked to confirm a phenotype of kanS/ampS, and called MG1655 KatE1 and MG1655 KatE2

Example 3

Construction of a KatG Catalase and KatE Catalase Disrupted E. coli Strain (KLP18)

The kanamycin resistance gene (SEQ ID NO: 35) was amplified from the plasmid pkD13 (SEQ ID NO: 36) by PCR (0.5 min at 94° C., 0.5 min at 55° C., 1 min at 70° C., 30 cycles) using primers identified as SEQ ID NO: 46 and SEQ ID NO: 47 to generate the PCR product identified as SEQ ID NO: 48. E. coli MG1655 KatG1 (EXAMPLE 13) was transformed with the temperature-sensitive plasmid pKD46 (SEQ ID NO: 42), which contains the λ-Red recombinase genes, and selected on LB-amp plates for 24 h at 30° C. MG1655 KatG1/pKD46 was transformed with 50-500 ng of the PCR product by electroporation (BioRad Gene Pulser, 0.2 cm cuvette, 2.5 kV, 200 W, 25 uF), and selected on LB-kan plates for 24 h at 37° C. Several colonies were streaked onto LB-kan plates and incubated overnight at 42° C. to cure the pKD46 plasmid. Colonies were checked to confirm a phenotype of kanR/ampS. Genomic DNA was isolated from several colonies using the PUREGENE® DNA purification system, and checked by PCR to confirm disruption of the katE gene using primers identified as SEQ ID NO: 51 and SEQ ID NO: 52. Several katE-disrupted strains (ΔkatE) were transformed with the temperature-sensitive plasmid pCP20 (SEQ ID NO: 45), which contains the FLP recombinase, used to excise the kan gene, and selected on LB-amp plates for 24 h at 37° C. Several colonies were streaked onto LB plates and incubated overnight at 42° C. to cure the pCP20 plasmid. Two colonies were checked to confirm a phenotype of kanS/ampS, and called MG1655 KatG1KatE18.1 and MG1655 KatG1KatE23. MG1655 KatG1KatE18.1 is designated *E. coli* KLP18.

Example 4

Cloning and Expression of Perhydrolase from *Thermotoga neapolitana*

The gene encoding acetyl xylan esterase from *Thermotoga neapolitana* as reported in GENBANK® (accession #U58632) was synthesized using codons optimized for expression in *E. coli* (DNA 2.0, Menlo Park, Calif.). The gene was subsequently amplified by PCR (0.5 min at 94° C., 0.5 min at 55° C., 1 min at 70° C., 30 cycles) using primers identified as SEQ ID NO: 66 and SEQ ID NO: 67. The resulting nucleic acid product (SEQ ID NO: 68) was subcloned into pTrcHis2-TOPO® to generate the plasmid identified as pSW196. The plasmid pSW196 was used to transform *E. coli* KLP18 to generate the strain KLP18/pSW196. KLP18/pSW196 was grown in LB media at 37° C. with shaking up to OD600 nm=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein.

Example 5

Cloning and Expression of Perhydrolase from *Thermotoga maritima* MSB8

The gene encoding acetyl xylan esterase from *Thermotoga maritima* MSB8 as reported in GENBANK® (accession #NP_227893.1) was synthesized (DNA 2.0, Menlo Park, Calif.). The gene was subsequently amplified by PCR (0.5 min @94° C., 0.5 min @55° C., 1 min @70° C., 30 cycles) using primers identified as SEQ ID NO: 63 and SEQ ID NO: 64. The resulting nucleic acid product (SEQ ID NO: 65) was cut with restriction enzymes PstI and XbaI and subcloned between the PstI and XbaI sites in pUC19 to generate the plasmid identified as pSW207. The plasmid pSW207 was used to transform *E. coli* KLP18 to generate the strain identified as KLP18/pSW207. KLP18/pSW207 was grown in LB media at 37 C with shaking up to OD600 nm=0.4-0.5, at which time IPTG was added to a final concentration of 1 mM, and incubation continued for 2-3 hrs. Cells were harvested by centrifugation and SDS-PAGE was performed to confirm expression of the perhydrolase enzyme at 20-40% of total soluble protein.

Example 6

Cloning and Expression of Perhydrolase from *Bacillus subtilis* ATCC® 31954™

Genomic DNA was isolated from *Bacillus subtilis* ATCC® 31954™ using the PUREGENE® DNA purification system (Gentra Systems, Minneapolis Minn.). The perhydrolase gene was amplified from the genomic DNA by PCR (0.5 min at 94° C., 0.5 min at 55° C., 1 min at 70° C., 30 cycles) using primers identified as SEQ ID NO: 25 and SEQ ID NO: 26. The resulting nucleic acid product (SEQ ID NO: 27) was cut with restriction enzymes PstI and XbaI and subcloned between the PstI and XbaI sites in pUC19 to generate the plasmid identified as pSW194. The plasmid pSW194 was used to transform *E. coli* KLP18 to generate the strain identified as KLP18/pSW194. KLP18/pSW194 was grown in LB media at 37° C. with shaking up to $OD_{600nm}$=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein.

Example 7

Cloning and Expression of Perhydrolase from *Bacillus subtilis* BE1010

Genomic DNA was isolated from *Bacillus subtilis* BE1010 (Payne and Jackson 1991 *J. Bacteriol.* 173:2278-2282) using the PUREGENE® DNA purification system (Gentra Systems). The perhydrolase gene was amplified from the genomic DNA by PCR (0.5 min at 94° C., 0.5 min at 55° C., 1 min at 70° C., 30 cycles) using primers identified as SEQ ID NO: 25 and SEQ ID NO: 26. The resulting nucleic acid product (SEQ ID NO: 28) was cut with restriction enzymes PstI and XbaI and subcloned between the PstI and XbaI sites in pUC19 to generate the plasmid identified as pSW189. The plasmid pSW189 was used to transform *E. coli* KLP18 to generate the strain identified as KLP18/pSW189. KLP18/pSW189 was grown in LB media at 37° C. with shaking up to $OD_{600nm}$=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein.

Example 8

Cloning and Expression of Perhydrolase from *Bacillus pumilus* PS213

The gene encoding acetyl xylan esterase (axe1) from *B. pumilus* PS213 as reported in GENBANK® (accession #AJ249957) was synthesized using codons optimized for expression in *E. coli* (DNA 2.0, Menlo Park Calif.). The gene was subsequently amplified by PCR (0.5 min at 94° C., 0.5 min at 55° C., 1 min at 70° C., 30 cycles) using primers identified as SEQ ID NO: 33 and SEQ ID NO: 34. The resulting nucleic acid product (SEQ ID NO: 53) was subcloned into pTrcHis2-TOPO® (Invitrogen, Carlsbad Calif.) to generate the plasmid identified as pSW195. The plasmid pSW195 was used to transform *E. coli* KLP18 to generate the strain identified as KLP18/pSW195. KLP18/pSW195 was grown in LB media at 37° C. with shaking up to OD600 nm=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein.

Example 9

Cloning and Expression of Perhydrolase from *Bacillus licheniformis* ATCC® 14580™

Genomic DNA was isolated from *Bacillus licheniformis* ATCC®14580™ using the PUREGENE® DNA purification system. The perhydrolase gene was amplified from the genomic DNA by PCR (0.5 min at 94° C., 0.5 min at 55° C., 1 min at 70° C., 30 cycles) using primers identified as SEQ ID NO: 31 and SEQ ID NO: 32. The resulting nucleic acid product (SEQ ID NO: 7) was subcloned into pTrcHis2-TOPO® to generate the plasmid identified as pSW191. The plasmid pSW191 was used to transform *E. coli* KLP18 to generate the strain identified as KLP18/pSW191. KLP18/pSW191 was grown in LB media at 37° C. with shaking up to $OD_{600nm}$=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein.

Example 10

Fermentation of *E. coli* KLP18 Transformants Expressing Perhydrolase

A fermentor seed culture was prepared by charging a 2-L shake flask with 0.5 L seed medium containing yeast extract (Amberx 695, 5.0 g/L), $K_2HPO_4$ (10.0 g/L), $KH_2PO_4$ (7.0 g/L), sodium citrate dihydrate (1.0 g/L), $(NH_4)_2SO_4$ (4.0 g/L), $MgSO_4$ heptahydrate (1.0 g/L) and ferric ammonium citrate (0.10 g/L). The pH of the medium was adjusted to 6.8 and the medium was sterilized in the flask. Post sterilization additions included glucose (50 wt %, 10.0 mL) and 1 mL ampicillin (25 mg/mL) stock solution. The seed medium was inoculated with a 1-mL culture of *E. coli* KLP18/pSW189, *E. coli* KLP18/pSW191, *E. coli* KLP18/pSW194, *E. coli* KLP18/pSW195, *E. coli* KLP18/pSW196, or *E. coli* KLP18/pSW207 in 20% glycerol, and cultivated at 35° C. and 300 rpm. The seed culture was transferred at ca. 1-2 $OD_{550}$ to a 14 L fermentor (Braun) with 8 L of medium at 35° C. containing $KH_2PO_4$ (3.50 g/L), $FeSO_4$ heptahydrate (0.05 g/L), $MgSO_4$ heptahydrate (2.0 g/L), sodium citrate dihydrate (1.90 g/L), yeast extract (Ambrex 695, 5.0 g/L), Biospumex153K antifoam (0.25 mL/L, Cognis Corporation), NaCl (1.0 g/L), $CaCl_2$ dihydrate (10 g/L), and NIT trace elements solution (10 mL/L). The trace elements solution contained citric acid monohydrate (10 g/L), $MnSO_4$ hydrate (2 g/L), NaCl (2 g/L), $FeSO_4$ heptahydrate (0.5 g/L), $ZnSO_4$ heptahydrate (0.2 g/L), $CuSO_4$ pentahydrate (0.02 g/L) and $NaMoO_4$ dihydrate (0.02 g/L). Post sterilization additions included glucose solution (50% w/w, 80.0 g) and ampicillin (25 mg/mL) stock solution (16.00 mL). Glucose solution (50% w/w) was used for fed batch. Glucose feed was initiated when glucose concentration decreased to 0.5 g/L, starting at 0.31 g feed/min and increasing progressively each hour to 0.36, 0.42, 0.49, 0.57, 0.66, 0.77, 0.90, 1.04, 1.21, 1.41 1.63 g/min respectively; the rate remained constant afterwards. Glucose concentration in the medium was monitored and if the concentration exceeded 0.1 g/L the feed rate was decreased or stopped temporarily. Induction was initiated between $OD_{550}$=56 and $OD_{550}$=80 with addition of 16 mL IPTG (0.5 M) for the various strains. The dissolved oxygen (DO) concentration was controlled at 25% of air saturation. The DO was controlled first by impeller agitation rate (400 to 1400 rpm) and later by aeration rate (2 to 10 slpm). The pH was controlled at 6.8. $NH_4OH$ (29% w/w) and $H_2SO_4$ (20% w/v) were used for pH control. The head pressure was 0.5 bars. The cells were harvested by centrifugation 16 h post IPTG addition.

Example 11

Dependence of Specific Activity on pH for CE-7 Esterases/Perhydrolases

A cell extract of an *E. coli* transformant expressing perhydrolase from *Thermotoga neapolitana* (KLP18/pSW196), *Thermotoga maritima* MSB8 (KLP18/pSW207), *Bacillus pumilus* PS213 (KLP1S/pSW195), *Bacillus subtilis* BE1010 (KLP18/pSW189), *Bacillus subtilis* ATCC® 31954™ (KLP18/pSW194), or *Bacillus licheniformis* ATCC® 14580™ (KLP18/pSW191) was prepared by passing a suspension of cell paste (20 wt % wet cell weight) in 0.05 M potassium phosphate buffer (pH 7.0) containing dithiothreitol (1 mM) twice through a French press having a working pressure of 16,000 psi (~110 MPa). The crude extract was then centrifuged at 20,000×g to remove cellular debris, producing a clarified cell extract that was assayed for total soluble protein (Bicinchoninic Acid Kit for Protein Determination, Sigma Aldrich catalog #BCA1-KT). A portion of the clarified *Thermotoga maritima* MSB8 or *Thermotoga neapolitana* perhydrolase-containing extract was additionally heated for 20 min at 75° C., followed immediately by cooling in an ice/water bath to 5° C. The resulting mixture was centrifuged to remove precipitated protein, and the supernatant collected and assayed for total soluble protein as before. SDS-PAGE of the heat-treated supernatant indicated that the perhydrolase constituted at least ca. 90% of the total soluble protein present in the supernatant.

Reactions (10 mL total volume) containing triacetin (200 mM) and cell extract supernatant (prepared as described above) were run at 25° C. and at a pH between 4.5 and 10.0, using the buffers and buffer concentrations listed in Table 5. The concentration of extract total protein (with or without heat-treatment to denature and precipitate *E. coli*-derived protein) was chosen to produce an ca. 50 mM decrease in triacetin concentration over 30 min (typically from 0.025 mg/mL to 0.40 mg/mL of total extract protein, dependent on the perhydrolase). A control reaction for each reaction condition was run to determine the concentration of triacetin hydrolyzed in the absence of added extract protein. Samples (100 µL) were removed at predetermined times and immediately added to 297 µL of dd $H_2O$ and 3 µL of 6N HCL. The resulting solution was mixed, then filtered using a 30,000 NMWL filter (Millipore) using a microcentrifuge for 2 min at 12,000 rpm. An aliquot of the filtrate (100 µL) was added to 150 µL of 0.417 mM N,N-diethyl meta-toluamide (external standard) in acetonitrile, and the resulting solution analyzed for triacetin by HPLC using a Supelco Discovery C8 column (25 cm×4.0 mm, 5 um; Supelco #59353-U40) and an isocratic mobile phase of 40% acetonitrile/60% distilled water at a flow rate of 1 mL/min. Triacetin was measured by UV detection at 225 nm. The dependence of specific activity on pH for each perhydrolase is listed in Table 6.

TABLE 5

Buffer and buffer concentration employed for determination of dependence of CE-7 esterase/perhydrolase specific activity on pH.

| pH | Buffer | Buffer Concentration (M) |
|---|---|---|
| 5.0 | sodium acetate | 0.15 |
| 5.5 | sodium acetate | 0.15 |
| 6.0 | sodium citrate | 0.15 |
| 6.5 | sodium citrate | 0.15 |
| 7.0 | potassium phosphate | 0.15 |
| 7.5 | potassium phosphate | 0.15 |
| 8.0 | potassium phosphate | 0.20 |
| 8.5 | Tris(hydroxymethyl)aminomethane | 0.20 |
| 9.0 | Tris(hydroxymethyl)aminomethane | 0.20 |
| 9.5 | glycine | 0.20 |
| 10.0 | glycine | 0.20 |

TABLE 6

Dependence of specific activity (mmol triacetin/min/mg total extract protein) on pH for hydrolysis of triacetin by perhydrolases expressed in *E. coli* KLP18 transformants using 200 mM triacetin and 0.050-0.40 mg/mL of cell extract total protein (ND = not determined).

| | specific activity (mmol triacetin/min/mg total extract protein) | | | | | |
|---|---|---|---|---|---|---|
| pH | Thermotoga neapolitana | Thermotoga maritima MSB8 | Bacillus pumilus | Bacillus subtilis BE1010 | Bacillus subtilis ATCC® 31954™ | Bacillus. licheniformis. |
| 10.0 | 0 | ND | ND | ND | 0 | ND |
| 9.5 | 12.0 | 21.6 | 71.1 | ND | 193 | ND |
| 9.0 | 12.5 | 57.1 | 80.4 | ND | 239 | ND |
| 8.5 | 11.3 | 38.8 | 72.4 | ND | 217 | ND |
| 8.0 | 5.8 | 28.7 | 53.9 | ND | 221 | ND |
| 7.5 | 5.3 | 19.8 | 33.7 | 61.0 | 205 | 62.4 |
| 7.0 | 3.3 | 16.0 | 30.5 | 37.7 | 120 | 56.3 |
| 6.5 | 1.7 | 10.3 | 11.6 | 18.6 | 78.0 | 23.8 |
| 6.0 | 0.4 | 4.3 | 4.2 | 7.4 | 24.0 | 12.3 |
| 5.5 | 0 | 1.4 | 3.5 | 0 | 17.6 | 4.7 |
| 5.0 | | ND | 1.8 | | 7.6 | ND |
| 4.5 | | | ND | | 0.5 | |

Example 12

Control of Peracetic Acid Production by *Thermotoga neapolitana* Perhydrolase Using Buffer Concentration A cell extract of an *E. coli* transformant expressing perhydrolase from *Thermotoga neapolitana* (KLP18/pSW196) was prepared by passing a suspension of cell paste (20 wt % wet cell weight) in 0.05 M potassium phosphate buffer (pH 7.0) containing dithiothreitol (1 mM) twice through a French press having a working pressure of 16,000 psi (~110 MPa). The crude extract was then centrifuged at 20,000×g to remove cellular debris, producing a clarified cell extract that was assayed for total soluble protein (Bicinchoninic Acid Kit for Protein Determination, Sigma Aldrich catalog #BCA1-KT). The clarified extract was heated for 20 min at 75° C., followed immediately by cooling in an ice/water bath. The resulting mixture was centrifuged to remove precipitated protein, and the supernatant collected and assayed for total soluble protein as before. SDS-PAGE of the supernatant indicated that the perhydrolase was at least 90% pure. The supernatant was frozen in dry ice and stored at −80° C.

Reactions (10 mL total volume) containing triacetin, hydrogen peroxide and heat-treated, centrifuged cell extract supernatant (prepared as described above) were run at 25° C. using sodium bicarbonate buffer concentrations listed in Tables 7 and 8. A control reaction for each reaction condition was run to determine the concentration of peracetic acid produced by chemical perhydrolysis of triacetin by hydrogen peroxide in the absence of added extract protein. Determination of the concentration of peracetic acid in the reaction mixtures was performed according to the method described by Karst et al., supra. Aliquots (0.040 mL) of the reaction mixture were removed at predetermined times and mixed with 0.960 mL of 5 mM phosphoric acid in water; adjustment of the pH of the diluted sample to less than pH 4 immediately terminated the reaction. The resulting solution was filtered using an ULTRAFREE® MC-filter unit (30,000 Normal Molecular Weight Limit (NMWL), Millipore cat #UFC3LKT 00) by centrifugation for 2 min at 12,000 rpm. An aliquot (0.100 mL) of the resulting filtrate was transferred to L5-mL screw cap HPLC vial (Agilent Technologies, Palo Alto, Calif.; #5182-0715) containing 0.300 mL of deionized water, then 0.100 mL of 20 mM MTS (methyl-p-tolyl-sulfide) in acetonitrile was added, the vials capped, and the contents briefly mixed prior to a 10 min incubation at ca. 25° C. in the absence of light. To each vial was then added 0.400 mL of acetonitrile and 0.100 mL of a solution of triphenylphosphine (TPP, 40 mM) in acetonitrile, the vials re-capped, and the resulting solution mixed and incubated at ca. 25° C. for 30 min in the absence of light. To each vial was then added 0.100 mL of 10 mM N,N-diethyl-m-toluamide (DEET; HPLC external standard) and the resulting solution analyzed by HPLC as described below.

HPLC Method:

Supelco Discovery C8 column (10-cm×4.0-mm, 5 μm) (cat. #569422-U) w/precolumn Supelco Supelguard Discovery C8 (Sigma-Aldrich; cat #59590-U); 10 microliter injection volume; gradient method with $CH_3CN$ (Sigma-Aldrich; #270717) and deionized water at 1.0 mL/min and ambient temperature:

| Time (min:sec) | (% $CH_3CN$) |
|---|---|
| 0:00 | 40 |
| 3:00 | 40 |
| 3:10 | 100 |
| 4:00 | 100 |
| 4:10 | 40 |
| 7:00 (stop) | 40 |

The peracetic acid concentrations produced in 1 min, 5 min and 30 min when using either 250 mM or 100 mM hydrogen peroxide are listed in Table 7 and Table 8, respectively.

TABLE 7

Dependence of peracetic acid (PAA) concentration on concentration of bicarbonate buffer when using 100 mM triacetin, 250 mM hydrogen peroxide and 50 µg/mL of *E. coli* KLP18/pSW196 heat-treated extract total protein containing *Thermotoga neapolitana* perhydrolase.

| heated extract total protein (µg protein/mL) | NaHCO₃ buffer (mM) | initial pH | PAA (ppm), 1 min | pH, 1 min | PAA (ppm), 5 min | pH, 5 min | PAA (ppm), 30 min | pH, 30 min |
|---|---|---|---|---|---|---|---|---|
| 0 | 25 | 8.1 | 139 | 8.0 | 385 | 7.5 | 610 | 7.2 |
| 50 | 25 | 8.1 | 1037 | 6.8 | 2655 | 6.0 | 3503 | 5.8 |
| 0 | 10 | 7.5 | 88 | 7.5 | 206 | 7.5 | 453 | 7.0 |
| 50 | 10 | 7.0 | 1042 | 7.0 | 2334 | 5.5 | 2384 | 5.0 |
| 0 | 5.0 | 6.5 | 84 | 6.5 | 163 | 6.5 | 296 | 6.0 |
| 50 | 5.0 | 6.5 | 866 | 6.5 | 1894 | 5.5 | 1931 | 5.0 |
| 0 | 2.5 | 6.5 | 48 | 5.5 | 129 | 5.5 | 210 | 5.5 |
| 50 | 2.5 | 6.5 | 718 | 5.5 | 1242 | 5.0 | 1179 | 5.0 |
| 0 | 1.0 | 6.0 | 15 | 6.0 | 115 | 6.0 | 194 | 5.5 |
| 50 | 1.0 | 6.0 | 511 | 5.0 | 610 | 5.0 | 608 | 5.0 |
| 0 | 0 | 5.0 | 41 | 5.0 | 63 | 5.0 | 79 | 5.0 |
| 50 | 0 | 5.0 | 161 | 5.0 | 152 | 5.0 | 180 | 5.0 |

TABLE 8

Dependence of peracetic acid (PAA) concentration on concentration of bicarbonate buffer when using 100 mM triacetin, 100 mM hydrogen peroxide and 50 µg/mL of *E. coli* KLP18/pSW196 heat-treated extract total protein containing *Thermotoga neapolitana* perhydrolase.

| heated extract total protein (µg protein/mL) | NaHCO₃ buffer (mM) | initial pH | PAA (ppm), 1 min | pH, 1 min | PAA (ppm), 5 min | pH, 5 min | PAA (ppm), 30 min | pH, 30 min |
|---|---|---|---|---|---|---|---|---|
| 0 | 25 | 8.1 | 74 | 8.0 | 220 | 7.8 | 383 | 7.5 |
| 50 | 25 | 8.1 | 497 | 7.5 | 1319 | 6.5 | 2095 | 6.0 |
| 0 | 10 | 8.1 | 55 | 7.5 | 122 | 7.0 | 226 | 7.0 |
| 50 | 10 | 8.1 | 418 | 6.2 | 1035 | 6.0 | 1633 | 5.3 |
| 0 | 5.0 | 6.5 | 36 | 6.5 | 119 | 6.5 | 126 | 6.0 |
| 50 | 5.0 | 6.5 | 377 | 6.0 | 955 | 5.5 | 989 | 5.0 |
| 0 | 2.5 | 6.5 | 20 | 6.3 | 33 | 6.0 | 73 | 6.0 |
| 50 | 2.5 | 6.5 | 291 | 5.5 | 510 | 5.3 | 488 | 5.0 |
| 0 | 1.0 | 6.0 | 2 | 6.0 | 15 | 5.8 | 103 | 5.5 |
| 50 | 1.0 | 6.0 | 167 | 5.0 | 152 | 5.0 | 176 | 5.0 |
| 0 | 0 | 5.0 | 0 | 5.0 | 15 | 5.0 | 31 | 5.0 |
| 50 | 0 | 5.0 | 0 | 5.0 | 29 | 5.0 | 11 | 5.0 |

Example 13

Control of Peracetic Acid Production by *Thermotoga maritima* MSB8 Perhydrolase Using Buffer Concentration A cell extract of a transformant expressing perhydrolase from *Thermotoga maritima* MSB8 (KLP18/pSW207) was prepared by passing a suspension of cell paste (20 wt % wet cell weight) in 0.05 M potassium phosphate buffer (pH 7.0) containing dithiothreitol (1 mM) twice through a French press having a working pressure of 16,000 psi (~110 MPa). The crude extract was then centrifuged at 20,000×g to remove cellular debris, producing a clarified cell extract that was assayed for total soluble protein (Bicinchoninic Acid Kit for Protein Determination, Sigma Aldrich catalog #BCA1-KT). The clarified extract was heated for 20 min at 75° C., followed immediately by cooling in an ice/water bath. The resulting mixture was centrifuged to remove precipitated protein, and the supernatant collected and assayed for total soluble protein as before. SDS-PAGE of the supernatant indicated that the perhydrolase was at least 85-90% pure. The supernatant was frozen in dry ice and stored at −80° C.

Reactions (2 mL total volume) containing triacetin, hydrogen peroxide and heat-treated, centrifuged cell extract supernatant (prepared as described above) were run at 25° C. using sodium bicarbonate buffer concentrations listed in Tables 9 and 10. A control reaction for each reaction condition was run to determine the concentration of peracetic acid produced by chemical perhydrolysis of triacetin by hydrogen peroxide in the absence of added extract protein. Determination of the concentration of peracetic acid in the reaction mixtures was performed according to the method described by Karst et al., supra. The peracetic acid concentrations produced in 1 min, 5 min and 30 min using either 250 mM or 100 mM hydrogen peroxide are listed in Table 9 and Table 10.

TABLE 9

Dependence of peracetic acid (PAA) concentration on concentrations of bicarbonate buffer when using 100 mM triacetin, 250 mM hydrogen peroxide and 50 µg/mL of *E. coli* KLP18/pSW207 heat-treated extract total protein containing *Thermotoga maritima* MSB8 perhydrolase.

| heated extract total protein (µg protein/mL) | NaHCO₃ buffer (mM) | initial pH | PAA (ppm), 1 min | pH, 1 min | PAA (ppm), 5 min | pH, 5 min | PAA (ppm), 30 min | pH, 30 min |
|---|---|---|---|---|---|---|---|---|
| 0  | 25  | 8.1 | 144 | 8.0 | 324  | 8.0 | 759  | 7.2 |
| 50 | 25  | 8.1 | 848 | 7.0 | 2342 | 6.5 | 3251 | 6.0 |
| 0  | 10  | 7.5 | 182 | 7.0 | 194  | 7.0 | 454  | 6.5 |
| 50 | 10  | 7.0 | 804 | 6.3 | 1951 | 5.5 | 2698 | 5.0 |
| 0  | 5.0 | 6.5 | 84  | 6.5 | 163  | 6.5 | 296  | 6.0 |
| 50 | 5.0 | 6.5 | 735 | 6.0 | 1825 | 5.7 | 2222 | 5.0 |
| 0  | 2.5 | 6.5 | 48  | 5.5 | 129  | 5.5 | 210  | 5.5 |
| 50 | 2.5 | 6.5 | 817 | 5.5 | 1758 | 5.3 | 1748 | 5.0 |
| 0  | 1.0 | 6.0 | 15  | 6.0 | 115  | 6.0 | 194  | 5.5 |
| 50 | 1.0 | 6.0 | 690 | 5.0 | 980  | 5.0 | 981  | 5.0 |
| 0  | 0   | 5.0 | 0   | 5.0 | 75   | 5.0 | 63   | 5.0 |
| 50 | 0   | 5.0 | 233 | 5.0 | 290  | 5.0 | 289  | 5.0 |

TABLE 10

Dependence of peracetic acid (PAA) concentration on concentrations of bicarbonate buffer when using 100 mM triacetin, 100 mM hydrogen peroxide and 50 µg/mL of *E. coli* KLP18/pSW207 heat-treated extract total protein containing *Thermotoga maritima* MSB8 perhydrolase.

| heated extract total protein, (µg protein/mL) | NaHCO₃ buffer (mM) | initial pH | PAA (ppm), 1 min | pH, 1 min | PAA (ppm), 5 min | pH, 5 min | PAA (ppm), 30 min | pH, 30 min |
|---|---|---|---|---|---|---|---|---|
| 0  | 25  | 8.1 | 95  | 8.0 | 223  | 8.0 | 456  | 7.5 |
| 50 | 25  | 8.1 | 465 | 7.5 | 1369 | 6.8 | 2217 | 6.0 |
| 0  | 10  | 8.1 | 73  | 7.5 | 138  | 7.5 | 222  | 7.0 |
| 50 | 10  | 8.1 | 407 | 6.5 | 1075 | 6.0 | 1763 | 5.3 |
| 0  | 5.0 | 6.5 | 41  | 6.5 | 83   | 6.5 | 174  | 6.0 |
| 50 | 5.0 | 6.5 | 330 | 6.0 | 972  | 5.7 | 1323 | 5.0 |
| 0  | 2.5 | 6.5 | 20  | 6.3 | 33   | 6.0 | 73   | 6.0 |
| 50 | 2.5 | 6.5 | 319 | 5.7 | 755  | 5.3 | 710  | 5.0 |
| 0  | 1.0 | 6.0 | 2   | 6.0 | 15   | 5.8 | 103  | 5.5 |
| 50 | 1.0 | 6.0 | 238 | 5.0 | 388  | 5.0 | 361  | 5.0 |
| 0  | 0   | 5.0 | 12  | 5.0 | 16   | 5.0 | 31   | 5.0 |
| 50 | 0   | 5.0 | 125 | 5.0 | 121  | 5.0 | 105  | 5.0 |

Example 14

Control of Peracetic Acid Production by *Thermotoga maritima* MSB8 Perhydrolase by Selection of Buffer, Reactant and Perhydrolase Concentrations Reactions (10 mL total volume) containing triacetin (100 mM), hydrogen peroxide (100 mM or 250 mM) and heat-treated, centrifuged cell extract supernatant (35 to 100 µg total heat-treated extract protein/mL, prepared as described in Example 13) prepared from an *E. coli* transformant expressing perhydrolase from *Thermotoga maritima* MSB8 (KLP18/pSW207) in sodium citrate (50 mM, pH 6.5) buffer, or in sodium bicarbonate buffer (1 mM to 5 mM, initial pH as indicated in Table 12), or in water without added buffer were run at 25° C. A control reaction for each reaction condition was run to determine the concentration of peracetic acid produced by chemical perhydrolysis of triacetin by hydrogen peroxide in the absence of added extract protein. Determination of the concentration of peracetic acid in the reaction mixtures was performed according to the method described by Karst et al., supra. The peracetic acid concentration produced at predetermined reaction times is listed in Table 11, and the corresponding reaction pH at each reaction time is listed in Table 12.

TABLE 11

Dependence of peracetic acid (PAA) concentration over time on buffer, perhydrolase and hydrogen peroxide concentrations when reacting triacetin (100 mM) and hydrogen peroxide (100 mM or 250 mM) in the presence or absence of perhydrolase from *E. coli* KLP18/pSW207 heat-treated extract total protein containing *Thermotoga maritima* MSB8 perhydrolase.

| buffer, conc. | $H_2O_2$ (mM) | total protein (μg/mL) | PAA (ppm), 1 min | PAA (ppm), 5 min | PAA (ppm), 30 min | PAA (ppm), 2 h | PAA (ppm), 18 h |
|---|---|---|---|---|---|---|---|
| citrate, 50 mM | 100 | 0 | 155 | 0 | 0 | 119 | 522 |
| citrate, 50 mM | 100 | 50 | 409 | 892 | 2001 | 2254 | 1937 |
| bicarbonate, 5 mM | 100 | 0 | 64 | 115 | 269 | 369 | 419 |
| bicarbonate, 5 mM | 100 | 50 | 410 | 1088 | 1496 | 1423 | 1419 |
| bicarbonate, 1 mM | 250 | 0 | 0 | 22 | 229 | 280 | 258 |
| bicarbonate, 1 mM | 250 | 50 | 624 | 1060 | 1090 | 1063 | 1021 |
| bicarbonate, 1 mM | 250 | 0 | 18 | 105 | 236 | 275 | 149 |
| bicarbonate, 1 mM | 250 | 35 | 467 | 1047 | 1041 | 1014 | 917 |
| bicarbonate, 2.5 mM | 100 | 0 | 54 | 38 | 156 | 293 | 346 |
| bicarbonate, 2.5 mM | 100 | 50 | 256 | 722 | 976 | 887 | 855 |
| bicarbonate, 1 mM | 100 | 0 | 28 | 78 | 141 | 204 | 164 |
| bicarbonate, 1 mM | 100 | 75 | 434 | 494 | 608 | 673 | 576 |
| bicarbonate, 1 mM | 100 | 100 | 449 | 667 | 643 | 703 | 613 |
| water (no buffer) | 250 | 0 | 13 | 71 | 71 | 33 | 45 |
| water (no buffer) | 250 | 75 | 512 | 535 | 533 | 472 | 448 |
| water (no buffer) | 250 | 100 | 576 | 668 | 654 | 618 | 543 |

TABLE 12

Dependence of reaction pH over time on buffer, perhydrolase and hydrogen peroxide concentrations when reacting triacetin (100 mM) and hydrogen peroxide (100 mM or 250 mM) in the presence or absence of perhydrolase from *E. coli* KLP18/pSW207 heat-treated extract total protein containing *Thermotoga maritima* MSB8 perhydrolase (from reactions listed in Table 11).

| buffer, conc. | $H_2O_2$ (mM) | total protein (μg/mL) | initial pH | pH, 1 min | pH, 5 min | pH, 30 min | pH, 2 h | pH, 18 h |
|---|---|---|---|---|---|---|---|---|
| citrate, 50 mM | 100 | 0 | 6.5 | 6.5 | 6.5 | 6.5 | 6.5 | 6.5 |
| citrate, 50 mM | 100 | 50 | 6.5 | 6.5 | 6.5 | 6.2 | 6.0 | 6.0 |
| bicarbonate, 5 mM | 100 | 0 | 6.5 | 6.5 | 6.5 | 6.2 | 6.0 | 5.0 |
| bicarbonate, 5 mM | 100 | 50 | 6.5 | 6.0 | 5.5 | 5.0 | 5.0 | 5.0 |
| bicarbonate, 1 mM | 250 | 0 | 6.0 | 6.0 | 6.0 | 5.5 | 5.0 | 5.0 |
| bicarbonate, 1 mM | 250 | 50 | 6.0 | 5.0 | 5.0 | 5.0 | 5.0 | 5.0 |
| bicarbonate, 1 mM | 250 | 0 | 6.0 | 6.0 | 6.0 | 5.5 | 5.0 | 5.0 |
| bicarbonate, 1 mM | 250 | 35 | 6.0 | 5.5 | 5.0 | 5.0 | 5.0 | 5.0 |
| bicarbonate, 2.5 mM | 100 | 0 | 6.5 | 6.5 | 6.5 | 6.0 | 5.5 | 5.0 |
| bicarbonate, 2.5 mM | 100 | 50 | 6.5 | 5.7 | 5.0 | 5.0 | 5.0 | 5.0 |
| bicarbonate, 1 mM | 100 | 0 | 6.0 | 6.0 | 6.0 | 5.0 | 5.0 | 4.5 |
| bicarbonate, 1 mM | 100 | 75 | 6.0 | 5.0 | 5.0 | 5.0 | 5.0 | 4.5 |
| bicarbonate, 1 mM | 100 | 100 | 6.0 | 5.0 | 5.0 | 5.0 | 5.0 | 4.5 |
| no added buffer | 250 | 0 | 5.0 | 5.0 | 5.0 | 5.0 | 5.0 | 4.5 |
| no added buffer | 250 | 75 | 5.0 | 5.0 | 5.0 | 5.0 | 5.0 | 4.5 |
| no added buffer | 250 | 100 | 5.0 | 5.0 | 5.0 | 5.0 | 5.0 | 4.5 |

Example 15

Control of Peracetic Acid Production by Perhydrolase Using Initial Reaction pH

A cell extract of a transformant expressing perhydrolase from *Bacillus pumilus* PS213 (KLP18/pSW195), *Thermotoga maritima* MSB8 (KLP18/pSW207), *Thermotoga neapolitana* (KLP18/pSW196), or *Bacillus subtilis* ATCC® 31954™ (KLP18/pSW194) was prepared by passing a suspension of cell paste (20 wt % wet cell weight) in 0.05 M potassium phosphate buffer (pH 7.0) containing dithiothreitol (1 mM) twice through a French press having a working pressure of 16,000 psi (~110 MPa). The crude extract was then centrifuged at 20,000×g to remove cellular debris, producing a clarified cell extract that was assayed for total soluble protein (Bicinchoninic Acid Kit for Protein Determination, Sigma Aldrich catalog #BCA1-KT). The supernatant was frozen in dry ice and stored at −80° C.

Reactions (10 mL total volume) containing triacetin, hydrogen peroxide and centrifuged cell extract supernatant (prepared as described above) in 50 mM sodium citrate buffer (initial pH 7.2 or 6.5) were run at 25° C. A control reaction for each reaction condition was run to determine the concentration of peracetic acid produced by chemical perhydrolysis of triacetin by hydrogen peroxide in the absence of added extract protein (data not shown). Determination of the concentration of peracetic acid in the reaction mixtures was performed according to the method described by Karst et al., supra. The peracetic acid concentrations produced in 1 min, 5 min and 30 min are listed in Table 13.

TABLE 13

Dependence of peracetic acid (PAA) concentration on initial reaction pH in sodium citrate buffer (50 mM, initial pH of 7.2 or 6.5) at 25° C. using 0.050 mg/mL of extract total protein from *E. coli* KLP18/pSW195 (*Bacillus pumilus* PS213 perhydrolase), *E. coli* KLP18/pSW207 (*Thermotoga maritima* MSB8 perhydrolase), *E. coli* KLP18/pSW196 (*Thermotoga neapolitana* perhydrolase), or *E. coli* KLP18/pSW194 (*Bacillus subtilis* ATCC ® 31954 ™ perhydrolase).

| perhydrolase | initial pH | triacetin (mM) | $H_2O_2$ (mM) | PAA, 1 min (ppm) | PAA, 5 min (ppm) | PAA, 30 min (ppm) |
|---|---|---|---|---|---|---|
| *B. pumilus* PS213 | 7.2 | 100 | 250 | 465 | 1170 | 2525 |
| *B. pumilus* PS213 | 6.5 | 100 | 250 | 281 | 652 | 1984 |
| *B. pumilus* PS213 | 7.2 | 100 | 100 | 160 | 322 | 1010 |
| *B. pumilus* PS213 | 6.5 | 100 | 100 | 170 | 310 | 830 |
| *T. neapolitana* | 7.2 | 100 | 250 | 1790 | 2860 | 3820 |
| *T. neapolitana* | 6.5 | 100 | 250 | 434 | 1260 | 2016 |
| *T. neapolitana* | 7.2 | 100 | 100 | 798 | 1748 | 2500 |
| *T. neapolitana* | 6.5 | 100 | 100 | 221 | 607 | 1925 |
| *T. maritima* MSB8 | 7.2 | 100 | 250 | 635 | 1725 | 3565 |
| *T. maritima* MSB8 | 6.5 | 100 | 250 | 95 | 742 | 2446 |
| *T. maritima* MSB8 | 7.2 | 100 | 100 | 210 | 610 | 1995 |
| *T. maritima* MSB8 | 6.5 | 100 | 100 | 53 | 279 | 1540 |
| *B. subtilis* ATCC 31954 | 7.2 | 100 | 250 | 2430 | 2820 | 4400 |
| *B. subtilis* ATCC 31954 | 6.5 | 100 | 250 | 1725 | 2570 | 3712 |
| *B. subtilis* ATCC 31954 | 7.2 | 100 | 100 | 1040 | 1240 | 2395 |
| *B. subtilis* ATCC 31954 | 6.5 | 100 | 100 | 691 | 1286 | 1880 |

What is claimed is:

1. A process for disinfecting a hard surface or inanimate object by producing a target concentration of peroxycarboxylic acid comprising:
 a. selecting a set of reaction components to produce a target concentration of peroxycarboxylic acid, said reaction components comprising:
  1) at least one:
   i) ester having the structure $[X]_m R_5$ wherein X is an ester group of the formula $R_6C(O)O$;
   $R_6$ is a C1 to C7 linear, branched or cyclic hydrocarbyl moiety, optionally substituted with hydroxyl groups or C1 to C4 alkoxy groups, wherein $R_6$ optionally comprises one or more ether linkages when $R_6$ is C2 to C7;
   $R_5$ is a C1 to C6 linear, branched, or cyclic hydrocarbyl moiety optionally substituted with hydroxyl groups; wherein each carbon atom in $R_5$ individually comprises no more than one hydroxyl group or no more than one ester group;
   wherein $R_5$ optionally comprises one or more ether linkages;
   m is an integer from 1 to the number of carbon atoms in $R_5$;
   said ester having a solubility in water of at least 5 parts per million at 25° C.; or
   ii) glyceride having the structure

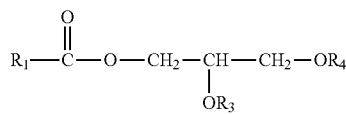

wherein $R_1$ is $C_1$ to $C_7$ straight chain or branched chain alkyl optionally substituted with an hydroxyl or a C1 to C4 alkoxy group and $R_3$ and $R_4$ are individually H or $R_1C(O)$; or
   iii) acetylated monosaccharide, acetylated disaccharide, or acetylated polysaccharide;
   or mixtures thereof;

2) a source of peroxygen;
  3) an enzyme catalyst having perhydrolysis activity, wherein said enzyme catalyst comprises an enzyme having a CE-7 signature motif that aligns with a reference sequence SEQ ID NO: 2 using CLUSTALW, said signature motif comprising:
   i) an RGQ motif at amino acid positions 118-120 of SEQ ID NO:2;
   ii) a GXSQG motif at amino acid positions 179-183 of SEQ ID NO:2; and
   iii) an HE motif at amino acid positions 298-299 of SEQ ID NO:2; and
   wherein said enzyme comprises at least 30% amino acid identity to SEQ ID NO: 2; and
  4) optionally at least one buffer;
 b. combining the selected set of reaction components under aqueous reaction conditions to form a reaction mixture; whereby reaction products are formed comprising peroxycarboxylic acid; wherein the reaction products comprising peroxycarboxylic acid reduce the reaction mixture pH to less than about 6.0 within about 1 minute to about 10 minutes of combining the reaction components and produce the target concentration of peroxycarboxylic acid; wherein the reduction in the reaction mixture pH is used to control the target concentration of peroxycarboxylic acid produced; and
 c. applying the peroxycarboxylic acid produced in step (b) to a hard surface or inanimate object.

2. The process of claim 1, wherein the at least one buffer is present in a concentration in a range from about 0.01 mM to about 200 mM.

3. The process of claim 1, wherein the reaction products reduce the reaction mixture pH to about 5.0 within about 1 minute to about 10 minutes of combining the reaction components.

4. The process of claim 1, wherein the target concentration of peroxycarboxylic acid is from about 200 parts per million to about 2500 parts per million.

5. The process of claim 4, wherein the target concentration of peroxycarboxylic acid is from about 400 parts per million to about 1200 parts per million.

6. The process of claim 5, wherein the target concentration of peroxycarboxylic acid is from about 400 parts per million to about 600 parts per million.

7. The process of claim 1, wherein the target concentration of peroxycarboxylic acid is achieved within about 1 to about 10 minutes of mixing the reaction components.

8. The process of claim 1, wherein the target concentration of peroxycarboxylic acid is achieved within at least about 5 minutes of mixing the reaction components.

9. The process of claim 8, wherein the target concentration of peroxycarboxylic acid is achieved within about 1 minute of mixing the reaction components.

10. The process of claim 1, wherein the concentration of peroxycarboxylic acid changes by less than about 20% of said target concentration once the target concentration of peroxycarboxylic acid is achieved.

11. The process of claim 1, wherein the buffer has a pKa from about 8.0 to about 6.0.

12. The process of claim 1, wherein the initial pH of the initial reaction mixture is selected from the group consisting of 6.5, 7.2, 7.5, 8.1, and 8.5.

13. The process of claim 1, wherein enzyme catalyst having perhydrolysis activity is derived from *Thermotoga neapolitana*.

14. The process of claim 1, wherein enzyme catalyst having perhydrolysis activity is derived from *Thermotoga maritima* MSB8.

15. The process of claim 1, wherein the reduction in pH reduces perhydrolase activity by about 80% or more in 10 minutes or less after combining the reaction components.

16. The process of claim 1 wherein the enzyme catalyst is in the form of a microbial cell, a permeabilized microbial cell, a microbial cell extract, a partially purified enzyme, a purified enzyme, or an immobilized form of a partially purified or purified enzyme.

17. The process of claim 1 wherein the peroxycarboxylic acid is selected from the group consisting of peracetic acid, perpropionic acid, perbutyric acid, perlactic acid, perglycolic acid, permethoxyacetic acid, per-β-hydroxybutyric acid, and mixtures thereof.

18. The process of claim 1 wherein the enzyme catalyst lacks catalase activity.

* * * * *